United States Patent
Johansen et al.

(10) Patent No.: US 10,259,801 B2
(45) Date of Patent: Apr. 16, 2019

(54) ANTI-INFLAMMATORY AND ANTITUMOR 2-OXOTHIAZOLES ABD 2-OXOTHIOPHENES COMPOUNDS

(71) Applicant: Avexxin AS, Trondheim (NO)

(72) Inventors: Berit Johansen, Trondheim (NO); Marcel Sanderberg, Oslo (NO); Inger-Reidun Aukrust, Oslo (NO); George Kokotos, Athens (GR); Efrosini Barbayianni, Athens (GR)

(73) Assignee: Avexxin AS, Trondheim (NO)

( * ) Notice: Subject to any disclaimer, the term of this patent is extended or adjusted under 35 U.S.C. 154(b) by 0 days.

(21) Appl. No.: 15/789,834

(22) Filed: Oct. 20, 2017

(65) Prior Publication Data

US 2018/0105507 A1  Apr. 19, 2018

Related U.S. Application Data

(63) Continuation of application No. 14/764,509, filed as application No. PCT/EP2014/051655 on Jan. 28, 2014, now abandoned.

(60) Provisional application No. 61/775,223, filed on Mar. 8, 2013, provisional application No. 61/775,117, filed on Mar. 8, 2013.

(30) Foreign Application Priority Data

Jan. 29, 2013 (GB) .................................. 1301585.4
Mar. 8, 2013 (GB) .................................. 1304250.2
Jan. 14, 2014 (GB) .................................. 1400579.7

(51) Int. Cl.
| | |
|---|---|
| *C07D 277/56* | (2006.01) |
| *C07D 333/38* | (2006.01) |
| *C07D 277/24* | (2006.01) |
| *A61K 31/381* | (2006.01) |
| *A61K 31/426* | (2006.01) |
| *A61K 31/428* | (2006.01) |
| *A61K 45/06* | (2006.01) |
| *C07D 277/26* | (2006.01) |
| *C07D 277/64* | (2006.01) |

(52) U.S. Cl.
CPC .......... *C07D 333/38* (2013.01); *A61K 31/381* (2013.01); *A61K 31/426* (2013.01); *A61K 31/428* (2013.01); *A61K 45/06* (2013.01); *C07D 277/24* (2013.01); *C07D 277/26* (2013.01); *C07D 277/56* (2013.01); *C07D 277/64* (2013.01)

(58) Field of Classification Search
CPC ................................................... C07D 277/56
See application file for complete search history.

(56) References Cited

U.S. PATENT DOCUMENTS

| | | |
|---|---|---|
| 3,894,152 A | 7/1975 | Pons et al. |
| 4,855,310 A | 8/1989 | Murase et al. |
| 4,902,700 A | 2/1990 | Hayasi et al. |
| 4,908,368 A | 3/1990 | Murase et al. |
| 5,177,215 A | 1/1993 | Murase et al. |
| 5,268,395 A | 12/1993 | Simandl et al. |
| 5,272,986 A | 12/1993 | Smart |
| 5,399,702 A | 3/1995 | Holland et al. |
| 5,569,655 A | 10/1996 | Dority, Jr. et al. |
| 5,569,665 A | 10/1996 | Porter et al. |
| 5,658,909 A | 8/1997 | DeBernardis et al. |

(Continued)

FOREIGN PATENT DOCUMENTS

| | | |
|---|---|---|
| AU | 2006326548 A1 | 6/2007 |
| DE | 2042504 A1 | 4/1971 |

(Continued)

OTHER PUBLICATIONS

Doan et al., The Journal of Clinical Pharmacology, 2005, 45, pp. 751-762. (Year: 2005).*
Golub et al., Science, vol. 286, Oct. 15, 1999, pp. 531-537 (Year: 1999).*
Ahn et al., Novel mechanistic class of fatty acid amide hydrolase inhibitors with remarkable selectivity. Biochemistry. Nov. 13, 2007;46(45):13019-30.
Allevi et al., Enzymatic Resolution of (R)-and (S)-2-(1-Hydroxyalkyl)thiazoles, Synthetic Equivalents of (R)- and (S)-2-Hydroxy Aldehydes. J Org Chem. Jun. 14, 1996;61(12):4144-4147.
Bernard et al., Palladium (0) Catalyzed Nucleophilic Substitution on 2-Cyclopropylidene-Phenoxy Ethanes. Synthetic Communications. 1997;27(5):709-723.

(Continued)

*Primary Examiner* — Laura L Stockton
(74) *Attorney, Agent, or Firm* — McCarter & English, LLP; Steven G. Davis

(57) ABSTRACT

A compound of formula (I)

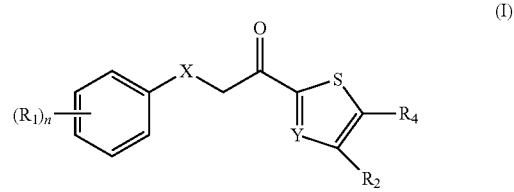

wherein X is O, C=O or S;
Y is N or CH;
$R_2$ and $R_4$ are each independently H, $-(CH_2)_p COOH$, $-(CH_2)_p CON(R^5)_2$ or $-(CH_2)_p COOC_{1-6}alkyl$; or $R_2$ and $R_4$ together form a 6-membered phenyl ring fused to the five membered ring;
each $R_1$ is independently selected from H, halo (e.g. fluoro or chloro), $C_{6-10}$aryl, $C_{7-12}$arylalkyl, $C_{2-12}$ alkenyl; $OC_{1-12}$ alkyl, $OC_{2-12}$ alkenyl or a $C_{1-12}$ alkyl group;
each $R^5$ is H or $C_{1-6}$ alkyl;
each p is 0 to 3;
n is 1 to 4;
or a salt, ester, solvate, N-oxide, or prodrug thereof, e.g. a salt thereof.

7 Claims, 5 Drawing Sheets

(56) References Cited

U.S. PATENT DOCUMENTS

| | | | |
|---|---|---|---|
| 5,693,804 | A | 12/1997 | DeBernardis et al. |
| 6,214,994 | B1 | 4/2001 | DeBernardis et al. |
| 6,462,054 | B1 | 10/2002 | Boger |
| 7,056,917 | B2 | 6/2006 | Nakayama et al. |
| 9,597,318 | B2 | 3/2017 | Kokotos et al. |
| 2003/0055100 | A1 | 3/2003 | Uckun et al. |
| 2003/0130340 | A1 | 7/2003 | Shimada et al. |
| 2004/0041264 | A1 | 3/2004 | Kloster et al. |
| 2005/0137243 | A1 | 6/2005 | Souers et al. |
| 2005/0272036 | A1 | 12/2005 | Barton et al. |
| 2006/0016218 | A1 | 1/2006 | Shapiro et al. |
| 2011/0136879 | A1 | 6/2011 | Kokotos et al. |
| 2015/0066474 | A1 | 3/2015 | Yi et al. |
| 2015/0376161 | A1 | 12/2015 | Johansen et al. |
| 2017/0166539 | A1 | 6/2017 | Kokotos et al. |
| 2017/0166589 | A1 | 6/2017 | Johansen et al. |

FOREIGN PATENT DOCUMENTS

| | | |
|---|---|---|
| DE | 2063901 A1 | 7/1972 |
| EP | 0351194 A2 | 1/1990 |
| EP | 0577003 A1 | 1/1994 |
| EP | 0735029 A1 | 10/1996 |
| EP | 0867437 A1 | 9/1998 |
| EP | 1201268 A2 | 5/2002 |
| EP | 1748044 A1 | 1/2007 |
| EP | 2116530 A1 | 11/2009 |
| GB | 1313150 A | 4/1973 |
| JP | 7-036069 | 2/1995 |
| JP | H11-509835 A | 8/1999 |
| JP | H11-255700 A | 9/1999 |
| JP | 2001-240593 A | 9/2001 |
| JP | 2002-531553 A | 9/2002 |
| JP | 2005-128778 A | 5/2005 |
| JP | 2005-343889 A | 12/2005 |
| JP | 2006-502229 A | 1/2006 |
| JP | 2006-514102 A | 4/2006 |
| JP | 2007-533621 A | 11/2007 |
| JP | 2009-527483 A | 7/2009 |
| WO | 1993/07140 A1 | 4/1993 |
| WO | 1996/03392 A1 | 2/1996 |
| WO | 1996/15792 A1 | 5/1996 |
| WO | 1996/16052 A2 | 5/1996 |
| WO | 1996/036617 A1 | 11/1996 |
| WO | 1996/39399 A1 | 12/1996 |
| WO | 1998/32741 A1 | 7/1998 |
| WO | 2000/09500 A2 | 2/2000 |
| WO | 2000/34254 A1 | 6/2000 |
| WO | 2001/00578 A1 | 1/2001 |
| WO | 2004/016609 A1 | 2/2004 |
| WO | 2004/033652 A2 | 4/2004 |
| WO | 2004/041264 A1 | 5/2004 |
| WO | 2004/041269 A2 | 5/2004 |
| WO | 2005/028456 A1 | 3/2005 |
| WO | 2005/028465 A1 | 3/2005 |
| WO | 2006/016218 A1 | 2/2006 |
| WO | 2006/057503 A1 | 6/2006 |
| WO | 2006/122806 A2 | 11/2006 |
| WO | 2007/061862 A2 | 5/2007 |
| WO | 2007/070514 A1 | 6/2007 |
| WO | 2007/098142 A2 | 8/2007 |
| WO | 2008/013963 A2 | 1/2008 |
| WO | 2008/107335 A1 | 9/2008 |
| WO | 2008/150492 A1 | 12/2008 |
| WO | 2011/039365 A1 | 4/2011 |
| WO | 2012/070420 A1 | 5/2012 |
| WO | 2014/118195 A1 | 8/2014 |
| WO | 2016/016472 A1 | 2/2016 |

OTHER PUBLICATIONS

CAS RN 1097121-81-7, 1,3-Propanedione, 1-(2-benzothiazolyl)-3-(4-methylphenyl)-. 4 pages, Jan. 28, 2009.

Chikashita et al., General Reactivity of 2-Lithiobenzothiazole to Various Electrophiles and the Use as a Formyl Anion Equivalent in the Synthesis of alpha-Hydroxy Carbonyl Compounds. Bull Chem Soc Jpn. Oct. 1988;61:3637-3648.

Costanzo et al., Potent, small-molecule inhibitors of human mast cell tryptase. Antiasthmatic action of a dipeptide-based transition-state analogue containing a benzothiazole ketone. J Med Chem. Aug. 28, 2003;46(18):3865-76.

Evans et al., Enantioselective Friedel-Crafts alkylations catalyzed by bis(oxazolinyl)pyridine-scandium(III) triflate complexes. J Am Chem Soc. Aug. 15, 2007;129(32):10029-41.

Garfunkle et al., Optimization of the central heterocycle of alpha-ketoheterocycle inhibitors of fatty acid amide hydrolase. J Med Chem. Aug. 14, 2008;51(15):4392-403.

Kraus et al., Halogen-Metal Exchange/Cyclization of Iodoketones: A Direct Synthesis of 3-Arylbenzofurans. Synlett. 2005;16:2504-2506.

Marsilje et al., Design, synthesis, and biological evaluation of simplified alpha-keto heterocycle, trifluoromethyl ketone, and formyl substituted folate analogues as potential inhibitors of GAR transformylase and AICAR transformylase. Bioorg Med Chem. Oct. 1, 2003;11(20):4487-501.

Martin et al., Highly efficient borylation Suzuki coupling process for 4-bromo-2-ketothiazoles: straightforward access to micrococcinate and saramycetate esters. Org Lett. Aug. 20, 2009;11(16):3690-3. Supporting Information.

Maryanoff et al., Inhibitors of proteases and amide hydrolases that employ an alpha-ketoheterocycle as a key enabling functionality. Bioorg Med Chem. Feb. 15, 2008;16(4)1562-95.

McGrath et al., Structure-guided design of peptide-based tryptase inhibitors. Biochemistry. May 16, 2006;45 (19):5964-73.

Mete et al., Design of novel and potent cPLA2a inhibitors containing an a-methyl-2-ketothiazole as a metabolically stable serine trap. Bioorg Med Chem Lett. May 15, 2011;21(10):3128-33.

Myllymäki et al., Design, synthesis, and in vitro evaluation of carbamate derivatives of 2-benzoxazolyl- and 2-benzothiazolyl-(3-hydroxyphenyl)-methanones as novel fatty acid amide hydrolase inhibitors. J Med Chem. Aug. 23, 2007;50(17):4236-42.

PubChem CID 9159507, AC1PLZGU, Oct. 8, 2016, 10 pages, PubChem Compound Database; https://pubchem.ncbi.nlm.nih.gov/compound/9159507, create date Jul. 30, 2006.

Reid et al., Notiz Uber Heterocyclisch Substituierte Pyrazoline. European Journal of Inorganic Chemistry. Nov. 1957;90(11):2707-2711.

Ricci et al., Heteroacylsilanes: synthesis and synthetic potentialities of new nucleophilic acylation agents. J Org Chem. Jan. 1985;50(1):130-133.

Schmidt et al., Amino Acids and Peptides; 581 Synthesis of Optically Active 2-(1-Hydroxyalkyl)-thiazole-4-carboxylic Acids and 2-(1-Aminoalkyl)-thiazole-4-carboxylic Acids. Synthesis. 1986;12:992-998.

Sierstad et al., Discovery and development of fatty acid amide hydrolase (FAAH) inhibitors. J Med Chem. Dec. 11, 2008;51(23):7327-43.

STN RN 10471-74-6, 1,3-Propanedione, 1-phenyl-3-(2-thienyl), Nov. 16, 1984, 1 page.

STN RN 1094445-68-7, 1,3-Propanedione, 1-(2-benzothiazolyl)-3-phenyl, Jan. 20, 2009, 1 page.

STN RN 1179358-89-4, 1-Propanone, 3-phenyl-1-(2-thiazolyl), Sep. 2, 2009, 1 page.

STN RN 1347363-73-8, Ethanone, 2-phenoxy-1-[6-(1H-pyrazol-4-yl)-2-benzothiazolyl], Dec. 2, 2011, 1 page.

STN RN 374754-17-3, Ethanone, 2[(3-methoxyphenyl)thio]-1-(2-thiazolyl), Dec. 12, 2001, 1 page.

STN RN 82605-58-1, 1-Propanone, 1,3-bis(2-benzothiazolyl), Nov. 16, 1984, 1 page.

STN RN 882284-72-2, 2-Thiopheneacetic acid, 5-[2-(phenylthio)acetyl], Apr. 30, 2006, 1 page.

STN RN 927974-68-3, 4-Thiazolecarboxylic acid, 2-[2-(4-methylphenoxy)acetyl], Mar. 23, 2007, 1 page.

STN RN 927974-71-8, 4-Thiazolecarboxylic acid, 2-[2-(4-,ethylphenoxy)acetyl], Mar. 23, 2007, 1 page.

STN RN 927974-82-1, 4-Thiazolecarboxylic acid, 2-[2-(2,3-dimethylphenoxy)acetyl], Mar. 23, 2007, 1 page.

(56) References Cited

OTHER PUBLICATIONS

STN RN 927974-85-4, 4-Thiazolecarboxylic acid, 2-[2-(3,4-dimethylphenoxy)acetyl], Mar. 23, 2007, 1 page.
STN RN 927974-91-2, 4-Thiazolecarboxylic acid, 2-[2-(4-methoxyphenoxy)acetyl], Mar. 23, 2007, 1 page.
STN RN 927974-94-5, 4-Thiazolecarboxylic acid, 2-[2-(3-methoxyphenoxy)acetyl], Mar. 23, 2007, 1 page.
STN RN 927974-99-0, 4-Thiazolecarboxylic acid, 2-[2-[4-{1-methylethyl)phenoxyl]acetyl], Mar. 23, 2007, 1 page.
STN RN 927975-03-9, 4-Thiazolecarboxylic acid, 2-[2[2-{1-methylethyl)phenoxylacetyl], Mar. 23, 2007, 1 page.
STN RN 927975-07-3, 4-Thiazolecarboxylic acid, 2-[2-(4-propylphenoxy)acetyl], Mar. 23, 2007, 1 page.
STN RN 927975-11-9, 4-Thiazolecarboxylic acid, 2-[2-[3-methyl-4-(1-methylethyl)phenoxy]acetyl], Mar. 23, 2007, 1 page.
STN RN 927975-13-1, 4-Thiazolecarboxylic acid, 2-[2-[2-(1,1-dimethylethyl)phenoxy]acetyl], Mar. 23, 2007, 1 page.
STN RN 927975-25-5, 4-Thiazolecarboxylic acid, 2-[2-[4-(1,1-dimethylpropyl)phenoxy]acetyl], Mar. 23, 2007, 1 page.
STN RN 927975-29-9, 4-Thiazolecarboxylic acid, 2-[2-[2-(1,1-dimethylethyl)-4, Mar. 23, 2007, 1 page.
STN RN 927975-33-5, 4-Thiazolecarboxylic acid, 2-[2-[4-(1-methyl-1-phenylethyl)phenoxy]acetyl], Mar. 23, 2007, 1 page.
STN RN 927975-39-1, 4-Thiazolecarboxylic acid, 2-[2-([1,1'-biphenyl1-4-yloxy)acetyl), Mar. 23, 2007, 1 page.
STN RN 927975-41-5, 4-Thiazolecarboxylic acid, 2-[2-(2-ethoxyphenoxy)acetyl], Mar. 23, 2007, 1 page.
STN RN 927975-47-1, 4-Thiazolecarboxylic acid, 2-[2-[4-(1,1-dimethylethy)phenoxy]acetyl], Mar. 23, 2007, 1 page.
STN RN 927975-52-8, 4-Thiazolecarboxylic acid, 2-[2-(4-clorophenoxy)acetyl], Mar. 23, 2007, 1 page.
STN RN 927975-54-0, 4-Thiazolecarboxylic acid, 2-(2-phenoxyacetyl), Mar. 23, 2007, 1 page.
STN RN 927975-57-3, 4-Thiazolecarboxylic acid, 2-[2-(2-methylphenoxy)acetyl], Mar. 23, 2007, 1 page.
STN RN 927975-60-8, 4-Thiazolecarboxylic acid, 2-[2-(2-naphthalenyloxy)acetyl], Mar. 23, 2007, 1 page.
STN RN 927975-62-0, 4-Thiazolecarboxylic acid, 2-[2-(3-methylphenoxy)acetyl], Mar. 23, 2007, 1 page.
STN RN 927975-65-3, 4-Thiazoleacetic acid, 2-[2-(4-methylphenoxy)acetyll], Mar. 23, 2007, 1 page.
STN RN 927975-68-6, 4-Thiazoleacetic acid, 2-[2-(4-ethylphenoxy)acetyll], Mar. 23, 2007, 1 page.
STN RN 927979-12-2, 4-Thiazoleacetic acid, 2-[2-(4-methoxyphenoxy)acetyl], Mar. 23, 2007, 1 page.
STN RN 927979-15-5, 4-Thiazoleacetic acid, 2-[2-(3-methoxyphenoxy)acetyl], Mar. 23, 2007, 1 page.
STN RN 927979-21-3, 4-Thiazoleacetic acid, 2-[2-[4-(1-methylethyl)phenoxy]acetyll, Mar. 23, 2007, 1 page.
STN RN 927979-27-9, 4-Thiazoleacetic acid, 2-[2-[2-(1-methylethyl)phenoxy]acetyll, Mar. 23, 2007, 1 page.
STN RN 927979-33-7, 4-Thiazoleacetic acid, 2-[2-(4-propylphenoxy)acetyl), Mar. 23, 2007, 1 page.
STN RN 927979-42-8, 4-Thiazoleacetic acid, 2-(2-(2-(1,1-dimethylethyl)phenoxylacetyl), Mar. 23, 2007, 1 page.
STN RN 927979-60-0, 4-Thiazoleacetic acid, 2-(2-[4-(1,1-dimethylpropyl)phenoxy[acetyl], Mar. 23, 2007.
STN RN 927979-82-6, 4-Thiazoleacetic acid, 2-[2-(2-ethoxyphenoxy)acetyl], Mar. 23, 2007, 1 page.
STN RN 927979-88-2, 4-Thiazoleacetic acid, 2-[2-[4-(1,1-dimethylethyl)phenoxy]acetyll, Mar. 23, 2007, 1 page.
STN RN 927979-96-2, 4-Thiazoleacetic acid, 2-(2-phenoxyacetyl), Mar. 23, 2007, 1 page.
STN RN 927979-98-4, 4-Thiazoleacetic acid, 2-[2-(2-methylphenoxy)acetyl], Mar. 23, 2007, 1 page.
STN RN 927980-00-5, 4-Thiazoleacetic acid, 2-[2-(2-naphthalenyloxy)acetyl], Mar. 23, 2007, 1 page.
STN RN 927980-02-7, 4-Thiazoleacetic acid, 2-[2-(3-methylphenoxy)acetyl], Mar. 23, 2007, 1 page.
Van Uitert et al., Stuides on Coordination Compounds. II. The Dissociation Constants of beta-Diketones in Water-Dioxand Solutions. J Am Chem Soc., Jan. 20, 1953;75(2):455-457.
Vasudevan et al., Heterocyclic ketones as inhibitors of histone deacetylase. Bioorg Med Chem Lett. Nov. 17, 2003;13 (22)3909-13.
Chinese Office Action for Application No. 201080056033.8, dated Mar. 28, 2013. 27 pages.
International Search Report and Written Opinion for Application No. PCT/EP2010/064687, dated Jan. 17, 2011. 15 pages.
International Search Report and Written Opinion for Application No. PCT/EP2015/067836, dated Sep. 23, 2015. 11 pages.
Chen, Potential value and limitation of dual inhibitors of PI3K and mTOR in the treatment of cancer. Curr Cancer Drug Targets. Feb. 2013;13(2):117-20.
Gautam et al., Identification of selective cytotoxic and synthetic lethal drug responses in triple negative breast cancer mils. Mol Cancer. May 10, 2016;15(1):34. 16 pages.
Ge et al., Correction to Synthesis of 3-Substituted Isocoumarins via Cascade Intramolecular Ullmann-Type Coupling-Rearrangement Process. J Org Chem. 2012;77:9435.
Hua et al., AKT and cytosolic phospholipase A2a form a positive loop in prostate cancer cells. Curr Cancer Drug Targets. 2015;15(9):781-91.
Maira et al., Identification and characterization of NVP-BEZ235, a new orally available dual phosphatidylinositol 3-kinase/mammalian target of rapamycin inhibitor with potent in vivo antitumor activity. Mol Cancer Ther. Jul. 2008;7 (7):1851-63.
STN RN 1097121-81-7, 1,3-propanedione, 1-(2-benzothiazolyl)-3-(4-methylphenyl)- 1 pages, (2016).
STN RN 927974-77-4, 4-Thiazolecarboxylic acid, 2-[2-(2,6-dimethylphenoxy)acetyl]- 3 pages, Mar. 23, 2007.
STN RN 927974-88-7, 4-Thiazolecarboxylic acid, 2-[2-(2,4-dimethylphenoxy)acetyl]-, 3 pages, Mar. 23, 2007.
STN RN 941685-85-4, Ethanone, 2-[(4-methoxyphenyl)methoxy]-1-[5-[7-[-[[2-(trimethylsilyl)ethoxy]-7H-pyrrolo [2,3-d]pyrimidin-4-yl]-2-thiazolyl]-, 32 pages, Jul. 9, 2007.
STN RN 927975-49-3, 4-Thiazolecarboxylic acid, 2-[2-(4-chloro-3-methylphenoxy)acetyl]-, 3 pages, Mar. 23, 2007.
STN RN 927975-43-7, 4-THiazolecarboxylic acid, 2-[2-(4-bromo-2,6-dimethylphenoxyl)acetyl]-, 3 pages, Mar. 23, 2007.
Wen et al., Critical role of arachidonic acid-activated mTOR signaling in breast carcinogenesis and angiogenesis. Oncogene. Jan. 10, 2013;32(2)160-70.
International Search Report and Written Opinion for Application No. PCT/EP2017/056016, dated May 19, 2017. 17 pages.
U.S. Appl. No. 14/764,509 Restriction Requirement, dated Mar. 30, 2016. 14 pages.
U.S. Appl. No. 14/764,509 Non-Final Office Action, dated Jul. 1, 2016. 32 pages.
U.S. Appl. No. 14/764,509 Final Office Action, dated Dec. 27, 2016. 23 pages.
U.S. Appl. No. 14/764,509 Non-Final Office Action, dated Jul. 20, 2017. 22 pages.
U.S. Appl. No. 14/764,509 Final Office Action, dated Feb. 9, 2018. 28 pages.

* cited by examiner

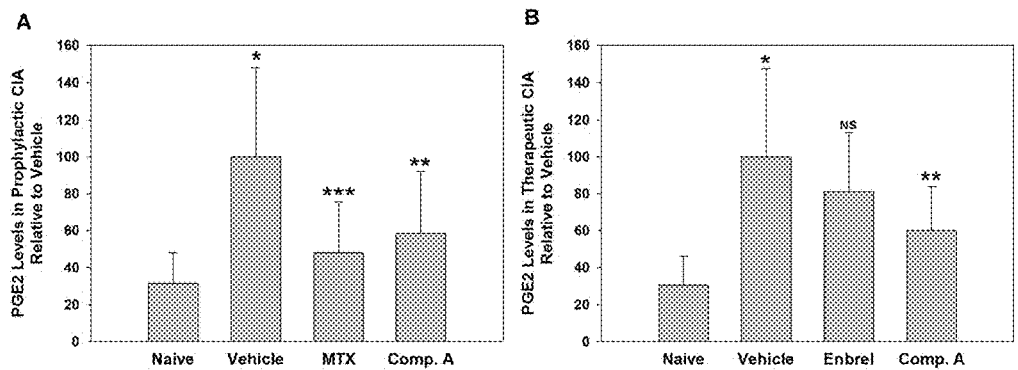
Figure 5A-B.
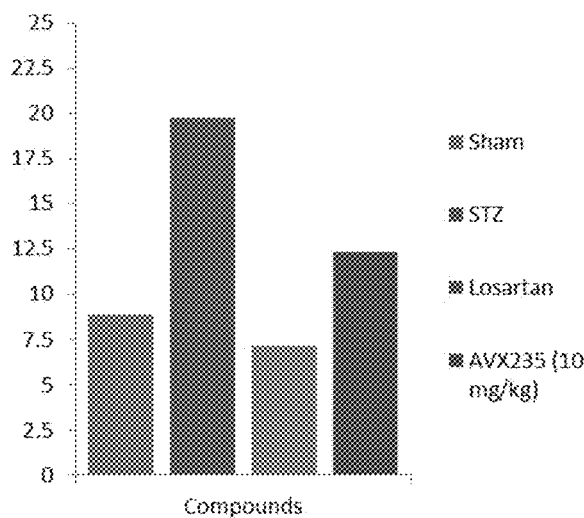
Figure 6

ANTI-INFLAMMATORY AND ANTITUMOR 2-OXOTHIAZOLES ABD 2-OXOTHIOPHENES COMPOUNDS

CROSS-REFERENCES TO RELATED APPLICATIONS

This Application is a Continuation of application Ser. No. 14/764,509 filed on Jul. 29, 2015. Application PCT/EP2014/051655 claims priority from Application 1400579.7 filed on Jan. 14, 2014 in the United Kingdom. Application PCT/EP2014/051655 is a Box VI priority Application 61/775,223 filed on Mar. 8, 2013. Application PCT/EP2014/051655 claims priority from Application 1304250.2 filed on Mar. 8, 2013 in the United Kingdom. Application PCT/EP2014/051655 is a Box VI priority Application 61/775,117 filed on Mar. 8, 2013. Application PCT/EP2014/051655 claims priority from Application 1301585.4 filed on Jan. 29, 2013 in the United Kingdom. The entire contents of these applications are incorporated herein by reference in their entirety.

The invention relates to certain new 2-oxothiazole or 2-oxothiophene compounds and to pharmaceutical compositions comprising said compounds. This invention also relates to the use of various 2-oxothiazole or 2-oxothiophene compounds for use in the prevention, treatment or alleviation of symptoms of chronic inflammatory disorders such as glomerulonephritis, rheumatoid arthritis and psoriasis as well as chronic inflammatory disorders associated with a diabetic condition in a patient, particularly diabetes mellitus, such as diabetic nephropathy and diabetic retinopathy. In another embodiment, this invention relates to the use of various 2-oxothiazole, 2-oxooxazole or 2-oxothiophene compounds for use in the prevention or treatment of hyperproliferative disorders such as cancer.

BACKGROUND

Mammalian cells contain a large number of phospholipases that hydrolyse phospholipids in a structurally specific manner for production of a myriad of products, many of which have potent biological activity. There has been considerable interest in characterising these enzymes because of their role in production of lipid mediators of inflammation. Since the first studies 20 years ago showing that mammalian cells contain a cystolic calcium dependent phospholipase A2 (cPLA2) specific for arachidonic acid, an extensive amount of evidence has substantiated a primary role for $cPLA_2$ as the key enzyme that mediates the release of arachidonic acid for the production of eicosanoids.

The enzyme $cPLA_2$ contributes to the pathogenesis of a variety of diseases particularly those in which inflammation plays a primary role implicating a role for inflammatory lipid mediators in disease pathogenesis. The inhibition therefore of such lipase enzymes offers a potential therapy for inflammatory conditions in particular chronic inflammatory conditions such as those above, psoriasis and glomerulonephritis.

The phospholipase A2s are a group of enzymes that release unsaturated fatty acids from the sn2 position of membrane phospholipids. Once released, the fatty acids are converted by various enzymes into biologically very important signalling molecules. Release of arachidonate initiates the arachidonate cascade leading to the synthesis of eicosanoids such as prostaglandins.

Eicosanoids are important in a variety of physiological processes and play a central role in inflammation. In Inflammation, Vol. 18, No. 1 1994, Andersen et al identify the presence of certain phospholipase A2s in psoriatic human skin.

It is therefore believed that inhibition of phospholipase A2 enzymes should have potential in curing some of the inflammatory symptoms, including epidermal hyperproliferation due to increased leukotriene production, related to eicosanoid production and cell activation in both epidermis and dermis in psoriasis.

Psoriasis is a common, chronic, inflammatory skin disorder. Psoriatic tissue is characterised by chronic inflammation in both epidermis and dermis, the disease being further characterised by hyperplasia of epidermal keratinocytes, fibroblast activation, alteration of eicosanoid metabolism, and leukocyte infiltration.

Glomerulonephritis, also known as glomerular nephritis, abbreviated GN, is a renal disease characterized by inflammation of the glomeruli, or small blood vessels in the kidneys. It may present with isolated hematuria and/or proteinuria or as a nephrotic syndrome, acute renal failure, or chronic renal failure. Glomerulonephritis is categorised into several different pathological patterns, which are broadly grouped into non-proliferative or proliferative types.

The glomerulus is a unique vascular network with three specialised types of cell: the endothelial cell, the mesangial cell and the visceral epithelial cell. Mesangial cells (MC) serve a number of functions in the renal glomerular capillary including structural support of the capillary tuft, modulation of the glomerular hemodynamics and a phagocytic function allowing removal of macromolecules and immune complexes. The proliferation of MC is a prominent feature of glomerular disease including IgA nephropathy, membranoproliferative glomerulonephritis, lupus nephritis, and diabetic nephropathy.

Reduction of MC proliferation in glomerular disease models by treatment with, for example, a low protein diet has been shown to produce extracellular matrix expansion and glomerulosclerotic changes. MC proliferation inhibitors may therefore offer therapeutic opportunities for the treatment of proliferative glomerular disease.

Mesangial proliferative glomerulonephritis is a form of glomerulonephritis which involves inflammation at the kidney glomeruli. The mesangial cells which are a part of the glomerular capillaries, increase in size giving the glomeruli a lumpy appearance. The disorder usually causes nephritic syndrome which represents protein loss in the urine. It may be present as acute, chronic or rapidly progressive glomerulonephritis and may progress to chronic renal failure.

The present inventors seek new treatments for, inter alia, chronic inflammatory conditions such as glomerulonephritis and associated conditions like diabetic nephropathy and retinopathy, psoriasis, dermatitis, rheumatoid arthritis and hyperproliferative disorders such as cancer.

SUMMARY OF THE INVENTION

The present inventors have surprisingly found that certain 2-oxo-thiazoles or 2-oxothiophenes are ideal $cPLA_2$ inhibitors and offer new therapeutic routes to the treatment of chronic inflammatory disorders.

2-oxothiazole type structures are not new. In Bioorganic and Medicinal Chemistry 16 (2008) 1562-1595, there is a review of chemistry in this field. 2-oxo (benz)thiazoles carrying peptides or amino acids on the 2-position (i.e. where the 2-oxo group forms part of the backbone of an amino acid) are known in the art as thrombin inhibitors.

Also reported are certain hydrolase and transferase inhibitors in particular having a 2-oxo-oleyl side chain. Similar compounds as fatty acid amide hydrolase inhibitors are reported in J Med Chem Vol. 51, No. 237329-7343. Their potential as inhibitors of cPLA$_2$ is not discussed.

The compounds claimed herein been identified as exceptional inhibitors of phospholipase A2 enzymes.

In a further aspect, the present inventors have also found that the compounds of the present invention offer value in the prevention or treatment of hyperproliferative disorders (defined below) such as cancer. The inventors have surprisingly found that the compounds of the invention, in particular those of formula (I), have anti-hyperproliferative properties.

Thus, viewed from one aspect the invention provides a compound of formula (I)

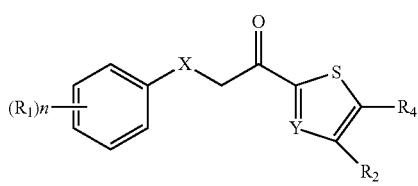

(I)

wherein X is O, C=O or S;
Y is N or CH;
R$_2$ and R$_4$ are each independently H, —(CH$_2$)$_p$COOH, —(CH$_2$)$_p$CON(R$^5$)$_2$ or —(CH$_2$)$_p$COOC$_{1-6}$alkyl; or R$_2$ and R$_4$ together with the atoms linking them form a 6-membered phenyl ring fused to the five membered ring;
each R$_1$ is independently selected from H, halo (e.g. fluoro or chloro), C$_{6-10}$aryl, C$_{7-12}$ arylalkyl, C$_{2-12}$ alkenyl; OC$_{1-12}$ alkyl, OC$_{2-12}$ alkenyl or a C$_{1-12}$ alkyl group;
each R$^5$ is H or C$_{1-6}$ alkyl;
each p is 0 to 3;
n is 1 to 4;
or a salt, ester, solvate, N-oxide, or prodrug thereof, e.g. a salt thereof;
preferably of formula (Ia)

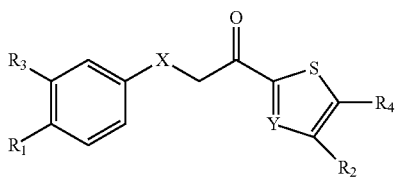

(Ia)

wherein X is O, C=O or S;
Y is N or CH;
R$_2$ and R$_4$ are each independently H, —(CH$_2$)$_p$COOH, —(CH$_2$)$_p$CON(R$^5$)$_2$ or —(CH$_2$)$_p$COOC$_{1-6}$alkyl; or R$_2$ and R$_4$ together with the atoms linking them form a 6-membered phenyl ring fused to the five membered ring;
R$_1$ and R$_3$ are each independently selected from H, halo (e.g. fluoro or chloro), C$_{6-10}$aryl, C$_{7-12}$ arylalkyl, C$_{2-12}$ alkenyl; OC$_{1-12}$ alkyl, OC$_{2-12}$ alkenyl or a C$_{1-12}$ alkyl group;
each R$^5$ is H or C$_{1-6}$ alkyl;
each p is 0 to 3;
or a salt, ester, solvate, N-oxide, or prodrug thereof, e.g. a salt thereof.

Viewed from another aspect the invention provides a pharmaceutical composition comprising a compound of formula (I) as hereinbefore defined.

Viewed from another aspect the invention provides a compound of formula (I) as hereinbefore defined for use in therapy.

Viewed from another aspect the invention provides a compound of formula (I) for use in the treatment of a chronic inflammatory condition.

Viewed from another aspect the invention provides a compound of formula (I) for use in the treatment of a hyperproliferative disorder.

Viewed from another aspect the invention provides a method of treating a chronically inflammatory disorder comprising administering to a patient in need thereof an effective amount of a compound of formula (I) as hereinbefore defined.

Viewed from another aspect the invention provides a method of treating a hyperproliferative disorder comprising administering to a patient in need thereof an effective amount of a compound of formula (I) as hereinbefore defined.

Viewed from a further aspect the invention provides a compound of formula (II)

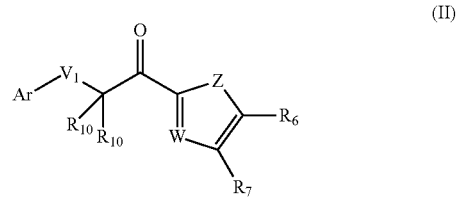

(II)

wherein Z is O or S;
W is N or CH;
R$_6$ is H, C$_{1-6}$alkyl, —(CH$_2$)$_p$COOH, —(CH$_2$)$_p$COOC$_{1-6}$alkyl, —(CH$_2$)$_p$CONH$_2$, —(CH$_2$)$_p$CONHC$_{1-6}$alkyl, —(CH$_2$)$_p$CON(C$_{1-6}$alkyl)$_2$,
R$_7$ is as defined for R$_6$; or
R$_6$ and R$_7$ taken together with the atoms joining them can form a 6-membered aromatic or non aromatic, saturated or unsaturated, carbocyclic or heteroatom containing (e.g. O, N or S containing) ring optionally substituted by up to 4 groups R$_8$;
each R$_8$ is defined as for R$_6$ or is oxo;
R$_{10}$ is the same or different and is H, C$_{1-6}$alkylCOOR$_a$, halo (preferably fluoro), or CHal$_3$ (preferably CF$_3$);
R$_a$ is H or C$_{1-6}$ alkyl;
V$_1$ is O, S, C(=O), —NHCO—, —CONH—, C$_{1-10}$alkylene group, or a C$_{2-10}$-mono or multiply unsaturated alkenylene group, said alkylene or alkenylene group optionally interrupted by C=O and/or one or more heteroatoms selected from O, NH, N(C$_{1-6}$ alkyl), S, SO, or SO$_2$;
Ar is a C$_{6-14}$ aryl group, wherein the aryl group may be optionally substituted (preferably in the meta or para position relative to V$_1$) with one or more R$_9$ groups;
each R$_9$ is halo, OH, CN, nitro, NH$_2$, NHC$_{1-6}$alkyl, N(C$_{1-6}$alkyl)$_2$, haloC$_{1-6}$ alkyl, C$_{6-10}$ aryl group, C$_{7-12}$ arylalkyl, a C$_{1-10}$alkyl group, C$_{2-10}$-mono or multiply unsaturated alkenyl group, OC$_{1-10}$alkyl group, or OC$_{2-10}$-mono or multiply unsaturated alkenyl group;
each p is 0 to 3;
or a salt, ester, solvate, N-oxide, or prodrug thereof;
for use in the treatment of hyperproliferative disorders.

Viewed from another aspect the invention provides a compound of formula (XX)

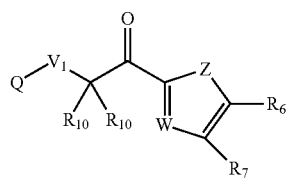

(XX)

wherein Z is O or S;
W is N or CH;
$R_6$ is H, $C_{1-6}$alkyl, $-(CH_2)_p COOH$, $-(CH_2)_p COOC_{1-6}$alkyl, $-(CH_2)_p CONH_2$, $-(CH_2)_p CONHC_{1-6}$alkyl, $-(CH_2)_p CON(C_{1-6}$alkyl$)_2$,
$R_7$ is as defined for $R_6$; or
$R_6$ and $R_7$ taken together with the atoms joining them can form a 6-membered aromatic or non aromatic, saturated or unsaturated, carbocyclic or heteroatom containing (e.g. O, N or S containing) ring optionally substituted by up to 4 groups $R_8$;
each $R_8$ is defined as for $R_6$ or is oxo;
$R_{10}$ is the same or different and is H, $C_{1-6}$alkyl$COOR_a$, halo (preferably fluoro), or $CHal_3$ (preferably $CF_3$);
$R_a$ is H or $C_{1-6}$ alkyl;
$V_1$ is O, S, C(=O), —NHCO—, —CONH—, $C_{1-10}$alkylene group, or a $C_{2-10}$-mono or multiply unsaturated alkenylene group, said alkylene or alkenylene group optionally interrupted by C=O and/or one or more heteroatoms selected from O, NH, N($C_{1-6}$ alkyl), S, SO, or $SO_2$;
Q is $C_{1-20}$ alkyl or Ar wherein
Ar is a $C_{6-14}$ aryl group, wherein the aryl group may be optionally substituted (preferably in the meta or para position relative to $V_1$) with one or more $R_9$ groups;
each $R_9$ is halo, OH, CN, nitro, $NH_2$, $NHC_{1-6}$alkyl, $N(C_{1-6}$alkyl$)_2$, halo$C_{1-6}$alkyl, $C_{6-10}$ aryl group, $C_{7-12}$ arylalkyl, a $C_{1-10}$alkyl group, $C_{2-10}$-mono or multiply unsaturated alkenyl group, $OC_{1-10}$alkyl group, or $OC_{2-10}$-mono or multiply unsaturated alkenyl group;
each p is 0 to 3;
or a salt, ester, solvate, N-oxide, or prodrug thereof;
for use in the treatment of hyperproliferative disorders.

Viewed from another aspect the invention provides a method of treating a hyperproliferative disorder comprising administering to a patient an effective amount of a compound of formula (II) or (XX) as hereinbefore defined.

Viewed from another aspect the invention provides a compound of formula (XXI)

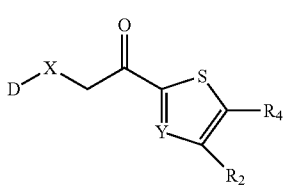

(XXI)

wherein
wherein X is O, C=O or S;
Y is N or CH;
$R_2$ and $R_4$ are each independently H, $-(CH_2)_p COOH$, $-(CH_2)_p CON(R^5)_2$ or $-(CH_2)_p COOC_{1-6}$alkyl; or $R_2$ and $R_4$ together with the atoms linking them form a 6-membered phenyl ring fused to the five membered ring;
D is a $C_{1-20}$ alkyl group;
each $R^5$ is H or $C_{1-6}$ alkyl;
each p is 0 to 3;
or a salt, ester, solvate, N-oxide, or prodrug thereof, e.g. a salt thereof;

BRIEF DESCRIPTION OF THE DRAWINGS

FIG. 5A-B are graphs showing that Compound A reduces disease-induced PGE2 accumulation, suggesting that the compound is hitting its cellular target the cPLA2 enzyme. A) In the prophylactic CIA study (n=11), Compound A (7.5 mg/kg) significantly reduced plasma $PGE_2$ levels, comparable to the effect of metothrexate (MTX) (0.3 mg/kg). B) In the therapeutic CIA study (n=10), Compound A (30 mg/kg) significantly reduced plasma $PGE_2$ levels in the therapeutic CIA mice, whereas Enbrel (25 mg/kg) show no reduction in $PGE_2$ levels. *p<0.001 vs Naïve, NS—not significant, p<0.03 and *p<0.004 vs Vehicle, error bars denote standard deviation.

FIG. 6 shows the therapeutic effect of AVX235 in the rat streptozocin-induced model of human chronic renal disease and compared against losartan (positive control).

DEFINITIONS

Figure 1:
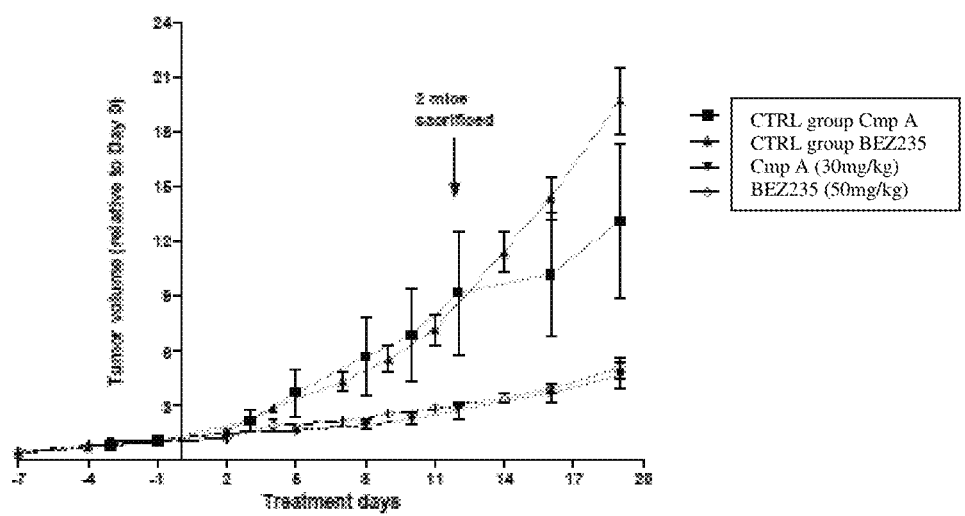
FIG. 1 is a graph showing results from an animal tumor model in which tumor volumes are reduced in the presence of BEZ235 (Novartis Pharma) and Compound A.

In this specification, unless stated otherwise, the term "alkyl" includes both straight and branched chain alkyl radicals and may be methyl, ethyl, n-propyl, i-propyl, n-butyl, i-butyl, s-butyl, t-butyl, n-pentyl, i-pentyl, t-pentyl, neo-pentyl, n-hexyl or i-hexyl, t-hexyl.

The term "alkenyl" includes both straight and branched chain alkenyl radicals. The term alkenyl refers to an alkenyl radicals one or more double bonds and may be, but is not limited to vinyl, allyl, propenyl, i-propenyl, butenyl, i-butenyl, crotyl, pentenyl, i-pentenyl and hexenyl.

The term "aryl" refers to an optionally substituted monocyclic or bicyclic hydrocarbon ring system containing at least one unsaturated aromatic ring. Examples and suitable values of the term "aryl" are phenyl, naphtyl, 1,2,3,4-tetrahydronaphthyl, indyl, indenyl and the like.

The term arylalkyl covers aryl groups substituted with alkyl groups. The arylalkyl may bind to the carbon atom to which it is attached via the aryl ring or via a carbon of an alkyl substituent such as in benzyl.

In the definition of $V_1$ said alkylene or alkenylene group can be optionally interrupted by C=O and/or one or more heteroatoms selected from O, NH, N($C_{1-6}$ alkyl), S, SO, or $SO_2$. The CO and/or heteroatoms can be in the middle of an alkylene or alkenylene chain or can be present at the ends of the alkylene or alkenylene chain. Thus alkylene interrupted by O includes the linkers —OCH$_2$—, —CH$_2$O— and —CH$_2$—O—CH$_2$— and so on.

Halo refers to fluoro, chloro, bromo or iodo, especially chloro or fluoro.

DETAILED DESCRIPTION OF INVENTION

Compounds of Formula (I)

In a first embodiment, the invention provides 2-oxothiazole and 2-oxothiophene compounds of formula (I)

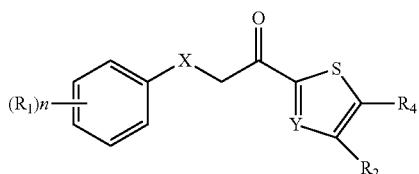
(I)

preferably of formula (Ia)

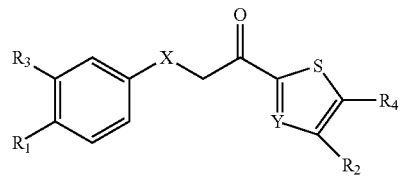
(Ia)

wherein X is O, C=O or S;
Y is N or CH;
$R_2$ and $R_4$ are each independently H, —(CH$_2$)$_p$COOH, —(CH$_2$)$_p$CON($R^5$)$_2$ or —(CH$_2$)$_p$COOC$_{1-6}$alkyl; or $R_2$ and $R_4$ together form a 6-membered phenyl ring fused to the five membered ring
$R^1$ and $R_3$ are each independently selected from H, halo (e.g. fluoro or chloro), $C_{6-10}$aryl, $C_{7-12}$ arylalkyl, $C_{2-12}$ alkenyl; $OC_{1-12}$ alkyl, $OC_{2-12}$ alkenyl or a $C_{1-12}$alkyl group;
each $R^5$ is H or $C_{1-6}$ alkyl;
each p is 0 to 3;
n is 1 to 4;
or a salt, ester, solvate, N-oxide, or prodrug thereof, e.g. a salt thereof.

It is preferred if Y is N and the ring system is a thiazole system.

It is preferred if X is O.

It is preferred if p is 0.

It is preferred if at least one of $R_2$ or $R_4$ is H. It is preferred if both $R_2$ or $R_4$ are not H.

It is preferred if one of $R^2$ or $R^4$ is H and the other is —COOCH$_3$ or —COOCH$_2$CH$_3$. $R_2$ is preferably —COOCH$_3$ or —COOCH$_2$CH$_3$.

Preferably, $R_4$ is H.

In compounds of formula (I) n is preferably 1 or 2. Moreover, it is preferred if the substituents are positioned on adjacent carbon atoms, ideally the meta and para positions on the ring. Preferred options for $R_1$ are a $C_{4-10}$alkyl group, especially a $C_{6-8}$ alkyl group such as a $C_8$ alkyl group, a $C_{4-10}$ alkenyl group, a $OC_{1-10}$ alkyl group, $C_{7-12}$ arylalkyl or a $C_{6-10}$ aryl group. $R_1$ or $R_3$ alkyl groups are preferably linear.

In compounds (Ia), it is preferred if one of $R_1$ and $R_3$, most preferably $R_1$, is a $C_{4-10}$alkyl group, especially a $C_{6-8}$ alkyl groups such as a $C_8$ alkyl group or a $C_{6-10}$ aryl group. $R_1$ and $R_3$ are preferably different.

It is preferred if both $R_1$ and $R_3$ are not H.

It is preferred if one of $R_1$ and $R_3$ is a $C_{4-10}$alkyl group, $C_{2-10}$ alkenyl group or —$OC_{4-10}$ alkyl group and the other is H, halo or $OC_{1-6}$ alkyl.

$R_3$ is preferably H, halo or $OC_{1-6}$ alkyl.

Where $R_1$ or $R_3$ is alkenyl, it preferably contains one double bond. Ideally that double bond is on the two carbons nearest the Ar group.

In a further preferred embodiment the invention provides a compound of formula (IX):

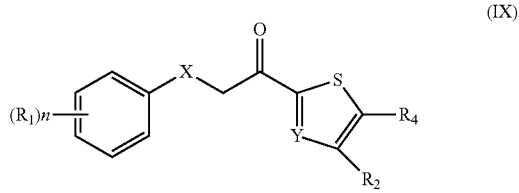
(IX)

wherein X is O, C=O or S;
Y is N or CH;
$R_2$ and $R_4$ are each independently H, —(CH$_2$)$_p$COOH or —(CH$_2$)$_p$COOC$_{1-6}$alkyl; or $R_2$ and $R_4$ together with the atoms linking them form a 6-membered phenyl ring fused to the five membered ring
n is 2;
one $R_1$ is H, Hal, or $OC_{1-6}$ alkyl;
one $R_1$ is H, $C_{6-10}$aryl, $C_{7-12}$ arylalkyl, $C_{2-10}$ alkenyl; $OC_{4-10}$ alkyl or a $C_{4-10}$ alkyl group;
each p is 0 to 2;
or a salt, ester, solvate, N-oxide, or prodrug thereof, e.g. a salt thereof.

In a further preferred embodiment therefore, the invention provides a compound of formula (X)

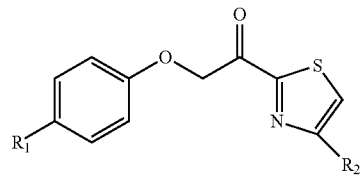
(X)

wherein R₂ is COOH or COOC$_{1-6}$alkyl; R$_1$ is a C$_{4-10}$alkyl group, OC$_{4-10}$alkyl, C$_{4-10}$ alkenyl, C$_{7-12}$ arylalkyl or C$_{6-10}$-aryl group;

or a salt, ester, solvate, N-oxide, or prodrug thereof;
or a compound of formula (XI)

(XI)

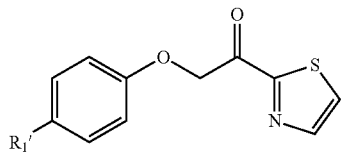

R$_{1'}$ is H, Hal, e.g. F, C$_{7-12}$ arylalkyl or C$_{6-10}$-aryl group;
or a salt, ester, solvate, N-oxide, or prodrug thereof;

In a further preferred embodiment therefore, the invention provides a compound of formula (III)

(III)

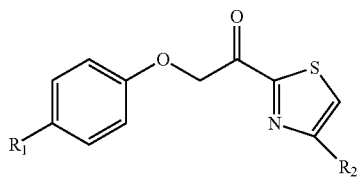

wherein R$_2$ is COOH or COOC$_{1-6}$alkyl;
R$_1$ is a C$_{4-10}$alkyl group, or C$_{6-10}$-aryl group;
or a salt, ester, solvate, N-oxide, or prodrug thereof;
or a compound of formula (IV)

(IV)

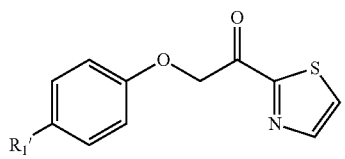

R$_{1'}$ is a C$_{6-10}$-aryl group;
or a salt, ester, solvate, N-oxide, or prodrug thereof.

In these compounds, if R$_1$ is an alkyl, it is preferably linear.

In formula (III) it is preferred if R$_2$ is —COOCH$_3$ or —COOCH$_2$CH$_3$.

In formula (III) it is preferred if R$_1$ is a C$_{6-10}$alkyl group, especially a C8 alkyl group.

It is preferred if R$_{1'}$ is Ph.

In a highly preferred embodiment, the compound of formula (I) is selected from the following compounds:

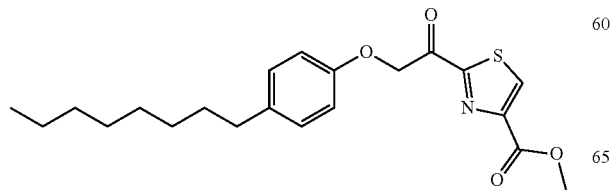

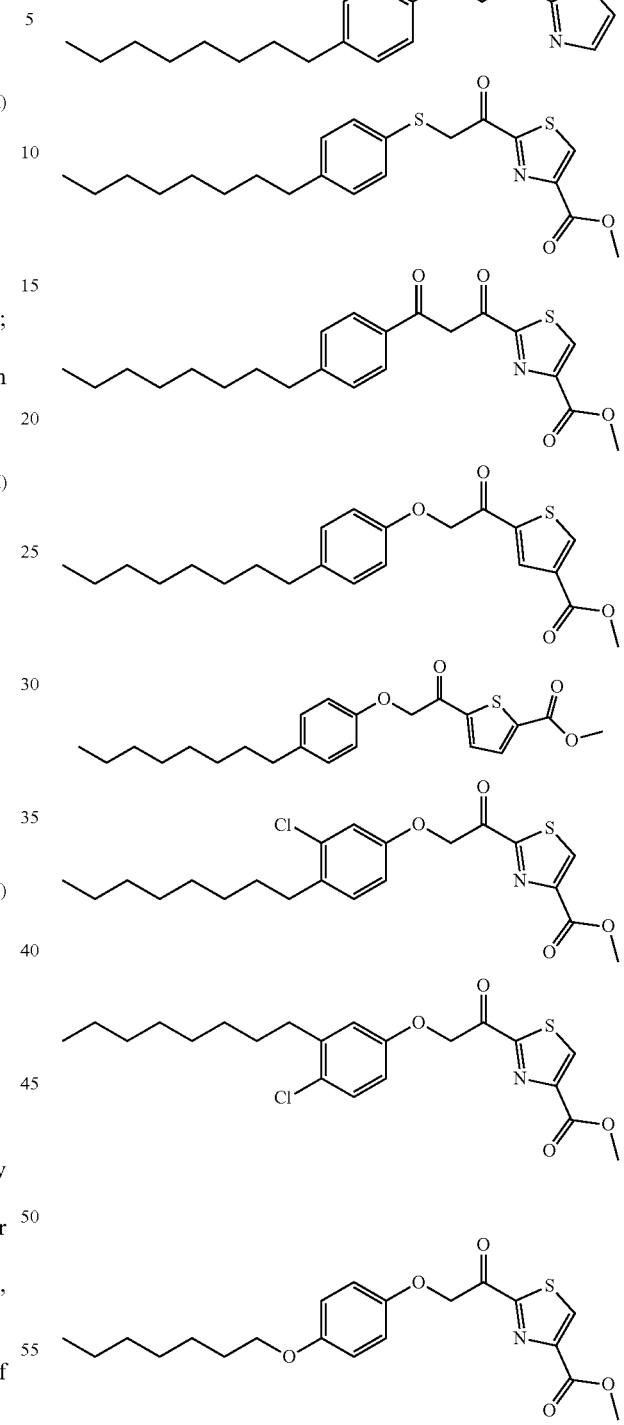

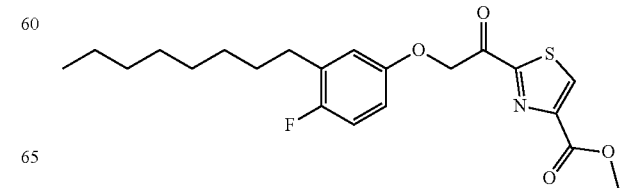

-continued

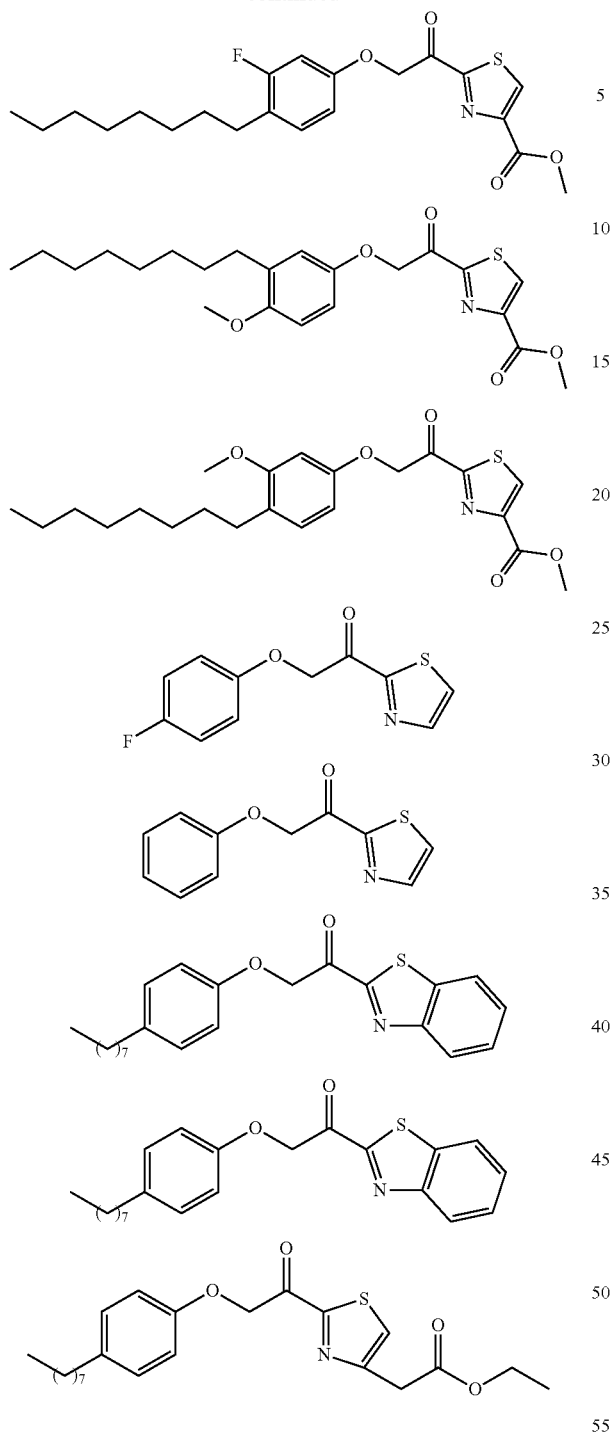

The use of the following compounds is especially preferred.

Compound A

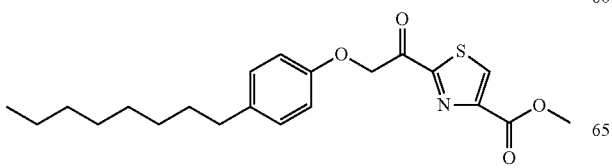

-continued

Compound B

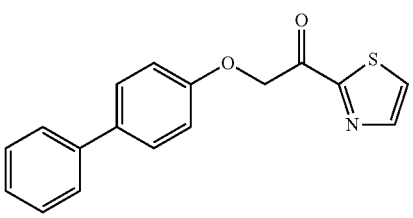

Further compounds of interest are:

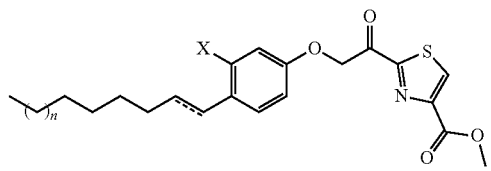

P1$_{a,b}$: (n = 1, X = F,
----  is a single (P1$_a$) or double bond (P1$_b$)
P2$_{a,b}$: (n = 1, X = Cl,
----  is a single (P2$_a$) or double bond (P2$_b$)bond)
P3$_{a,b}$: (n = 1, X = OMe,
----  is a single (P3$_a$) or double bond (P3$_b$)bond)

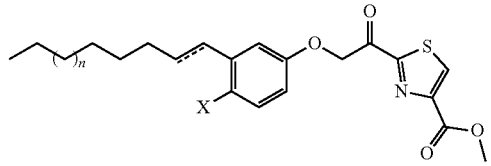

Q1$_{a,b}$: (n = 1, X = F,
----  is a single (Q1$_a$) or double bond (Q1$_b$)bond
Q2$_{a,b}$: (n = 1, X = Cl,
----  is a single (Q2$_a$) or double bond (Q2$_b$)bond
Q3$_{a,b}$: (n = 1, X = OMe,
----  is a single (Q3$_a$) double (Q3$_b$)bond

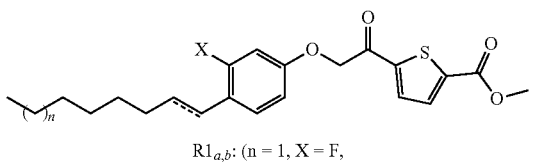

R1$_{a,b}$: (n = 1, X = F,
----  is a single (R1$_a$) or double (R1$_b$)bond
R2$_{a,b}$: (n = 1, X = Cl,
----  is a single (R2$_a$) (R2$_b$) or double bond
R3$_{a,b}$: (n = 1, X = OMe,
----  is a single (R3$_a$) or double (R3$_b$) bond Compound S1-S3

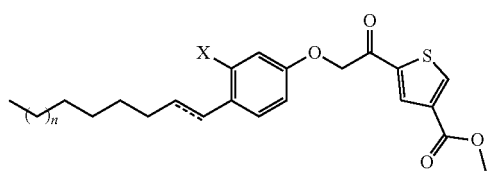

S1$_{a,b}$: (n = 1, X = F,
----  is a single (S1$_a$) or double (S1$_b$)bond
S2$_{a,b}$: (n = 1, X = Cl,
----  is a single (S2$_a$) (S2$_b$) or double bond
S3$_{a,b}$: (n = 1, X = OMe,
----  is a single (S3$_a$) or double (S3$_b$) bond -continued

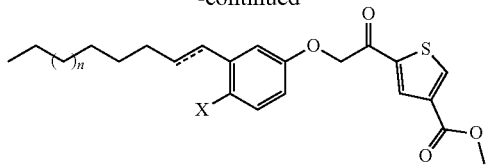

T1$_{a,b}$: (n = 1, X = F,
----- is a single (T1$_a$) or double (T1$_b$) bond
T2$_{a,b}$: (n = 1, X = Cl,
----- is a single (T2$_a$) (T2$_b$) or double bond
T3$_{a,b}$: (n = 1, X = OMe,
----- is a single (T3$_a$) or double (T3$_b$) bond The invention extends to salts, esters, solvates, N-oxides or prodrugs of the compounds identified above In a preferred embodiment, the compound of formula (I) is not

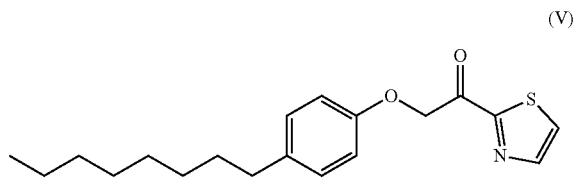 [SMILES: CCCCCCCCc1ccc(OCC(=O)c2nccs2)cc1]

(V)

The invention relates to compounds of Formula (I) per se, pharmaceutical compositions comprising said compounds and the compounds for use in therapy and for use in the prevention and treatment of chronic inflammatory disorders and hyperproliferative disorders. Ideally the compound is not of formula (V).

Compounds of Formula (II)

Viewed from a further aspect the invention provides a compound of formula (II) for use in the prevention or treatment of hyperproliferaitve disorders. Compounds of formula (II) have the following structure:

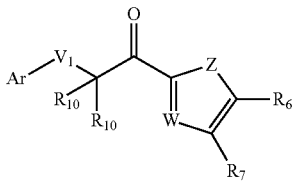

(II)

wherein Z is O or S;
W is N or CH;
$R_6$ is H, $C_{1-6}$alkyl, —(CH$_2$)$_p$COOH, —(CH$_2$)$_p$COOC$_{1-6}$alkyl, —(CH$_2$)$_p$CONH$_2$, —(CH$_2$)$_p$CONHC$_{1-6}$alkyl, —(CH$_2$)$_p$CON(C$_{1-6}$alkyl)$_2$,
$R_7$ is as defined for $R_6$; or
$R_6$ and $R_7$ taken together with the atoms joining them can form a 6-membered aromatic or non aromatic, saturated or unsaturated, carbocyclic or heteroatom containing (e.g. O, N or S containing) ring optionally substituted by up to 4 groups $R_8$;
each $R_8$ is defined as for $R_6$ or is oxo;
$R_{10}$ is the same or different and is H, $C_{1-6}$alkylCOOR$_a$ where $R_a$ is H or $C_{1-6}$ alkyl, halo (preferably fluoro), or CHal$_3$ (preferably CF$_3$);

$V_1$ is O, S, C(=O), —NHCO—, —CONH—, $C_{1-10}$alkylene group, or a $C_{2-10}$-mono or multiply unsaturated alkenylene group, said alkylene or alkenylene group optionally containing C=O and/or one or more heteroatoms selected from O, NH, N(C$_{1-6}$ alkyl), S, SO, or SO$_2$;

Ar is a $C_{6-14}$ aryl group, wherein said aryl group may be optionally substituted (preferably in the meta or para position relative to $V_1$) with one or more $R_9$ groups;

each $R_9$ is halo, OH, CN, nitro, NH$_2$, NHC$_{1-6}$alkyl, N(C$_{1-6}$alkyl)$_2$, haloC$_{1-6}$alkyl, C$_{6-10}$ aryl group, C$_{7-12}$ arylalkyl, a $C_{1-10}$alkyl group, C$_{2-10}$-mono or multiply unsaturated alkenyl group, OC$_{1-10}$alkyl group, or OC$_{2-10}$-mono or multiply unsaturated alkenyl group;

each p is 0 to 3;
or a salt, ester, solvate, N-oxide, or prodrug thereof.

It is preferred if Z is S. The use of thiazole or thiophene rings is therefore preferred.

It is preferred if W is N. The use therefore of a thiazole ring is preferred.

It is preferred if at least one $R_{10}$ is H. It is preferred if both $R_{10}$ groups are H.

If not H, it is preferred that one $R_{10}$ is halo, e.g. F.

It is preferred if $R_6$ and $R_7$ are each independently H, —(CH$_2$)$_p$COOH, or —(CH$_2$)$_p$COOC$_{1-6}$alkyl, where p is 0 to 3, such as 0-2. Most preferably, $R_6$ is H and $R_7$ is H, —COOCH$_3$ or —COOCH$_2$CH$_3$. It is preferred if p is 0.

It is preferred if one of $R_6$ or $R_7$ is H and the other is —COOCH$_3$ or —COOCH$_2$CH$_3$. $R_7$ is preferably —COOCH$_3$ or —COOCH$_2$CH$_3$. $R_6$ is preferably H.

Where $R_6$ and $R_7$ together form a ring, that is preferably a phenyl ring. Ideally such a ring is unsubstituted, i.e. $R_8$ is H.

$V_1$ is preferably O, S or CO or is a $C_{1-6}$ alkylene group (e.g. $C_{2-4}$ alkylene) optionally interrupted by one or more of C=O, O or NH, such as —O— or —CONH—. The $V_1$ linker can therefore be an alkylene linker or an alkoxide type linker of formula —O(CH$_2$)$_q$— where q is 1 to 6. It is preferred of the O atom binds to the Ar group.

In a most preferred embodiment, $V_1$ is —O—. Alternatively, the $V_1$ linker might contain an amide linkage —CONH—.

Ar is preferably a $C_{6-10}$aryl group, especially a phenyl group or naphthyl group. The Ar group can be unsubstituted. It is preferred, however, if the Ar group is substituted with at least one $R_9$ group. Ideally there are one or two $R_9$ groups present.

$R_9$ is preferably halo (e.g. Cl or F), —OC$_{1-10}$alkyl group, $C_{6-10}$ aryl, $C_{7-12}$ arylalkyl, $C_{2-10}$ alkenyl group or a —C$_{1-10}$alkyl group. It is particularly preferred if the $C_{2-10}$alkyl group is a $C_{6-10}$alkyl group, especially a $C_8$ alkyl group. $R_9$ alkyl groups are preferably linear. $R_9$ substituents are preferably meta or para to the $V_1$ linker. If two $R^9$ groups are present, they are preferably on adjacent carbon atoms.

Further preferred compounds of formula (II) are therefore those of formula (VI)

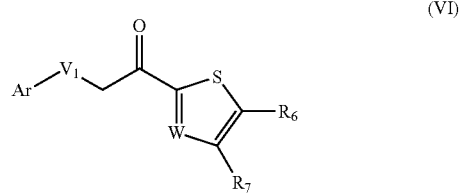

(VI)

wherein W is N or CH;

R₆ is H, —(CH₂)$_p$COOH, or —(CH₂)$_p$COOC$_{1-6}$alkyl,

R₇ is as defined for R₆; or

R₆ and R₇ taken together with the atoms joining them can form a 6-membered aromatic or non aromatic, saturated or unsaturated, carbocyclic or heteroatom containing (e.g. O, N or S containing) ring;

V₁ is O, S, C(=O), or C$_{1-10}$alkylene group, said alkylene group being optionally interrupted by C=O and/or one or more heteroatoms selected from O or NH;

Ar is a C$_{6-14}$ aryl group, wherein aryl group may be optionally substituted (preferably in the meta or para position relative to V₁) with one or two R₉ groups;

each R₉ is halo, C$_{6-10}$ aryl group, C$_{7-12}$ arylalkyl, a C$_{1-10}$alkyl group, C$_{2-10}$-mono or multiply unsaturated alkenyl group, OC$_{1-10}$alkyl group, or OC$_{2-10}$-mono or multiply unsaturated alkenyl group; and each p is 0 to 3;

or a salt, ester, solvate, N-oxide, or prodrug thereof.

In one embodiment, compounds of formula (II) are not of formula (V) as hereinbefore defined. Preferred compounds of formula (II) are those of formula (III), (IV), (IX), (X) and (XI).

Interesting compounds of formula (II) are those listed above which are also within the scope of formula (I) and the following compounds:

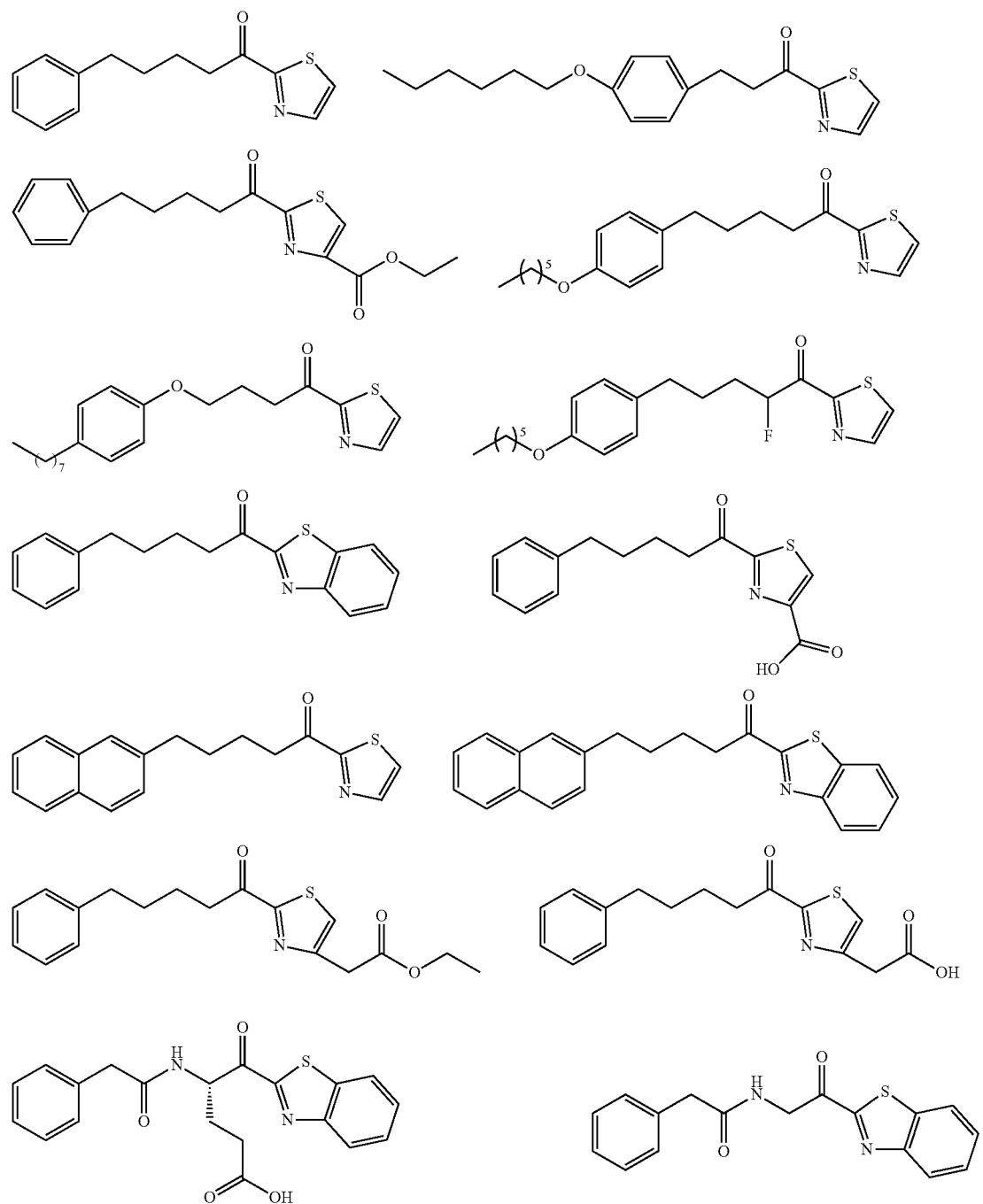

-continued
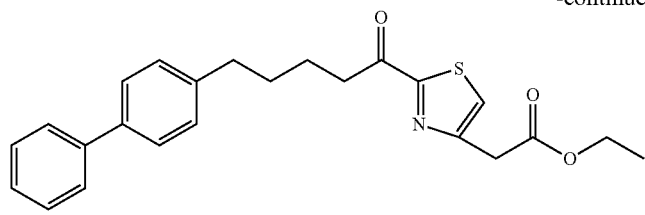
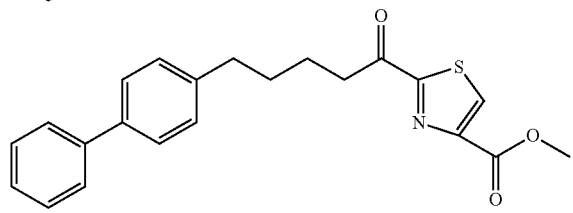
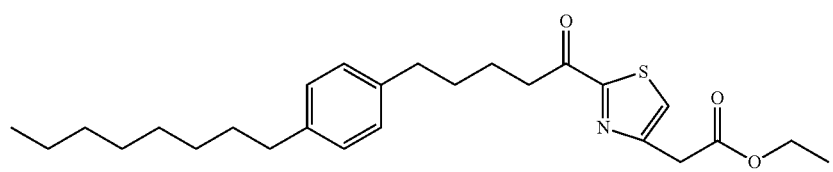
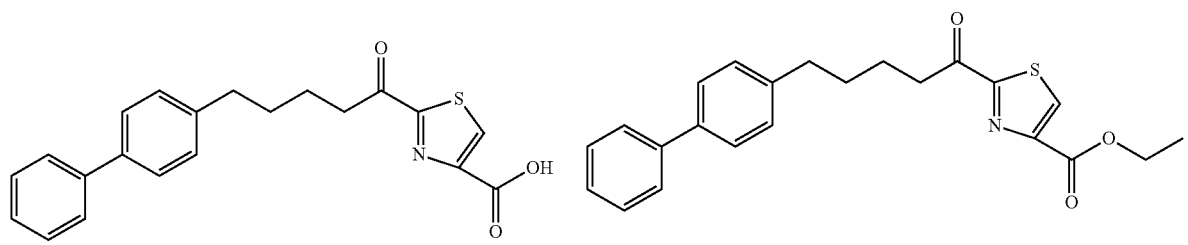
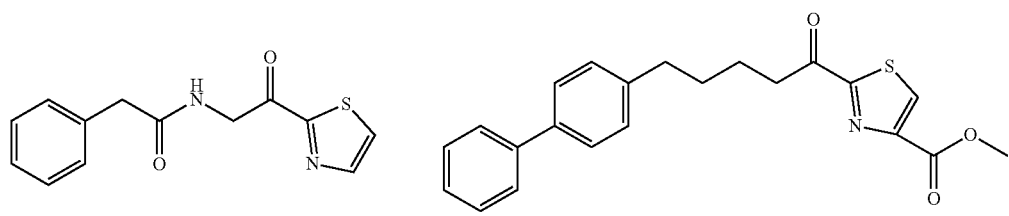
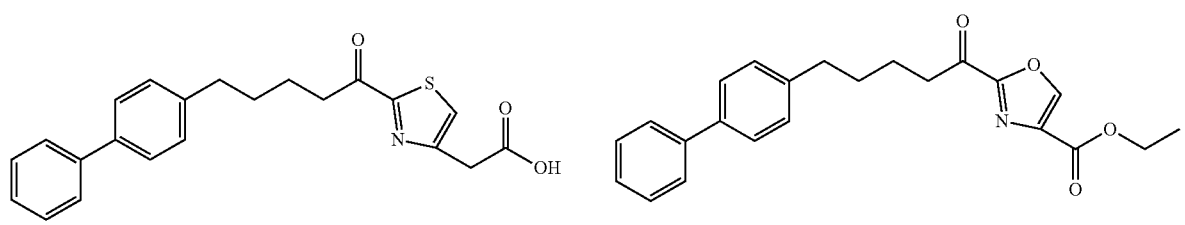
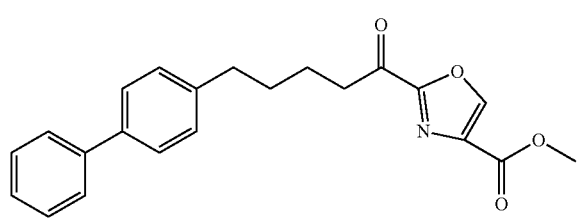
Compounds of formula (XX) are particularly suited for the treatment of hyperproliferative disorders. In compounds of formula (XX) Q is preferably C3-15 alkyl, such as C8-12 alkyl. Q is preferably linear alkyl. The other variables are preferably as defined for compounds of formula (II) defined above.

Compounds of formula (XXI) may be used for the treatment of chronic inflammatory conditions and hyperproliferative conditions. In such compounds, D is preferably C1-15 alkyl, such as C8-12 alkyl. D is preferably linear alkyl. Other variables are as for compounds of formula (I) defined above. Particularly interesting compounds are therefore:

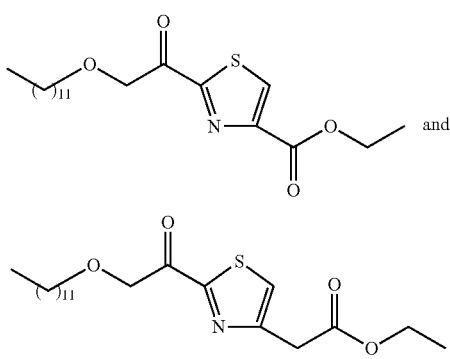

Synthesis

The manufacture of the compounds of the invention typically involves known literature reactions. For example, the formation of an 2-oxothiazole, the precursor to many of the claimed compounds, can be achieved by reaction of an aldehyde XCOH with thiazole in the presence of a base and subsequent oxidation of the hydroxyl to a ketone. The X group is obviously selected to form the desired $M_1V_1$ group or a precursor thereof.

These reactions are summarized in Scheme 1 below.

Scheme 1. (a) thiazole, base; (b) oxidation, e.g. Dess-Martin periodinane.

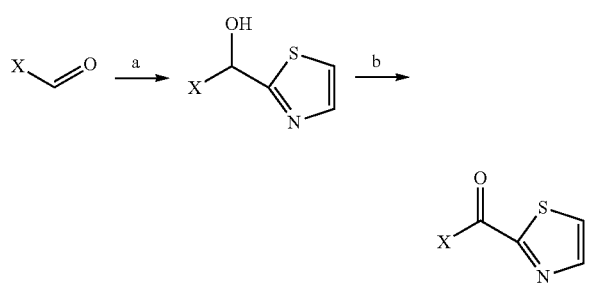

It will be appreciated that in the scheme above and many of those below, specific reagents and solvents may mentioned to aid the skilled man in carrying out the reactions described. The skilled man will appreciate however that a variety of different conditions, reagents, solvents, reactions etc could be used to effect the chemistry described and the conditions quoted are not intended to be limiting on the reactions described.

An alternative strategy involves the reaction of an alkoxy amide XCON(Oalkyl) with thiazole in base which affords 2-oxothiazoles directly. This reaction is summarised in scheme 2.

Scheme 2. (a) thiazole, base.

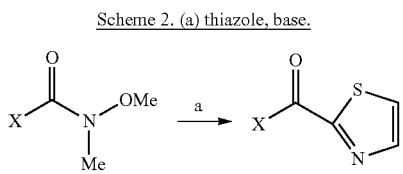

There are still further ways of developing a 2-oxo thiazole ring carrying a substituent. The ring itself can be generated from a thioamide as described in scheme 3.

Scheme 3. (a) TBDMSCN, KCN; (b) $H_2O_2$, $Bu_4NHSO_4$; (c) Lawesson's reagent; (d) $BrCH_2COCOOEt$; (e) Dess Martin periodinane.

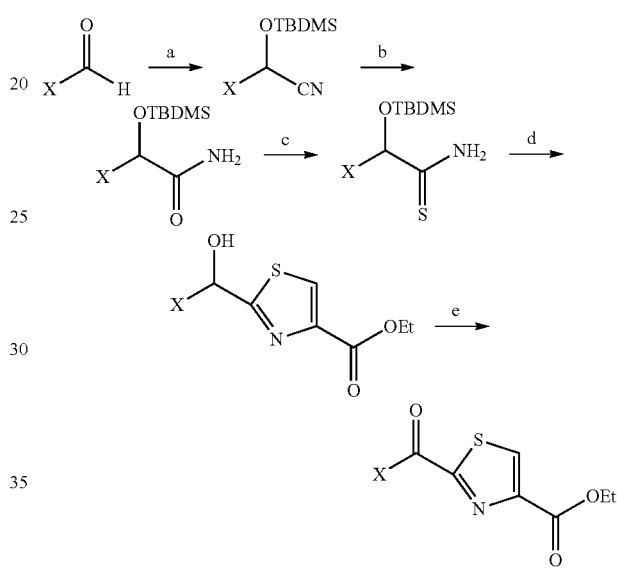

The formed compound can react with thiazole as described above. Variations of the substituents on the heterocyclic rings and manipulation of the side chain binding the carbonyl can be achieved using all manner of synthetic techniques which the skilled man will know. Guidance is offered in the examples as to how to make a wide variety of compounds and the principles described can be extended to the compounds encompassed by the claims. WO2011/039365 also offers synthetic pathways to follow.

The principles described above for preparing thiazoles can be extended to the thiophene and oxazole species.

Chronic Inflammatory Disorders

The compounds of formula (I) of the invention may be used in the prevention or treatment of chronic inflammatory disorders, in particular those associated with phospholipase inhibition.

Preferably, any compound of formula (I) of the invention will achieve at least 75%, such as at least 90% inhibition against group IVa $PLA_2$.

Preferably, compounds of formula (I) of the invention inhibit group IVa $cPLA_2$ at a low μM range such as 5 μM or less, preferably 4 μM or less.

It is further preferred that the compounds of formula (I) of the invention show greater inhibition of group IVa $cPLA_2$ than $iPLA_2$ or $sPLA_2$ according to published assays for these enzymes (see, for example, Yang, H et al. (1999) *Anal. Biochem.* 269: 278). Ideally, the compounds of formula (I)

of the invention show limited or no inhibition of iPLA$_2$ or sPLA$_2$ and they are therefore highly specific for the group IVa cPLA$_2$ enzyme.

Specific diseases of interest are glomerulonephritis, inflammatory dermatoses such as psoriasis and rheumatoid arthritis.

Further conditions of interest include other inflammatory dermatoses such as atopic dermatitis, allergic contact dermatitis, seborrheic dermatitis, pityriasis rosea, lichen planus and drug eruptions.

Furthermore the compounds of formula (I) of the invention may have use in the treatment of other types of arthritis and dermatoses, inflammatory CNS diseases, multiple sclerosis, chronic obstructive pulmonary disease, chronic lung inflammatory conditions, inflammatory bowel disease such as ulcerative colitis and crohns disease, and cardiovascular disease. Furthermore, the compounds of formula (I) of the invention may have use in the treatment of juvenile arthritis, Crohn's colitis, psoriatic arthritis and ankylosing spondylitis.

Thus viewed from a further aspect the invention provides for the management (typically an alleviation of symptoms), prevention or treatment of any of the conditions listed above using the compounds of formula (I) of the invention.

In one embodiment, the prevention, treatment, or alleviation of symptoms of a chronic inflammatory condition such as those mentioned above can be achieved by administering at least one compound according to formula (I) (e.g., one, two or three of such compounds) to a subject as the sole active agent. Alternatively, the chronic inflammatory condition can be prevented, treated or symptoms alleviated along with at least one suitable anti-inflammatory drug (e.g., one, two or three of such drugs). Non-limiting examples of such drugs include certain steroids (e.g., corticosteroids), non-steroidal anti-inflammatory drugs (NSAIDs) such as aspirin, ibuprofen and naproxen, and analgesics such as paracetamol, acetaminophen and the like; as well as ImSAIDs.

It will be appreciated that when the indication to be treated is rheumatoid arthritis or a related disorder, the subject may be receiving or will receive a disease modifying antirheumatic drug (known as DMARD) such as methotrexate, leflunomide, hydroxychloroquine, sulfasalazine, and the like. In one embodiment, the DMARD can be administered along with at least one compound of formula (I) such as one, two or three of such compounds. In another embodiment, the subject can receive in addition to the DMARD a suitable biologic such as those mentioned below along with at least one compound of formula (I) such as one, two or three of such compounds. When a subject starts using a particular biologic agent, they will often also remain on their current dose of nonsteroidal anti-inflammatory (NSAID) and/or corticosteroid (i.e., prednisone) medicines.

It will be appreciated that therapeutic methods according to the invention are flexible and can be practiced in several ways to acheived a desired outcome. Thus in one embodiment, the method includes administering a compound having Formula I to a subject (e.g., using an oral, i.v, i.p or other route) followed by administration of an anti-inflammatory drug as described herein. Use of a suitable biologic (e.g. an antibody therapeutic as provided herein) may also be indicated. Alternatively, the method can be practiced by administering the anti-inflammatory drug first followed by administration of the compound having the Formula I. Choice of a particular methodology and administration route will be guided by understood parameters such as the chronic inflammatory disorder to be treated, age and sex of the subject, etc.

Hyperproliferative Disorders

In another aspect, the invention provides compounds of formula (I) or (II) for use in the management, treatment or prevention of any condition or clinical situation where it is desirable (or where it may be of benefit) to prevent or inhibit the growth of cells. Examples include tumors, cancers, neoplastic tissues, and other premalignant and noneoplastic hyperproliferative disorders, all of which together are referred to herein as hyperproliferative or hyperplastic disorders.

The term "inhibit" is used broadly to include any reduction or decrease in cell growth as well as the prevention or abolition of cell growth. "Inhibition" thus includes the reduction or prevention of cell growth. This may be determined by any appropriate or convenient means, such as determining or assessing cell number, size (e.g size of tissue in which the cells are contained), cell viability and/or cell death etc., as may be determined by techniques well known in the art.

"Growth" of cells as referred to herein is also used broadly to include any aspect of cell growth, including in particular the proliferation of cells.

The compounds of formula (I) or (II) may thus be used in the treatment of any condition (used broadly herein to include any disorder or any clinical situation) which is responsive to reduction of cell growth (particularly cell proliferation). The compounds accordingly find utility in any therapy (or treatment) which targets cell growth (or proliferation). In other words, the compounds may be used in any therapeutic application in which it desirable or advantageous to inhibit cell proliferation.

A treatment may include any clinical step or intervention which contributes to, or is a part of, a treatment programme or regimen. A prophylactic treatment may include delaying, limiting, reducing or preventing the condition or the onset of the condition, or one or more symptoms thereof, for example relative to the condition or symptom prior to the prophylactic treatment. Prophylaxis thus explicitly includes both absolute prevention of occurrence or development of the condition, or symptom thereof, and any delay in the onset or development of the condition or symptom, or reduction or limitation on the development or progression of the condition or symptom. Treatment according to the invention thus includes killing, inhibiting or slowing the growth of cells, or the increase in size of a body or population of cells (e.g in a tissue, tumour or growth), reducing cell number or preventing spread of cells (e.g to another anatomic site), reducing the size of a cell growth etc. The term "treatment" does not imply cure or complete abolition or elimination of cell growth, or a growth of cells.

Since the therapeutic applications and utilities of the present invention may generally involve inhibiting cell proliferation, nearly any proliferating cell may be targeted in the therapies and utilities disclosed and encompassed herein. Such proliferating cells may include healthy or diseased cells and cells of any tissue in which proliferation occurs. For example, such cells may include in particular neoplastic cells, including both malignant and non-malignant neoplastic cells and cells of the immune system (immune cells), cells of the haematopoietic system generally, or skin cells.

The compounds of formula (I) or (II) can be employed to treat one or a combination of hyperproliferative disorders as the sole active agent or in combination with one or more other agents. In one embodiment, disorders or conditions involving abnormal or unwanted cell growth may be treated with known agents including known cytotoxic and/or cytostatic agents including chemotherapeutic agents. Accordingly, as alternatively stated above, the compounds of formula (I) or (II) may be used in any method of treatment which involves (or includes) the use of such cytotoxic and/or cytostatic agents. This may include the treatment of any condition responsive to a cytotoxic and/or cytostatic agent or any condition which may be treated with or which requires the use of such agent(s).

The treatment of hyperproliferative disorders represents an aspect of particular interest. The term "hyperproliferative disorder" is used broadly herein to include any disorder or condition which involves increased, undesired or unwanted proliferation of cells. Thus included are not only conditions in which proliferation of cells is increased, for example relative to normal or healthy cells, or cells in the absence of the condition in question (e.g. compared or relative to a healthy or control subject, or compared or relative to cells taken from healthy or unaffected tissue in the same subject), but also conditions in which cell proliferation is not increased (or not greatly or significantly increased) over normal, but in which the proliferation which occurs is unwanted or undesired, whether generally or in a particular context. This may include for example an unwanted or undesired proliferation of cells which may occur in a "normal" response.

A hyperproliferative disorder of particular interest involves the proliferation of cells which have the capacity for autonomous growth i.e. cells which exist and reproduce independently of normal regulatory mechanisms. A hyperproliferative disorder may therefore be a neoplastic disorder, and as noted above, this may be a pre-malignant, malignant, non-malignant or non-neoplastic disorder. Examples of pre-malignant or non-neoplastic or non-malignant hyperproliferative disorders include myelodysplastic disorders, cervical carcinoma-in-situ, familial intestinal polyposes (e.g. Gardner syndrome), oral leukoplasias, histiocytoses, keloids, hemangiomas, hyperproliferative arterial stenosis, inflammatory arthritis, hyperkeratoses, and papulosquamous eruptions, including arthritis. Also included are viral-induced hyperproliferative diseases such as warts and EBV-induced disease (e.g. infectious mononucleosis), scar formation and the like.

The hyperproliferative disorder may thus be any hyperproliferative disorder, for example selected from neoplastic disorders such as cancer (benign or metastatic). Cancer represents a hyperproliferative disorder of particular interest, and all types of cancers, including e.g. solid tumours and haematological cancers are included. Representative types of cancer include cervical cancer, uterine cancer, ovarian cancer, pancreatic cancer, kidney cancer, gallbladder cancer, liver cancer, head and neck cancer, squamous cell carcinoma, gastrointestinal cancer, breast cancer, prostate cancer, testicular cancer, lung cancer, non-small cell lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer (e.g. astrocytoma, glioblastoma, medulloblastoma), neuroblastoma, sarcomas, colon cancer, rectum cancer, stomach cancer, anal cancer, bladder cancer, pancreatic cancer, endometrial cancer, plasmacytoma, lymphomas, retinoblastoma, Wilm's tumor, Ewing sarcoma, melanoma and other skin cancers.

Mention may be made also of sinus tumours, urethral and genito-urinary cancers, oesophageal cancer, myeloma, endocrine cancers, osteosarcoma, angiosarcoma, and fibrosarcoma, and any tumour of the peripheral or central nervous systems, malignant or benign, including gliomas and neuroblastomas.

In embodiments in which the hyperproliferative disorder is a cancer, the invention also features methods of treating a subject (e.g. a human that has or is suspected of having cancer) in which the method includes treating the subject with at least one compound having Formula I or II, preferably one, two or three of such compounds alone or along with an effective amount of one or more agents having cytotoxic or cytostatic activity such as a chemotherapeutic agent (e.g., one, two or three of such agents). Illustrative chemotherapeutic agents are "small molecules" selected from the group consisting of abiraterone acetate, altretamine, anhydrovinblastine, auristatin, bexarotene, bicalutamide, BMS184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine (BCNU), cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, 5-fluorouracil, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

Other suitable chemotherapeutic agents for use with the invention include biologics such as immune molecules that exhibit a cytotoxic or cytostatic activity against a targeted cell or tissue. More specific examples include antibodies and antigen-binding fragments thereof, namely monoclonal, polyclonal, chimeric and humanized antibodies. Non-limiting examples include the following therapeutic antibodies that have been approved for human use for several medical indications: Abciximab (ReoPro), Adalimumab (Humira), Alemtuzumab (Campath), Basiliximab (Simulect), Belimumab (Benlysta), Bevacizumab (Avastin), Brentuximab vedotin (Adcetris), Canakinumab (Ilaris) Cetuximab (Erbitux), Certolizumab pegol[19] (Cimzia), Daclizumab (Zenapax), Denosumab (Prolia, Xgeva), Eculizumab (Soliris), Efalizumab (Raptiva), Gemtuzumab (Mylotarg), Golimumab (Simponi), Ibritumomab tiuxetan (Zevalin), Infliximab (Remicade), Ipilimumab (MDX-101) (Yervoy), Muromonab-CD3, (Orthoclone OKT3), Natalizumab (Tysabri), Ofatumumab (Arzerra), Omalizumab (Xolair), Palivizumab (Synagis), Panitumumab (Vectibix), Ranibizumab (Lucentis), Rituximab (Rituxan, Mabthera) Tocilizumab (or Atlizumab) (Actemra and RoActemra), Tositumomab (Bexxar) a nd Trastuzumab (Herceptin).

Also included within the scope of suitable biologics for use with the invention are certain antibody-small molecule conjugates such as TDM1 (conjugate of trastuzumab and doxorubicin).

In embodiments in which the hyperproliferative disorder is cancer and particularly a cancer of the breast, the chemotherapeutic drug may be selected from the following: Abitrexate (Methotrexate), Abraxane (Paclitaxel Albumin-stabilized Nanoparticle Formulation) Ado-Trastuzumab Emtansine, Adriamycin PFS (Doxorubicin Hydrochloride), Adriamycin RDF (Doxorubicin Hydrochloride), Adrucil (Fluorouracil), Afinitor (Everolimus), Anastrozole, Arimidex (Anastrozole), Aromasin (Exemestane), Capecitabine, Clafen (Cyclophosphamide), Cyclophosphamide, Cytoxan (Cyclophosphamide), Docetaxel, Doxorubicin Hydrochloride, Efudex (Fluorouracil), Ellence (Epirubicin Hydrochloride), Epirubicin Hydrochloride, Everolimus, Exemestane, Fareston (Toremifene), Faslodex (Fulvestrant), Femara (Letrozole), Fluoroplex (Fluorouracil), Fluorouracil, Folex (Methotrexate), Folex PFS (Methotrexate), Fulvestrant, Gemcitabine Hydrochloride, Gemzar (Gemcitabine Hydrochloride), Herceptin (Trastuzumab), Ixabepilone, Ixempra (Ixabepilone), Lapatinib Ditosylate, Letrozole, Methotrexate, Methotrexate LPF (Methotrexate), Mexate (Methotrexate), Mexate-AQ (Methotrexate), Neosar (Cyclophosphamide), Nolvadex (Tamoxifen Citrate), Novaldex (Tamoxifen Citrate), Paclitaxel, Paclitaxel Albumin-stabilized Nanoparticle Formulation, Perjeta (Pertuzumab), Pertuzumab, Tamoxifen Citrate, Taxol (Paclitaxel), Taxotere (Docetaxel), Trastuzumab, Toremifene, Tykerb (Lapatinib Ditosylate), and Xeloda (Capecitabine)

In another aspect, the invention features methods of treating a subject (e.g. a human) having or suspected of having a hyperproliferative disorder such as cancer, involving administering to the subject an effective amount of a compound according to Formula I or II either as a sole agent or along with an effective amount of one or more chemotherapeutic agents described above (e.g., one, two or three of such agents). An illustrative treatment regimen involves treating, preventing or minimizing tumor progression or metastasis in a subject having a neoplasia, where the neoplastic cell is a cancer cell or is present in a tumor.

In another aspect, the invention features a method of treating, preventing or minimizing tumor progression or metastasis in a subject where the tumor is breast cancer, melanoma, glioblastomas, colon cancer, non-small cell lung cancer, or lymphomas, involving administering to the subject an effective amount of at least one compound according to Formula I or II (e.g., one, two or three of such compounds) alone or along with one or more other chemotherapeutic agents as described herein (e.g, one or two of such agents).

In a particularly preferred embodiment, the invention relates to a method for preventing or treating breast cancer in a patient, the method comprising the steps of administering to the patient an effective amount of at least one chemotherapeutic agent; and administering an effective amount of at least one compound of formula (I) or formula (II).

It is further preferred if a chemotherapeutic agent is administered to the patient before the administration of the compound (I) or (II), such as one or more of paclitaxel, doxorubicin, cyclophosphamide and cisplatin.

The method may also comprise the administration of one or more of trastuzumab (Herceptin), trastuzumab-doxorubicin conjugate (TDM1) and pertuzumab (Perjeta).

It will be appreciated that therapeutic methods according to the invention are flexible and can be practiced in several ways to acheived a desired outcome for the subject. Thus in one embodiment, the method includes administering a compound having Formula I or II to a subject (e.g., using an oral, i.v, i.p or other route) followed by administration of at least one chemotherapeutic agent as described herein (e.g., one, two or three of such agents). Alternatively, the method can be practiced by administering the chemotherapeutic agent first followed by administration of the compound having the Formula I or II. Choice of a particular methodology and administration route will be guided by understood parameters such as the hyperproliferative disorder to be treated, age and sex of the subject, etc.

The method of the invention may also comprise the treatment of chronic inflammatory disorders associated a diabetic condition in a patient, particularly diabetes mellitus, such as diabetic nephropathy and diabetic retinopathy.

Subjects to be treated by the methods of the present invention include both human subjects (patients) and animal subjects for veterinary purposes. Animal subjects are generally mammalian subjects such as horses, dogs, cats, cows, rabbits, sheep and the like.

Screen

Suitable compounds for use with the present methods for treating, preventing or alleviating symptoms a hyperproliferative disorder can be selected by one or a combination of different strategies which are intended to detect and preferably quantify changes in cell proliferation when contacted by one or more invention compounds. Non-limiting examples of such screens are provided below:

a. NCI60 Screen: In one approach, a compound of formula (I) or (II) is tested for efficacy in the NCI60 human humor cell line anticancer drug screen reported by Shoemaker, R. H (2006) *Nat. Reviews Cancer* 6, 813. Briefly, the NCI60 screen is a two-stage process, beginning with the evaluation of all compounds against 60 cell lines at a single dose of 10 μM. Compounds giving a growth inhibition of 50% (GI50) is calculated from $[(Ti-Tz)/(C-Tz)]\times100=50$, which is the compound concentration resulting in a 50% reduction in the net protein increase (as measured by SRB staining) in control cells during the incubation. Preferred compounds of formula (I) or (II) of the invention have a GI50 of about 1-5 μM in the NCI60 screen, more preferably about 0.01-0.1 μM or less with respect to at least one of the cell lines in the NCI60 screen.

See also Alley, M. C., et al. Cancer Research 48: 589-601, 1988; Grever, M. R., et al. The National Cancer Institute: Cancer Drug Discovery and Development Program. Seminars in Oncology, Vol. 19, No. 6, pp 622-638, 1992; and Boyd, M. R., and Paull, K. D. Some Practical Considerations and Applications of the National Cancer Institute In Vitro Anticancer Drug Discovery Screen. Drug Development Research 34: 91-109, 1995.

b. Screen based on Clin Cancer Res. 2008 Dec. 15; 14(24):8070-9.

Patel M I, Singh J, Niknami M, Kurek C, Yao M, Lu S, Maclean F, King N J, Gelb M H, Scott K F, Russell P J, Boulas J, Dong Q.

In another approach the expression of cPLA2-alpha can be determined in prostate cancer cells by reverse transcription-PCR, Western blot, and immunocytochemistry. Growth inhibition, apoptosis, and cPLA2-alpha activity can be determined after inhibition with cPLA2-alpha small interfering RNA or inhibitor (Wyeth-1). Cytosolic PLA2-alpha inhibitor or vehicle can also be administered to prostate cancer xenograft mouse models. Finally, the expression of phosphorylated cPLA2-alpha can be determined by immunohistochemistry in human normal, androgen-sensitive and androgen-insensitive prostate cancer specimens.

Formulation

Irrespective of their intended use, the compounds of formula (I) or (II) of the invention are preferably formulated as pharmaceutically acceptable compositions. The phrase "pharmaceutically acceptable", as used in connection with compositions of the invention, refers to molecular entities and other ingredients of such compositions that are physiologically tolerable and do not typically produce untoward reactions when administered to a mammal (e.g. human). Preferably, as used herein, the term "pharmaceutically acceptable" means approved by a regulatory agency of the Federal or a state government or listed in the U.S. Pharmacopoeia or other generally recognized pharmacopoeia for use in mammals, and more particularly in humans.

The term "carrier" applied to pharmaceutical compositions of the invention refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described in "Remington's Pharmaceutical Sciences" by E. W. Martin, 18th Edition, incorporated by reference. Particularly preferred for the present invention are carriers suitable for immediate-release, i.e., release of most or all of the active ingredient over a short period of time, such as 60 minutes or less, and make rapid absorption of the drug possible.

The compounds of formula (I) or (II) can be administered in salt, solvate, prodrug or ester form, especially salt form. Typically, a pharmaceutical acceptable salt may be readily prepared by using a desired acid. The salt may precipitate from solution and be collected by filtration or may be recovered by evaporation of the solvent. For example, an aqueous solution of an acid such as hydrochloric acid may be added to an aqueous suspension of a compound of formula (I) or (II) and the resulting mixture evaporated to dryness (lyophilised) to obtain the acid addition salt as a solid. Alternatively, a compound of formula (I) or (II) may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Suitable addition salts are formed from inorganic or organic acids which form non-toxic salts and examples are hydrochloride, hydrobromide, hydroiodide, sulphate, bisulphate, nitrate, phosphate, hydrogen phosphate, acetate, trifluoroacetate, maleate, malate, fumarate, lactate, tartrate, citrate, formate, gluconate, succinate, pyruvate, oxalate, oxaloacetate, trifluoroacetate, saccharate, benzoate, alkyl or aryl sulphonates (eg methanesulphonate, ethanesulphonate, benzenesulphonate or p-toluenesulphonate) and isethionate. Representative examples include trifluoroacetate and formate salts, for example the bis or tris trifluoroacetate salts and the mono or diformate salts, in particular the tris or bis trifluoroacetate salt and the monoformate salt.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The salts of the compound of Formula (I) or (II) may form solvates (e.g. hydrates) and the invention also includes all such solvates.

The term "prodrug" as used herein means a compound which is converted within the body, e.g. by hydrolysis in the blood, into its active form that has medical effects.

The compounds of formula (I) of the invention are proposed for use in the treatment of, inter alia, chronic inflammatory disorders and cancer. The compounds of formula (II) of the invention are proposed for use in the treatment of, inter alia, cancer. By treating or treatment is meant at least one of:

(i). preventing or delaying the appearance of clinical symptoms of the disease developing in a mammal;
(ii). inhibiting the disease i.e. arresting, reducing or delaying the development of the disease or a relapse thereof or at least one clinical or subclinical symptom thereof, or
(iii). relieving or attenuating one or more of the clinical or subclinical symptoms of the disease.

The benefit to a subject to be treated is either statistically significant or at least perceptible to the patient or to the physician. In general a skilled man can appreciate when "treatment" occurs.

The word "treatment" is also used herein to cover prophylactic treatment, i.e. treating subjects who are at risk of developing a disease in question.

The compounds can be used on any animal subject, in particular a mammal and more particularly to a human or an animal serving as a model for a disease (e.g. mouse, monkey, etc.).

An "effective amount" means the amount of a compound that, when administered to an animal for treating a state, disorder or condition, is sufficient to effect such treatment. The "effective amount" will vary depending on the compound, the disease and its severity and the age, weight, physical condition and responsiveness of the subject to be treated and will be ultimately at the discretion of the attendant doctor.

While it is possible that, for use in the methods of the invention, a compound of formula (I) or (II) may be administered as the bulk substance, it is preferable to present the active ingredient in a pharmaceutical formulation, for example, wherein the agent is in admixture with a pharmaceutically acceptable carrier selected with regard to the intended route of administration and standard pharmaceutical practice.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

It will be appreciated that pharmaceutical compositions for use in accordance with the present invention may be in the form of oral, parenteral, transdermal, inhalation, sublingual, topical, implant, nasal, or enterally administered (or other mucosally administered) suspensions, capsules or tablets, which may be formulated in conventional manner using one or more pharmaceutically acceptable carriers or excipients.

There may be different composition/formulation requirements depending on the different delivery systems. Likewise, if the composition comprises more than one active component, then those components may be administered by the same or different routes.

The pharmaceutical formulations of the present invention can be liquids that are suitable for oral, mucosal and/or parenteral administration, for example, drops, syrups, solutions, injectable solutions that are ready for use or are prepared by the dilution of a freeze-dried product but are preferably solid or semisolid as tablets, capsules, granules, powders, pellets, pessaries, suppositories, creams, salves, gels, ointments; or solutions, suspensions, emulsions, or other forms suitable for administration by the transdermal route or by inhalation.

The compounds of the invention can be administered for immediate-, delayed-, modified-, sustained-, pulsed- or controlled-release applications.

In one aspect, oral compositions are slow, delayed or positioned release (e.g., enteric especially colonic release) tablets or capsules. This release profile can be achieved without limitation by use of a coating resistant to conditions within the stomach but releasing the contents in the colon or other portion of the GI tract wherein a lesion or inflammation site has been identified or a delayed release can be achieved by a coating that is simply slow to disintegrate or the two (delayed and positioned release) profiles can be combined in a single formulation by choice of one or more appropriate coatings and other excipients. Such formulations constitute a further feature of the present invention.

Pharmaceutical compositions can be prepared by mixing a therapeutically effective amount of the active substance with a pharmaceutically acceptable carrier that can have different forms, depending on the way of administration. Typicaly composition components include one or more of binders, fillers, lubricants, odorants, dyes, sweeteners, surfactants, preservatives, stabilizers and antioxidants.

The pharmaceutical compositions of the invention may contain from 0.01 to 99% weight—per volume of the active material. The therapeutic doses will generally be between about 10 and 2000 mg/day and preferably between about 30 and 1500 mg/day. Other ranges may be used, including, for example, 50-500 mg/day, 50-300 mg/day, 100-200 mg/day.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art.

It is within the scope of the invention for a compound as described herein to be administered in combination with another pharmaceutical, e.g. another drug with known efficacy against the disease in question. The compounds of formula (I) or (II) of the invention may therefore be used in combination therapy.

The chemistry described in the following schemes is used to manufacture the compounds described in the tables which follow. The starting materials in each scheme are readily available compounds. In general, molar equivalents of each reactant are employed.

The invention will now be further described with reference to the following non limiting examples and FIG. 1. FIG. 1 describes Tumor volume in mice treated with Compound A.

EXAMPLE 1

Preparation and Testing of Compounds A and B

Experimental procedures suitable for the formation and testing of these compounds can be found in WO2011/039365 as well as references cited therein. The following compounds are prepared:

TABLE 1

Compound A
47

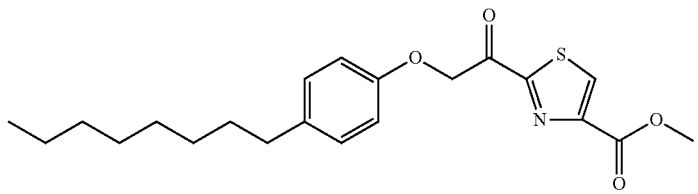 [SMILES: CCCCCCCCc1ccc(OCC(=O)c2nc(C(=O)OC)cs2)cc1]

Compound B
37a

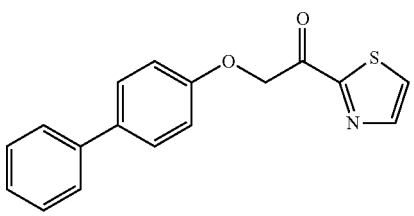 [SMILES: O=C(COc1ccc(-c2ccccc2)cc1)c1nccs1]

Analytical data is presented in

TABLE 2

| Code | AA release SW982 cells (0-20 μM) IC50 (μM) | cPLA2 in vitro assay (0-5 μM) IC50 (μM) | GIVA cPLA$_2$ % Inhibition | GIVA cPLA$_2$ XI(50) | GVIA iPLA$_2$ % Inhibition | GV sPLA$_2$ % Inhibition | PGE2- assay % inhibition |
|---|---|---|---|---|---|---|---|
| B | ~2.5 | 35% inh at 1 μM | 80 | | 23 | 41 | ~6 μM |
| A | ~0.6 | ~0.3 | >90 | 0.011 | 86.4 | 41.1 | ~0.75 μM |

EXAMPLE 2

Preparation and Use of Compounds C and D

General guidance regarding regarding the preparation and testing of Compounds C and D can be found WO2011/039365 as well as references cited therein. The following compounds are prepared:

TABLE 3

Compound C
32d

Compound D
32c

Analytical data is presented

TABLE 4

| Code | AA release SW982 cells (0-20 μM) IC50 (μM) | cPLA2 in vitro assay (0-5 μM) IC50 (μM) | GIVA cPLA$_2$ % Inhibition | GIVA cPLA$_2$ XI(50) | GVIA iPLA$_2$ % Inhibition | GV sPLA$_2$ % Inhibition | PGE2- assay % inhibition |
|---|---|---|---|---|---|---|---|
| C | >20 | ->5 | 58 | | 5 | 4 | — |
| D | ->20 | ->5 | 40 | | 13 | 0 | |

EXAMPLE 3

Preparation and Use of Compounds E-T

Compounds E-T are shown in the following Table 5:

Compound E

-continued
Compound F
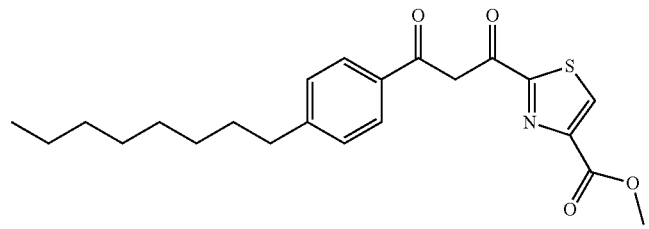 [SMILES: CCCCCCCCc1ccc(C(=O)CC(=O)c2nc(C(=O)OC)cs2)cc1]
Compound G
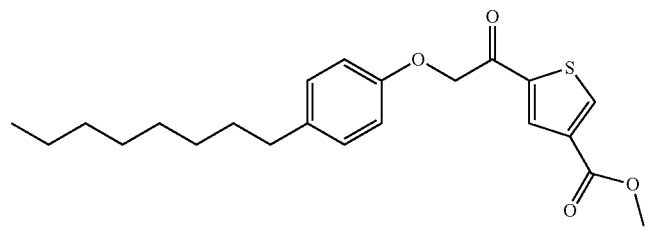
Compound H
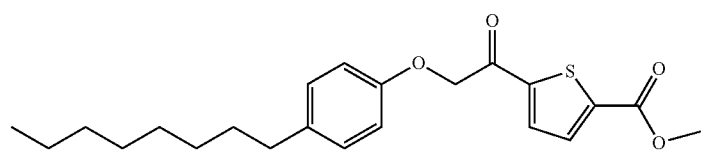 [SMILES: CCCCCCCCc1ccc(OCC(=O)c2ccc(C(=O)OC)s2)cc1]
Compound I
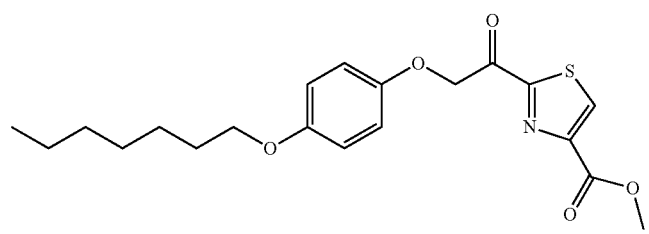 [SMILES: CCCCCCCOc1ccc(OCC(=O)c2nc(C(=O)OC)cs2)cc1]
Compound J
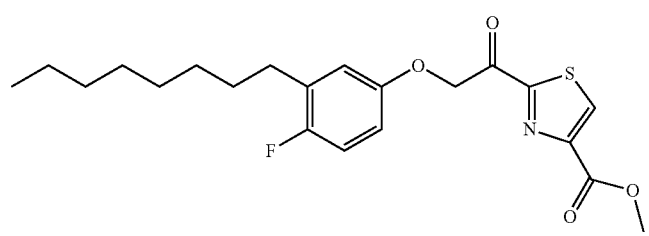 [SMILES: CCCCCCCCc1cc(OCC(=O)c2nc(C(=O)OC)cs2)ccc1F]
Compound K
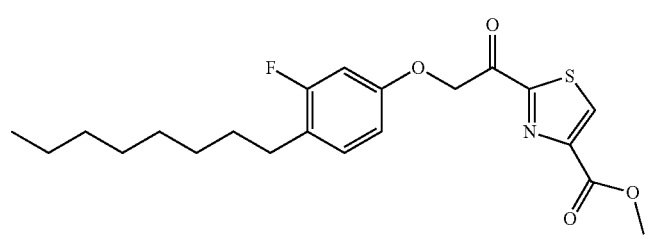 [SMILES: CCCCCCCCc1ccc(OCC(=O)c2nc(C(=O)OC)cs2)cc1F]
Compound L
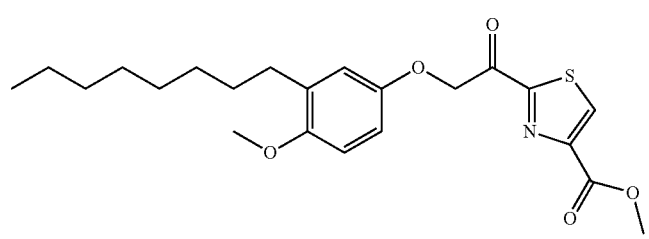 [SMILES: CCCCCCCCc1cc(OCC(=O)c2nc(C(=O)OC)cs2)ccc1OC]

-continued

Compound M

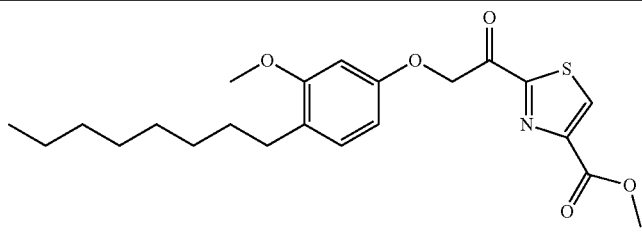

Compound N

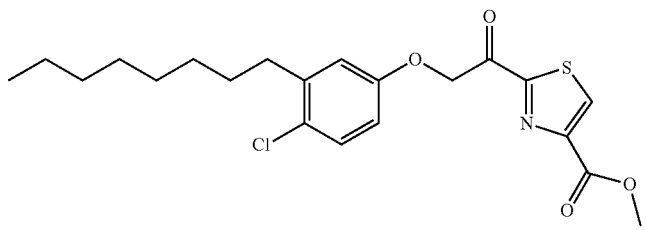 [SMILES: CCCCCCCCc1cc(OCC(=O)c2nc(C(=O)OC)cs2)ccc1Cl]

Compound O

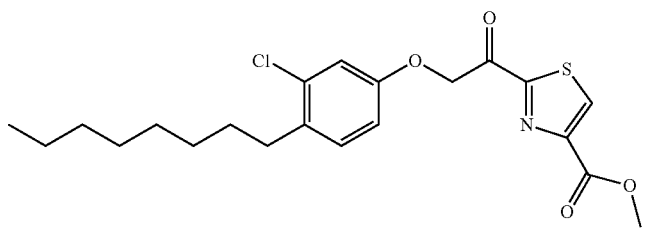 [SMILES: CCCCCCCCc1ccc(OCC(=O)c2nc(C(=O)OC)cs2)cc1Cl]

Compounds P1-P3
P1$_{a,b}$: (n = 1, X = F,
--- is a single (P1$_a$)
or double bond (P1$_b$)
P2$_{a,b}$: (n = 1, X = Cl,
--- is a single (P2$_a$)
or double (P2$_b$) bond
P3$_{a,b}$: (n = 1, X = OMe,
--- is a single (P3$_a$)
or double (P3$_b$) bond

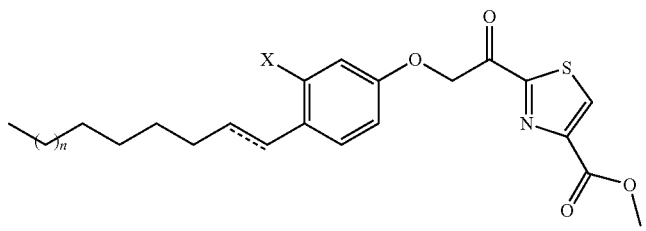

Compounds Q1-Q3
Q1$_{a,b}$: (n = 1, X = F,
--- is a single (Q1$_a$)
or double (Q1$_b$) bond
Q2$_{a,b}$: (n = 1, X = Cl,
--- is a single (Q2$_a$)
or double (Q2$_b$) bond
Q3$_{a,b}$: (n = 1, X = OMe,
--- is a single (Q3$_a$)
double (Q3$_b$) bond

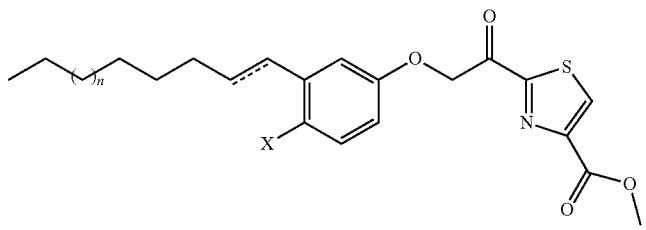

Compounds R1-R3
R1$_{a,b}$: (n = 1, X = F,
--- is a single (R1$_a$)
or double (R1$_b$) bond
R2$_{a,b}$: (n = 1, X = Cl,
--- is a single (R2$_a$)
(R2$_b$) or double bond
R3$_{a,b}$: (n = 1, X = OMe,
--- is a single (R3$_a$)
or double (R3$_b$) bond

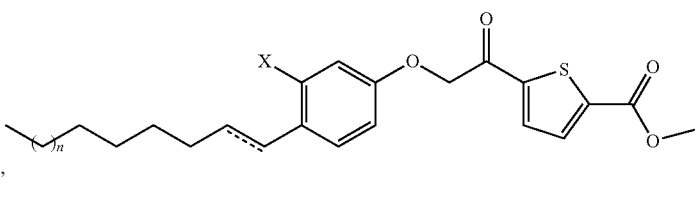

Compounds S1-S3
S1$_{a,b}$: (n = 1, X = F,
--- is a single (S1$_a$)
or double (S1$_b$) bond
S2$_{a,b}$: (n = 1, X = Cl,
--- is a single (S2$_a$)
(S2$_b$) or double bond
S3$_{a,b}$: (n = 1, X = OMe,
--- is a single (S3$_a$)
or double (S3$_b$) bond

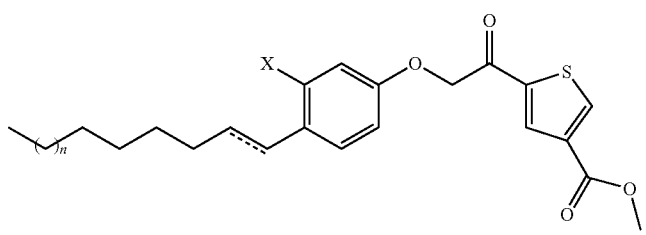

| | |
|---|---|
| Compounds T1-T3<br>T1$_{a,b}$: (n = 1, X = F,<br>--- is a single (T1$_a$)<br>or double (T1$_b$) bond<br>T2$_{a,b}$: (n = 1, X = Cl,<br>--- is a single (T2$_a$)<br>(T2$_b$) or double bond<br>T3$_{a,b}$: (n = 1, X = OMe,<br>--- is a single (T3$_a$)<br>or double (T3$_b$) bond | 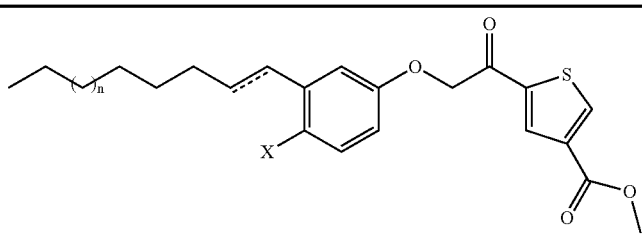 |
| Compound V | 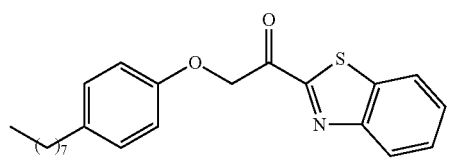 |
| Compound W | 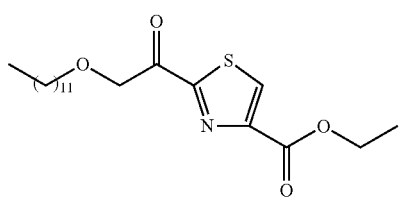 |
| Compound X | 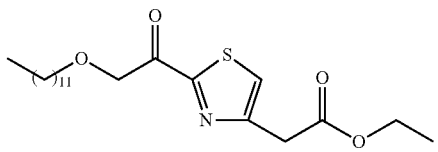 |
| Compound Y | 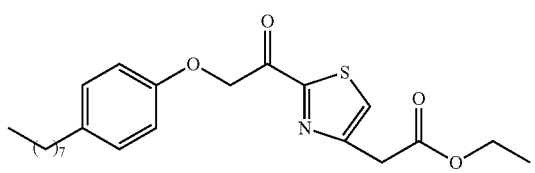 |

A. Derivatives with Varying Benzene Substitution Patterns

Certain compounds shown above in Table 5 call for variable substitution pattern of the benzene ring in the octylphenol moiety. Linear sequences starting from substituted 3-hydroxybenzaldehydes (1) and 4-hydroxybenzaldehydes (2) may be developed. However, compounds 1 and 2 are, albeit commercially available, both relatively expensive and may not be available in the quantities sufficient for all applications and particularly in amounts to serve as starting materials for a 10+ steps linear synthetic sequence.

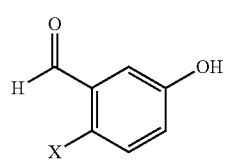

1a: X = F
1b: X = Cl
1c: X = OMe

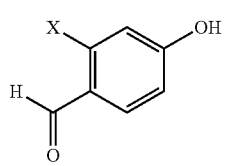

2a: X = F
2b: X = Cl
2c: X = OMe

Alternatively, it is possible to use a convergent approach where two halves of equal sizes are joined in the last step. This is advantageous for several reasons; one half is kept constant, whereas the other half provides several opportunities for easy introduction of variations (Scheme 1). Furthermore, the total number of steps is kept low.

Scheme 4. Reagents and conditions: a) base, BnBr; b) heptylphosphonium bromide, BuLi, THF; c) H₂ (g), Pd/C.

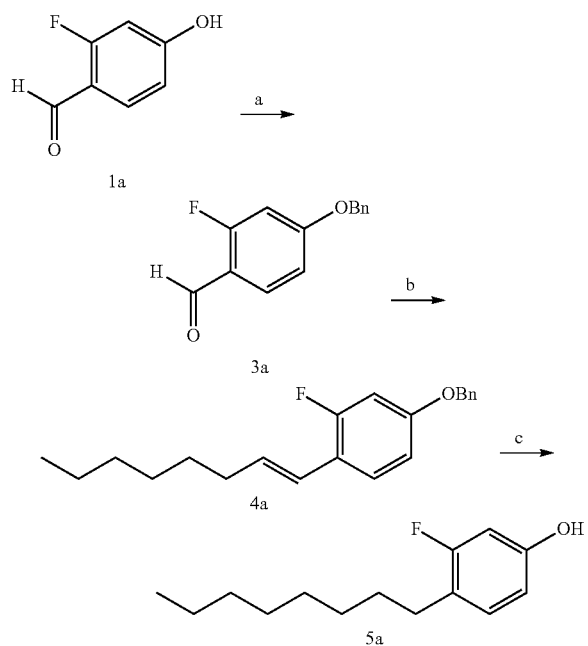

Scheme 4 is applicable for compounds both of type 1 and 2, and comprises mainly standard reactions. After introduction of a protecting group in the first step, Wittig coupling with an alkylphosphonium salt of suitable length provides compounds 4. By protecting the phenol as benzyl ether, reduction of the double bond and deprotection can be obtained simultaneously, giving substituted octylphenols (5). If another protecting group is selected, the double bond in 4 might be possible to preserve in the final product, providing another opportunity for variation.

For the second fragment, we suggest a route starting with 2,4-dibromothiazole (6, commercially available). For the first two lithiation steps, there are opportunities for rearrangements. The TMS derivative 7 we suggest is less prone to rearrangement.

Scheme 5. Reagents and conditions: a) i. BuLi, Et₂O; ii. Me₃SiCl; b) i. BuLi, THF; ii. Dimethylcarbonate; c) 2-bromoacetyl bromide, DCM.

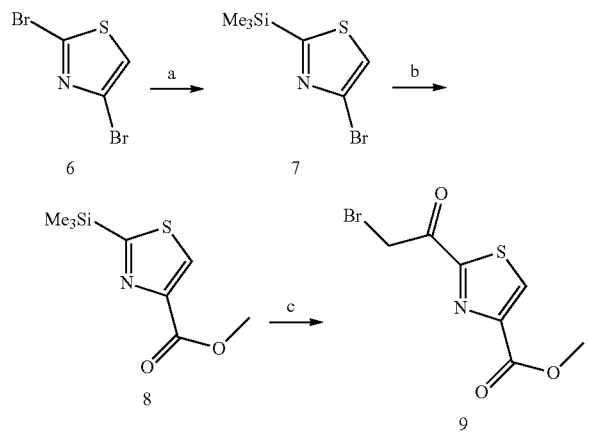

The last step in Scheme 5 to fragment 9 is well established (Dondoni et al, J. Am. Chem. Soc. 116 (1994) 3324).

The two fragments 5 and 9 are finally joined by a standard Williamson ether preparation, Scheme 6.

Scheme 6. Reagents and conditions: K₂CO₃, acetone.

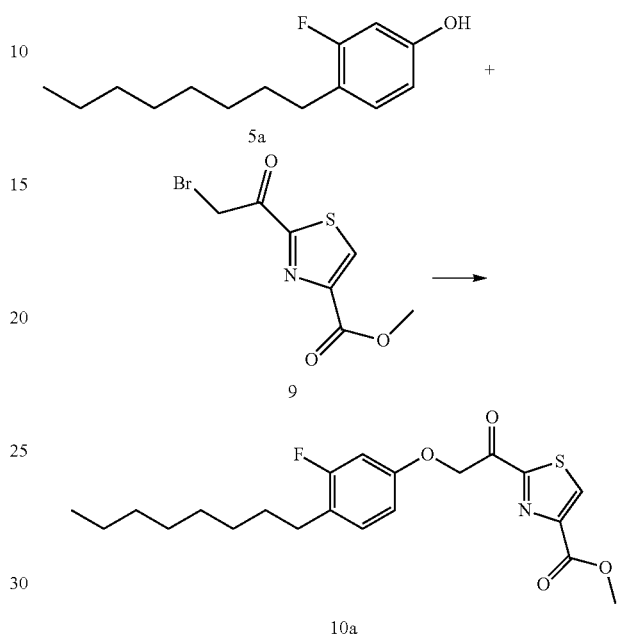

The general structure of compounds from this route is provided below, X=F, Cl, OMe.

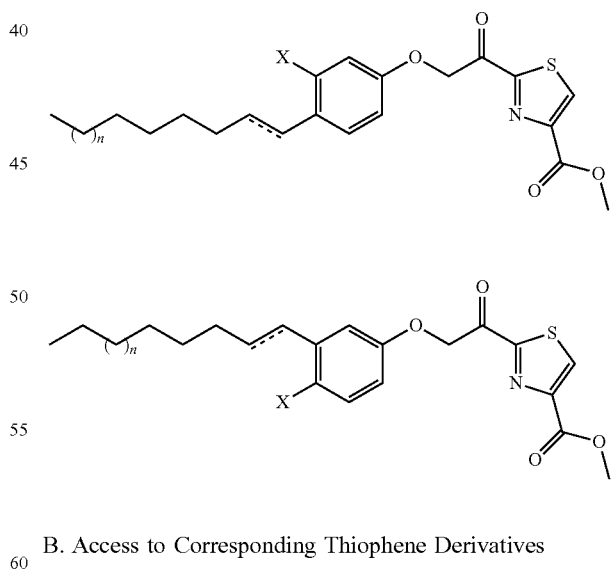

B. Access to Corresponding Thiophene Derivatives

Thiophene derivatives of all the above compounds (and others) are available from thiophene analogs of 9. We suggest synthesis of the two regioisomers 11 and 12, available from commercial starting materials 13 and 14 in two steps; acid-catalyzed esterification followed by alpha-bromination of the acyl group, Scheme 4. Several conditions are available for both transformations.

Scheme 7. Reagents and conditions: a) SOCl₂, methanol; b) Br₂, acetic acid.

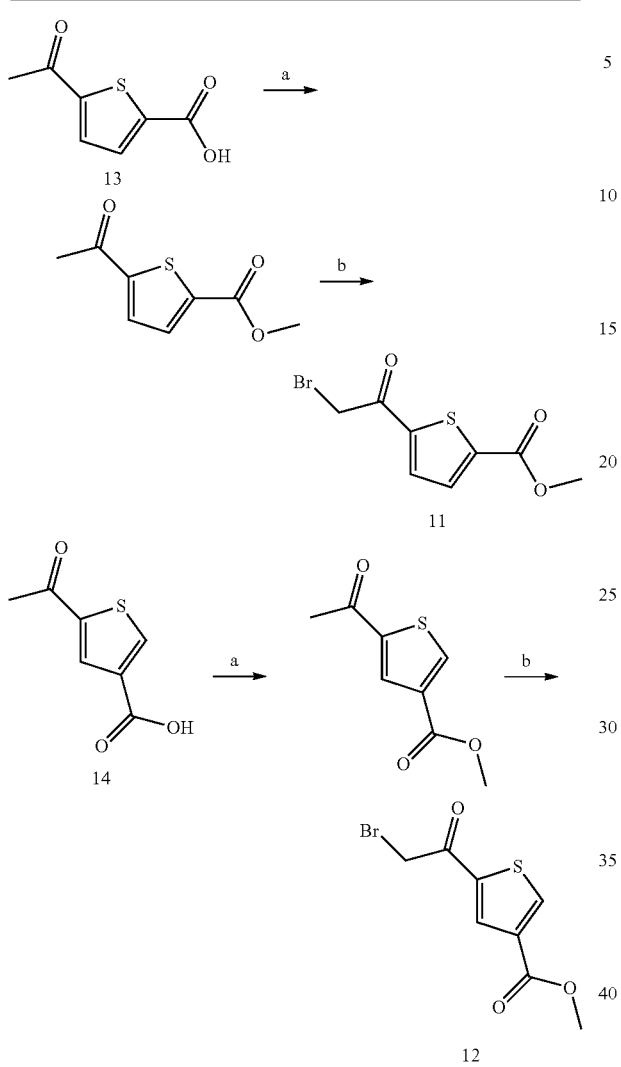

This allows the synthesis of the following derivatives, with similar scope for variability as above:

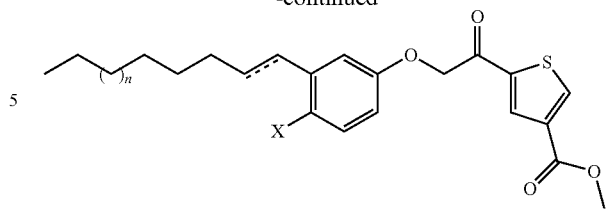

C. Synthesis of Compounds E and F.

The thioether variation of Compound A (19) may be prepared as described below in Scheme 8.

Scheme 8. Reagents and conditions: a) Pd₂(dba)₃, Xantphos, Hünig's base, dioxane; b) Trifluoroacetic acid; c) K₂CO₃, EtOH.

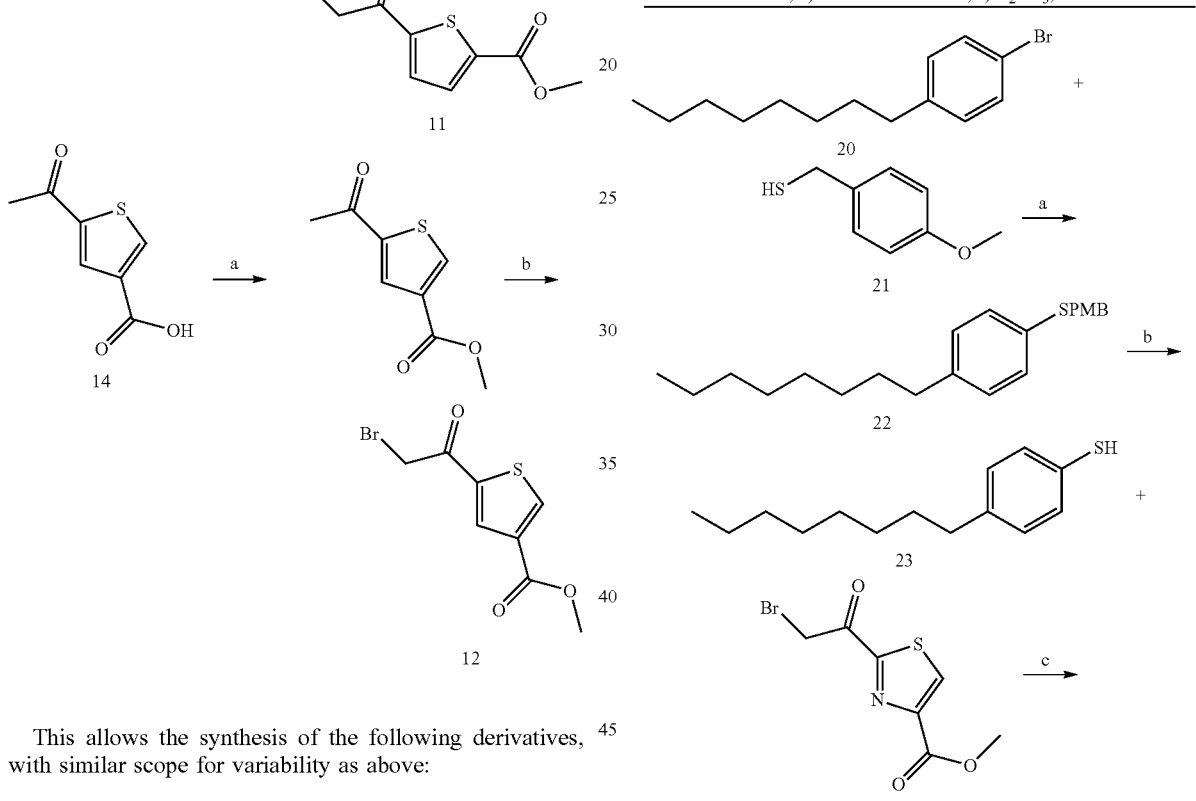

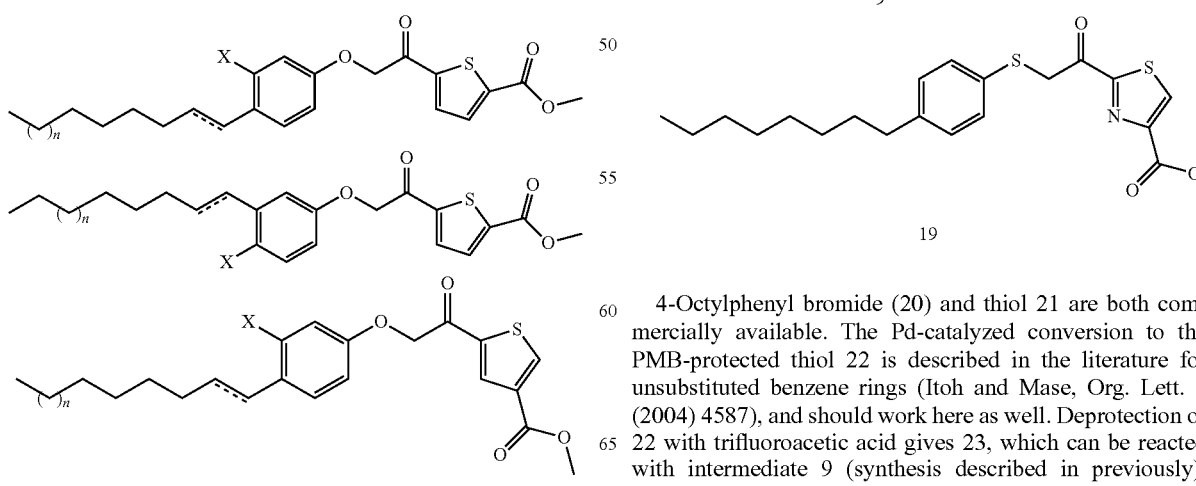

4-Octylphenyl bromide (20) and thiol 21 are both commercially available. The Pd-catalyzed conversion to the PMB-protected thiol 22 is described in the literature for unsubstituted benzene rings (Itoh and Mase, Org. Lett. 6 (2004) 4587), and should work here as well. Deprotection of 22 with trifluoroacetic acid gives 23, which can be reacted with intermediate 9 (synthesis described in previously). Other thioethers should also be available from a similar route; e.g. by using the two thiophenes 11 and 12 (structures given above), and by employing other phenyl bromides than 20. Synthesis of the dicarbonyl compound 24 is shown in Scheme 9.

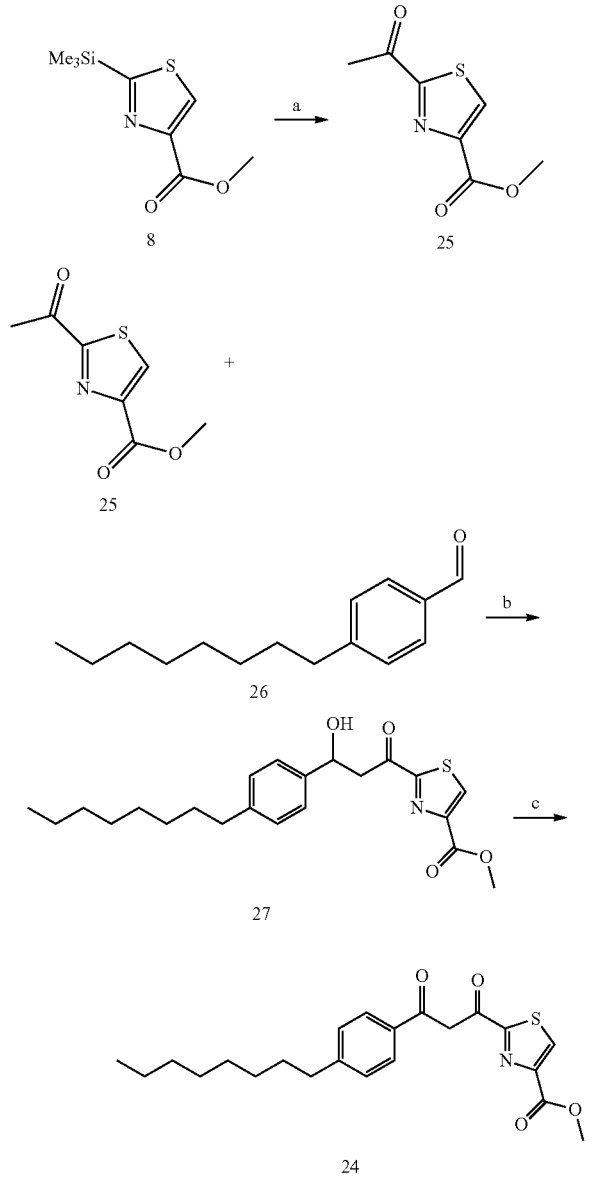

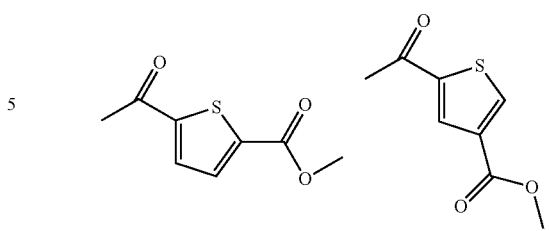

Intermediate 8 (described previously) is acetylated using acetyl chloride, using similar chemistry as for the preparation of 9. The resulting ketone 25 is reacted with p-octylbenzaldehyde (26, commercially available) in an aldol reaction to provide the β-hydroxyketone 27. Using mild oxidation conditions, the 1,3-dicarbonyl target compound 24 should be available.

Once more, further variations are easily accessible, e.g. by using other benzaldehydes than 26. Also, thiophene derivatives should be available by using the following intermediates (synthesis described previously):

EXAMPLE 4

Use of Compound A to Treat a Basal-like Cancer from a Patient

As described more fully below, we conducted a study in a patient-derived xenograft model of basal-like breast cancer, which is responsive to P3K inhibitors, is highly vascularised and has a high expression of cPLA2. The mice received 30 mg Compound A/kg bw by ip. injection daily for a 7 days, then every second day for 14 more days. A group of control mice received DMSO only. Tumor volumes were measured throughout the study period. At the end of the study, the tumor volume in mice treated with Compound A was 36% of the control tumors, which is comparable with the inhibitory effect of the dual PI3K/mTOR inhibitor BEZ235 in the same model.

A. Materials, Methods and Study Design

Mouse model: MAS98.12. This model is established from a primary breast carcinoma at the Institute for Cancer Research, OUS [10]. The MR Cancer Group has previously characterised this model both with respect to metabolic profile, vascularisation, response to antiangiogenic treatment and response to PI3K inhibition [9,11-13]. Treatment was initiated when the xenograft tumors had reached a volume of 83±51 mm3 (tumor volume=d1×d2×d2×6/π). The majority of mice had bilateral tumors.

B. Treatment: Mice received 30 mg/kg bw COMPOUND A in 50 µl DMSO, through intraperitoneal injection. Control groups received volume-matched, drug-free DMSO injections. Tumor volume measured with electronic callipers from day −3 until the end of the experiment (Day 19).

C. Study Design: Arm 1: Short-term treatment. One group (n=6, 11 tumors) treated with COMPOUND A daily for 2 days. Controls (n=6, 10 tumors) treated with drug-free DMSO according to the same protocol. The longest tumor diameter was 8-10 mm in all mice.

Arm 2: Long-term treatment One group (n=6, 11 tumors) treated with COMPOUND A daily for 7 days, then every 2nd day for the remainder of the study. Controls (n=6, 10 tumors) treated with drug-free DMSO according to the same protocol. At study start, the tumor volume was 67±31 mm3 in the COMPOUND A group and 103±65 mm3 in the control group (not significantly different). Throughout the study, the tumor volume was measured every 2-3 days, and the body weight of the mice was monitored regularly.

Collected material: At the end of the study (both arms), the following tissues were collected and preserved for further analysis:

Serum: approx 200 µl serum was collected from each mouse

Tumor tissue: All tumors were harvested. Large tumors were divided in 2 specimens, and stored in 4% NBF or snap frozen in liquid nitrogen. Small tumors were only snap frozen.

Spleen: The spleen of mice in the long-term treatment arm was collected and stored in 4% NBF.

D. Results—Long Term Treatment with Compound A

Clinical observations: During the experiment, we made the following observations: The animals were in good health during the study. No gross lesions or abnormalities were observed at the end of the study. No signs of irritation or damage was observed at the injection site (one mouse had a discoloration consistent with mechanical injury during injection). Visual inspection of tumors in mice treated with Compound A suggested a less blood-filled appearance, the tumors looked less aggressive and the skin covering the tumors was not stretched to the same extent as in the control group.

Body weight: Prior to the experiment, the mice were housed in a transit/quarantine unit as the health monitoring paperwork needed to be examined. The body weights could therefore not be recorded until day 5 after initiation of treatment. In the control group, the body weight increased from 23±2 g (Day 5) to 27±2 g (Day 19). In the COMPOUND A-treated group, the body weight increased from 24±3 g (Day 5) to 27±3 g (Day 19). This indicates that the COMPOUND A regimen was well tolerated.

Tumor volume: At the start of the experiment, the tumor volume in the control group was 103±65 mm$^3$. In the COMPOUND A group, the tumor volume was 67±31 mm$^3$. The difference was not statistically significant. At the end of the study (Day 19), the tumor volume in the control group was 759±401 mm$^3$, whereas the tumor volume in the COMPOUND A-treated group was 265±138 mm$^3$. The difference was statistically significant (t-test, p=0.001). In the control group, 2 mice were sacrificed at Day 12, due to tumor diameter>15 mm. At Day 19, 2 more mice had reached this limit, forcing the decision to terminate the study. At this time, 5 of 7 remaining tumors in the control group had a diameter≥11 mm, whereas the maximal tumors diameter in the COMPOUND A group was 10.5 mm.

In FIG. 1, the tumor volumes (normalised to the volume at initiation of treatment) are plotted together with data from a study in the same animal model, using the PI3K inhibitor BEZ235 [13]. This drug (Novartis Pharma) is currently in clinical phase I/II trials in advanced cancers. First, the figure demonstrates the inhibitory effect of COMPOUND A on tumor growth. Second, it shows that tumors in the control group in this pilot study had a growth rate similar to what we have seen in previous studies. Third, it shows that the therapeutic efficacy of COMPOUND A is similar to that of BEZ235. It is possible that a higher dose level of COMPOUND A could cause an even higher inhibitory effect on tumor growth.

The data in FIG. 1 show, among other things, that Compound A had a strong inhibitory effect on tumor growth in the patient-derived cancer xenograft MAS98.12. The compound was well tolerated with no overt adverse effects seen during the study. Tumor growth was significantly inhibited by Compound A. The growth rate of the control groups was similar to that of the PI3K inhibitor BEZ235 up to Day 12, when 2 mice were sacrificed (the remaining mice having smaller tumors). The inhibitory effect of Compound A was similar to BEZ235.

EXAMPLE 5

Compound Synthesis

GIVA cPLA$_2$ consists of an N-terminal C2 domain and a C-terminal catalytic domain and utilizes an unusual catalytic dyad (Ser-228/Asp-549) located in the α/β hydrolase domain to catalyze the hydrolysis of the substrates.[36] Without wishing to be bound to any theory, it is proposed that the activated ketone interacts with the catalytic serine. Although these two functionalities markedly differ in the potency of their activated carbonyl group, derivatives containing either the oxoamide or the fluoroketone functionality are efficient inhibitors of GIVA cPLA$_2$. Apparently, not only the potency of the activated carbonyl group, but also the presence of other groups able to present appropriate hydrophobic and/or hydrophilic interactions contribute to the overall binding of the inhibitor to enzyme, determining the inhibitory potency. In the present work, we study derivatives containing the oxothiazole functionality. The presence of the two heteroatoms on the heterocyclic ring helps the activation of the carbonyl group. In addition, the presence of an oxygen atom at the β-position enforces the activation. R$^1$ group may be either an aliphatic or an aromatic group, while a substituent R$^2$ may be present on the heterocyclic ring.

The synthesis of thiazole derivatives 32a,b and 37a-c is presented in Schemes 10 and 11. Phenols 28a,b and 33a,b were treated with ethyl bromoacetate. Esters 29a,b were hydrolyzed and converted to their corresponding Weinreb amides. Treatment of 31a,b with lithium thiazole led to the target derivatives 32a,b. Oxothiazoles 37a-c were prepared by another procedure. Alcohols 35a,b were oxidized to aldehydes and treated with lithium thiazole or benzothiazole. Compounds 36a-c were then oxidized to the final compounds.

Substituted thiazoles 43a-c and 47 (Compound A) were synthesized as illustrated in Schemes 12 and 13. The key-step in this synthesis was the formation of the substituted heterocyclic ring. Alcohols 35b and 38 were oxidized to aldehydes and directly treated with TBDMSCN. Compounds 39a,b were converted into amides and subsequently into thioamides by reaction with Lawesson's reagent. Treatment of 41a,b with ethyl 4-chloroacetoacetate or ethyl bromopyruvate in the presence of conc. H$_2$SO$_4$ led to heterocyclic derivatives 42a-c which were then oxidized to the final compounds 43a-c. Following another method for the formation of the heterocyclic ring, condensation of cysteine methyl ester with nitrile 39a afforded a diastereomeric mixture of thiazoline 44, which was transformed into thiazole 45 using BrCC13 and DBU. Subsequent removal of the silyl group and Dess-Martin oxidation led to the oxothiazole 47 (Compound A).

Scheme 10:

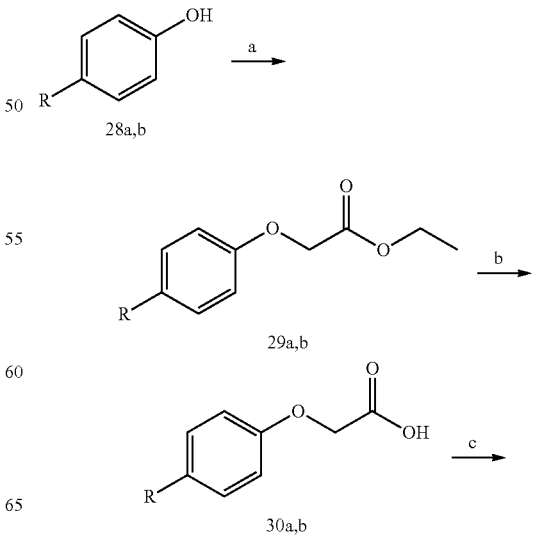

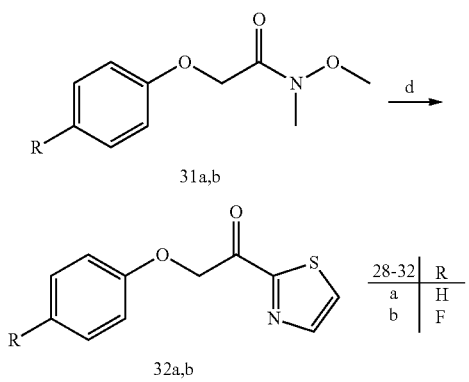

Scheme 10 Reagents and conditions: a) BrCH₂COOEt, K₂CO₃, acetone; b) 1N aq. NaOH, EtOH; c) HCl·HN(OMe)Me, NMM, DMAP, WSCI·HCl, CH₂Cl₂; d) thiazole, n-BuLi, Et₂O.

Scheme 11:

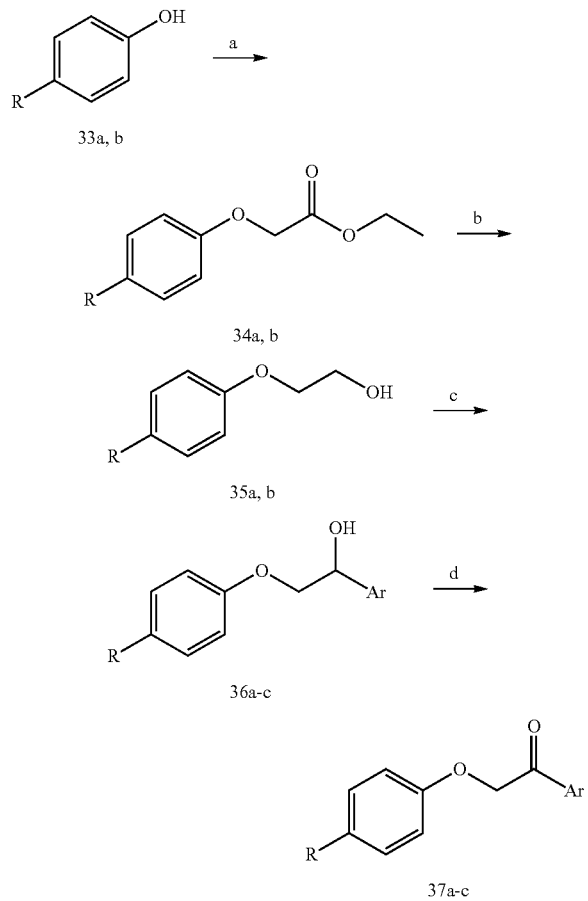

| 33-37 | R | Ar |
|---|---|---|
| a | C₆H₅ | thiazole |
| b | CH₃(CH₂)₇ | thiazole |
| c | CH₃(CH₂)₇ | benzothiazole |

Scheme 11 reagents and conditions: a) BrCH₂COOEt, K₂CO₃, acetone; b) DIBALH, Et₂O; c) NaOCl, TEMPO, NaBr, NaHCO₃, EtOAc/PhCH₃/H₂O 3:3:0.5, -5° C.; ii. thiazole or benzothiazole, n-BuLi, Et₂O; d) Dess-Martin periodinane, CH₂Cl₂.

Scheme 12:

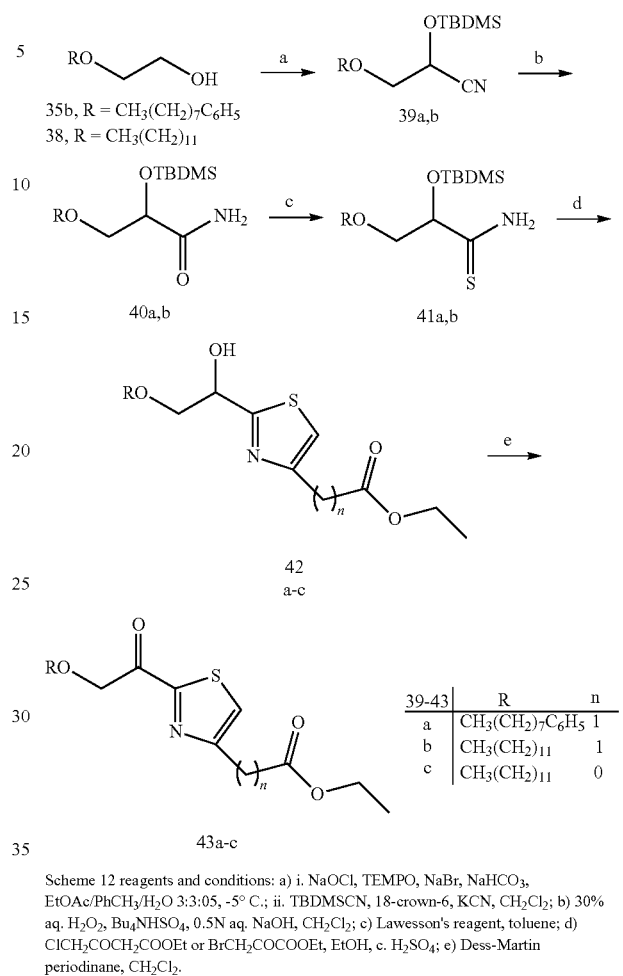

35b, R = CH₃(CH₂)₇C₆H₅
38, R = CH₃(CH₂)₁₁

| 39-43 | R | n |
|---|---|---|
| a | CH₃(CH₂)₇C₆H₅ | 1 |
| b | CH₃(CH₂)₁₁ | 1 |
| c | CH₃(CH₂)₁₁ | 0 |

Scheme 12 reagents and conditions: a) i. NaOCl, TEMPO, NaBr, NaHCO₃, EtOAc/PhCH₃/H₂O 3:3:05, -5° C.; ii. TBDMSCN, 18-crown-6, KCN, CH₂Cl₂; b) 30% aq. H₂O₂, Bu₄NHSO₄, 0.5N aq. NaOH, CH₂Cl₂; c) Lawesson's reagent, toluene; d) ClCH₂COCH₂COOEt or BrCH₂COCOOEt, EtOH, c. H₂SO₄; e) Dess-Martin periodinane, CH₂Cl₂.

Scheme 13:

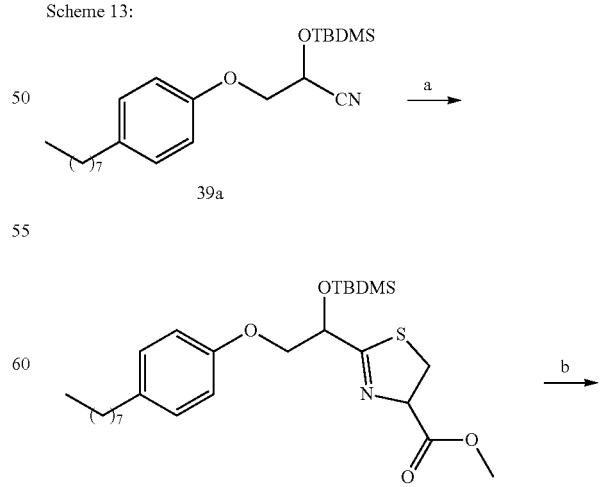

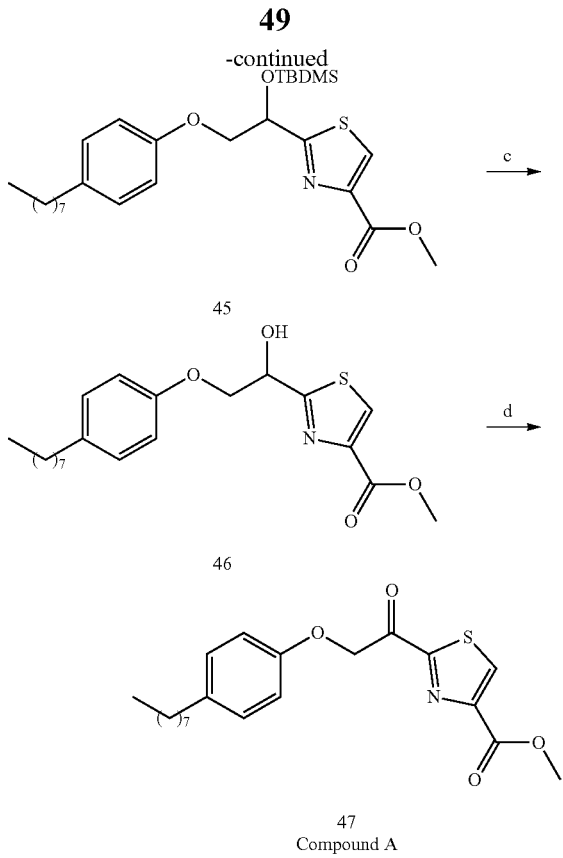

Scheme 13 reagents and conditions: a) HCl·H—L-Cys—OMe; CH₃COO⁻NH₄⁺, MeOH; b) DBU, BrCCl₃, CH₂Cl₂; c) 4N HCl/MeOH; d) Dess-Martin periodinane, CH₂Cl₂.

Materials and Methods

The following materials, methods and information will be useful in appreciating example 5.

General. Melting points were determined using Büichi 530 and were uncorrected. NMR spectra were recorded on a Varian Mercury spectrometer. $^1$H and $^{13}$C NMR spectra were recorded at 200 MHz and 50 MHz respectively in CDCl₃ or as specified. Chemical shifts are given in ppm, and coupling constants (J) in Hz. Peak multiplicities are described as follows: s, singlet, d, doublet, t, triplet and m, multiplet. Electron spray ionization (ESI) mass spectra were recorded on a Finnigan, Surveyor MSQ Plus spectrometer. TLC plates (Silica Gel 60 F254) and Silica Gel 60 (70-230 or 230-400 mesh) for column chromatography were purchased from Merck. Spots were visualised with UV light and/or phosphomolybdic acid in EtOH. Dichloromethane, diethylether and toluene were dried by standard procedures and stored over molecular sieves. All other solvents and chemicals were reagent grade and used without further purification.

Compounds 29b,[59] 31a,[60] 31b,[61] 34,[62] have been described elsewhere and their analytical data is in accordance with literature.

Ethyl 2-(4-octylphenoxy)acetate (34b). To a stirred solution of the 4-n-octylphenol (1.0 mmol, 206 mg) in acetone (10 mL), K₂CO₃ (3 mmol, 415 mg) and ethyl bromoacetate (1.1 mmol, 215 mg) were added, and the reaction mixture was refluxed for 5 h. Subsequently, the mixture was filtrated over Celite, and the organic solvent was evaporated under reduced pressure. The residue was purified by flash column chromatography [EtOAc-petroleum ether (bp 40-60° C.), 1:9]. Yield 98%; White oil; $^1$H NMR (200 MHz, CDCl₃): δ 7.10 (2H, d, J=8.4 Hz, 2×CH Ar), 6.84 (2H, d, J=8.4 Hz, 2×CH Ar), 4.60 (2H, s, CH₂), 4.28 (2H, q, J=7.2 Hz, CH₂), 2.55 (2H, t, J=7.8 Hz, CH₂Ph), 1.69-1.46 (2H, m, CH₂), 1.45-1.11 (13H, m, 5×CH₂, CH₃), 0.89 (3H, t, J=7.0 Hz, CH₃); $^{13}$C NMR (50 MHz, CDCl₃): δ 169.11, 155.77, 136.14, 129.28, 114.37, 65.52, 61.25, 35.00, 31.84, 31.63, 29.44, 29.23, 22.63, 14.09; MS (ESI) m/z (%): 293.3 (90) [M+H]⁺.

Synthesis of alcohols 35a,b. To a stirred solution of the esters 34a,b (1 mmol) in dry Et₂O (10 mL) was added DIBALH (2.5 mL, 2.5 mmol, 1.0 M in hexane) at 0° C. under Ar atmosphere and the reaction mixture was stirred for 2 h at room temperature. Water was then added (5 mL), the mixture was stirred for 30 more minutes and filtrated over Celite. The organic solvent was evaporated under reduced pressure and the residue was purified by flash column chromatography [EtOAc-petroleum ether (bp 40-60° C.), 3:7].

2-(Biphenyl-4-yloxy)ethanol (35a). Yield 94%; White solid; mp 120-122° C.; $^1$H NMR (200 MHz, CDCl₃): δ 7.63-7.22 (7H, m, 7×CH), 7.07-6.94 (2H, m, 2×CH), 4.19-4.07 (2H, m, CH₂), 4.05-3.94 (2H, m, CH₂), 1.91 (1H, br, OH); $^{13}$C NMR (50 MHz, CDCl₃): δ 158.08, 140.60, 134.15, 128.70, 128.18, 126.69, 114.76, 69.19, 61.44.

2-(4-Octylphenoxy)ethanol (35b). Yield 82%; White solid; mp 40-42° C.; $^1$H NMR (200 MHz, CDCl₃): δ 7.11 (2H, d, J=8.6 Hz, 2×CH Ar), 6.85 (2H, d, J=8.6 Hz, 2×CH Ar), 4.07 (2H, t, J=4.4 Hz, CH₂), 3.96 (2H, t, J=4.4 Hz, CH₂), 2.56 (2H, t, J=7.8 Hz, CH₂Ph), 2.19 (1H, br, OH), 1.70-1.48 (2H, m, CH₂), 1.45-1.14 (13H, m, 5×CH₂, CH₃), 0.90 (3H, t, J=7.0 Hz, CH₃); $^{13}$C NMR (50 MHz, CDCl₃): δ 156.51, 135.54, 129.28, 114.33, 114.24, 69.10, 61.48, 35.01, 31.86, 31.73, 29.46, 29.24, 22.65, 14.10.

Synthesis of ketones 32a,b. To a stirred solution of thiazole (3 eq.) in dry Et₂O (20 mL) at −78° C. under a dry argon atmosphere was added a solution of n-BuLi (1.6 M in hexanes, 3 eq.) dropwise over a period of 10 min. The resulting orange solution was stirred for 45 min. Then a solution of the amide 31a,b (1 mmol) in dry Et₂O (2 mL) was slowly added giving the mixture a dark brown colour. After stirring for 30 min. at −78° C., the mixture was allowed to warm up to room temperature over a period of 2 h. Then, saturated aqueous ammonium chloride solution was added and the mixture was extracted with ether (2×10 mL). The combined extracts were washed with brine and then dried over Na₂SO₄ and concentrated under reduced pressure. Purification by flash chromatography eluting with the appropriate mixture of [EtOAc-petroleum ether (bp 40-60° C.)] afforded the desired product.

2-Phenoxy-1-(thiazol-2-yl)ethanone (Compound D, 32a). Yield 54%; White solid; mp 77-79° C.; $^1$H NMR (200 MHz, CDCl₃): δ 8.06 (1H, d, J=3.0 Hz, CH Ar), 7.77 (1H, d, J=3.0 Hz, CH Ar), 7.39-7.22 (2H, m, 2×CH Ar), 7.07-6.93 (2H, m, 3×CH Ar), 5.55 (2H, s, CH₂); $^{13}$C NMR (50 MHz, CDCl₃): δ 187.38, 163.96, 157.82, 144.94, 129.49, 126.71, 121.63, 114.78, 69.97; MS (ESI) m/z (%): 220.0 (100) [M+H]⁺.

2-(4-Fluorophenoxy)-1-(thiazol-2-yl)ethanone (Compound C, 32b). Yield 61%; White solid; mp 74-77° C.; $^1$H NMR (200 MHz, CDCl₃): δ 8.06 (1H, d, J=3.0 Hz, CH Ar), 7.78 (1H, d, J=3.0 Hz, CH Ar), 7.09-6.86 (4H, m, 4×CH Ar), 5.51 (2H, s, CH₂); $^{13}$C NMR (50 MHz, CDCl₃): δ 187.35, 163.95, 160.15, 155.39, 154.07, 145.02, 126.80, 116.18, 115.87 (d, J=15.8 Hz), 70.80; MS (ESI) m/z (%): 238.1 (100) [M+H]⁺.

Synthesis of alcohols 36a-c. To a solution of the alcohols 35a,b (1.0 mmol) in a mixture of toluene (3 mL) and EtOAc (3 mL), a solution of NaBr (0.11 g, 1.1 mmol) in water (0.5 mL) was added followed by AcNH-TEMPO (2.2 mg, 0.01 mmol). To the resulting biphasic system, which was cooled at 0° C., an aqueous solution of 0.35 M NaOCl (3.1 mL, 1.1 mmol) containing NaHCO$_3$ (0.25 g, 3 mmol) was added dropwise under vigorous stirring, at 0° C. over a period of 1 h. After the mixture had been stirred for a further 15 min at 0° C., EtOAc (10 mL) and H$_2$O (10 mL) were added. The aqueous layer was separated and washed with EtOAc (2×10 mL). The combined organic layers were washed consecutively with 5% aqueous citric acid (10 mL) containing KI (0.04 g), 10% aqueous Na$_2$S$_2$O$_3$ (10 mL), and brine and dried over Na$_2$SO$_4$. The solvents were evaporated under reduced pressure and the residue was used without any further purification. To a stirred solution of thiazole (3 eq.) in dry Et$_2$O (20 mL) at −78° C. under a dry argon atmosphere was added a solution of n-BuLi (1.6 M in hexanes, 3 eq.) drop-wise over a period of 10 min. The resulting orange solution was stirred for 45 min. Then a solution of the above prepared aldehyde (1 mmol) in dry Et$_2$O (2 mL) was slowly added giving the mixture a dark brown colour. After stirring for 30 min. at −78° C., the mixture was allowed to warm up to room temperature over a period of 2 h. Then, saturated aqueous ammonium chloride solution was added and the mixture was extracted with ether (2×10 mL). The combined extracts were washed with brine and then dried over Na$_2$SO$_4$ and concentrated under reduced pressure. Purification by flash chromatography eluting with the appropriate mixture of EtOAc-petroleum ether (bp 40-60° C.) afforded the desired product.

2-(Biphenyl-4-yloxy)-1-(thiazol-2-yl)ethanol (36a). Yield 48%; Pale yellow solid; mp 93-95° C.; $^1$H NMR (200 MHz, CDCl$_3$): δ 7.79 (1H, d, J=3.2 Hz, CH Ar), 7.67-7.22 (7H, m, 7×CH Ar), 7.09-6.93 (3H, m, 3×CH Ar), 5.44 (1H, dd, J$_1$=3.9 Hz, J$_2$=7.0 Hz, CH), 4.49 (1H, dd, J$_1$=3.9 Hz, J$_2$=9.7 Hz, CHH), 4.30 (1H, dd, J$_1$=7.0 Hz, J$_2$=9.7 Hz, CHH); $^{13}$C NMR (50 MHz, CDCl$_3$): δ 170.88, 157.66, 142.41, 140.53, 134.53, 128.69, 128.19, 126.75, 126.70, 119.59, 114.99, 71.60, 70.62; MS (ESI) m/z (%): 297.8 (100) [M+H]$^+$.

2-(4-Octylphenoxy)-1-(thiazol-2-yl)ethanol (36b). Yield 34%; Yellow oil; $^1$H NMR (200 MHz, CDCl$_3$): δ 7.78 (1H, d, J=3.2 Hz, CH Ar), 7.34 (1H, d, J=3.2 Hz, CH Ar), 7.09 (2H, d, J=8.6 Hz, 2×CH Ar), 6.86 (2H, d, J=8.6 Hz, 2×CH Ar), 5.40 (1H, dd, J$_1$=3.8 Hz, J$_2$=7.0 Hz, CH), 4.42 (1H, dd, J$_1$=4.0 Hz, J$_2$=9.6 Hz, CHH), 4.22 (1H, dd, J$_1$=7.0 Hz, J$_2$=9.6 Hz, CHH), 2.54 (2H, t, J=7.8 Hz, CH$_2$Ph), 1.69-1.45 (2H, m, CH$_2$), 1.43-1.10 (10H, m, 5×CH$_2$), 0.89 (3H, t, J=7.0 Hz, CH$_3$); $^{13}$C NMR (50 MHz, CDCl$_3$): δ 170.98, 156.10, 142.36, 135.94, 129.30, 119.48, 114.49, 71.56, 70.65, 35.00, 31.84, 31.66, 29.43, 29.22, 22.62, 14.06; MS (ESI) m/z (%): 334.2 (100) [M+H]$^+$.

1-(Benzo[d]thiazol-2-yl)-2-(4-octylphenoxy)ethanol (36c). Yield 42%; Yellow solid; mp 93-95° C.; $^1$H NMR (200 MHz, CDCl$_3$): δ 8.10-7.97 (1H, m, CH Ar), 7.96-7.82 (1H, m, CH Ar), 7.56-7.32 (2H, m, 2×CH Ar), 7.09 (2H, d, J=8.5 Hz, 2×CH Ar), 6.88 (2H, d, J=8.5 Hz, 2×CH Ar), 5.50 (1H, dd, J$_1$=4.0 Hz, J$_2$=6.8 Hz, CH), 4.52 (1H, dd, J$_1$=4.0 Hz, J$_2$=9.7 Hz, CHH), 4.34 (1H, dd, J$_1$=6.8 Hz, J$_2$=9.7 Hz, CHH), 2.55 (2H, t, J=7.8 Hz, CH$_2$Ph), 1.70-1.47 (2H, m, CH$_2$), 1.45-1.12 (10H, m, 5×CH$_2$), 0.89 (3H, t, J=7.0 Hz, CH$_3$); $^{13}$C NMR (50 MHz, CDCl$_3$): δ 172.24, 156.04, 152.81, 135.98, 134.91, 129.29, 126.22, 126.05, 125.48, 125.04, 123.54, 122.91, 121.76, 114.51, 71.37, 71.01, 35.00, 31.84, 31.65, 29.43, 29.22, 22.62, 14.07; MS (ESI) m/z (%): 384.2 (100) [M+H]$^+$.

Synthesis of nitriles 39a,b. To a mixture of tert-butyldimethylsilyl cyanide (1.0 mmol, 141 mg), potassium cyanide (0.2 mmol, 13 mg), and 18-crown-6 (0.4 mmol, 106 mg) was added dropwise a solution of the aldehyde (1.0 mmol) in CH$_2$Cl$_2$ at room temperature under nitrogen over 30 min. After addition was complete, the mixture was stirred overnight at room temperature. The organic solvent was evaporated under reduced pressure and the residue was purified by flash column chromatography [EtOAc-petroleum ether (bp 40-60° C.), 1:9].

2-(tert-Butyldimethylsilyloxy)-3-(4-octylphenoxy)propanenitrile (39a). Yield 93%; White oil; $^1$H NMR (200 MHz, CDCl$_3$): δ 7.12 (d, J=8.4 Hz, 2H, 2×CH Ar), 6.84 (d, J=8.8 Hz, 2H, 2×CH arom.), 4.80 (t, J=5.4 Hz, 1H, CH), 4.21-3.98 (m, 2H, CH$_2$), 2.56 (t, J=7.8 Hz, 2H, CH$_2$), 1.65-1.42 (m, 2H, CH$_2$), 1.40-1.13 (br s, 10H, 5×CH$_2$), 1.04-0.75 [m, 12H, (CH$_3$)$_3$, CH$_3$], 0.24 (s, 3H, CH$_3$), 0.19 (s, 3H, CH$_3$); $^{13}$C NMR (50 MHz, CDCl$_3$): δ 155.75, 136.25, 129.37, 118.14, 114.42, 69.63, 61.51, 35.02, 31.86, 31.69, 29.45, 29.22, 25.44, 22.65, 18.10, 14.10, −5.27; MS (ESI) m/z (%): 407.3 (100) [M+NH$_4$]+.

2-(tert-Butyldimethylsilyloxy)-3-(dodecyloxy)propanenitrile (39b). Yield 72%; White oil; $^1$H NMR (200 MHz, CDCl$_3$): δ 4.55 (t, J=6.4 Hz, 1H, CH), 3.62 (d, J=6.6 Hz, 2H, CH$_2$), 3.52 (t, J=6.6 Hz, CH$_2$), 1.67-1.48 (m, 2H, CH$_2$), 1.26 (br s, 18H, 9×CH$_2$), 0.98-1.82 [m, 12H, C(CH$_3$)$_3$, CH$_3$], 0.19 (s, 3H, CH$_3$), 0.17 (s, 3H, CH$_3$); $^{13}$C NMR (50 MHz, CDCl$_3$): δ 118.72, 72.57, 72.17, 62.01, 31.88, 29.60, 29.54, 29.38, 29.32. 25.94, 25.45, 22.66, 18.06, 14.09, −5.28, −5.33; MS (ESI) m/z (%): 387.3 (100) [M+NH$_4$]$^+$.

Synthesis of amides 40a,b. To a solution of nitriles 39a,b (1 mmol) and Bu$_4$NHSO$_4$ (0.2 mmol, 68 mg) in CH$_2$Cl$_2$ (10 mL), was added dropwise a solution of 0.5 N aq. NaOH (2.5 mL) and 30% H$_2$O$_2$ (4 mmol, 3.5 mL) at 0° C. The biphasic reaction mixture was stirred overnight at room temperature. The organic layer was separated, washed with water (2×10 mL) and dried over Na$_2$SO$_4$. Organic solvent was evaporated under reduced pressure and the residue was purified by flash column chromatography [EtOAc-petroleum ether (bp 40-60° C.)].

2-(tert-Butyldimethylsilyloxy)-3-(4-octylphenoxy)propanamide (40a). Yield 68%; White solid; mp 56-58° C.; $^1$H NMR (200 MHz, CDCl$_3$): δ 7.08 (d, J=8.4 Hz, 2H, 2×CH Ar), 6.82 (d, J=8.8 Hz, 2H, 2×CH arom.), 6.77 (br s, 1H, NHH), 6.08 (br s, 1H, NHH), 4.51 (dd, J=7.2 Hz, J$_2$=2.2 Hz, 1H, CH), 4.32 (dd, J=10.4 Hz, J$_2$=2.2 Hz, 1H, CHH), 4.03 (dd, J$_1$=10.0 Hz, J$_2$=7.4 Hz, 1H, CHH), 2.53 (t, J=7.8 Hz, 2H, CH$_2$), 1.63-1.42 (m, 2H, CH$_2$), 1.39-1.07 (br s, 10H, 5×CH$_2$), 0.99-0.73 [m, 12H, (CH$_3$)$_3$, CH$_3$], 0.17 (s, 3H, CH$_3$), 0.16 (s, 3H, CH$_3$); $^{13}$C NMR (50 MHz, CDCl$_3$): δ 174.16, 156.40, 135.43, 129.23, 114.24, 73.35, 70.74, 35.02, 31.86, 31.72, 29.46, 29.26, 25.76, 22.65, 18.13, 14.11, −4.50, −5.33; MS (ESI) m/z (%): 408.3 (100) [M+H]$^+$.

2-(tert-Butyldimethylsilyloxy)-3-(dodecyloxy)propanamide (40b). Yield 79%; White oil; $^1$H NMR (200 MHz, CDCl$_3$): δ 6.66 (br s, 1H, NHH), 6.60 (br s, 1H, NHH), 4.24 (dd, J$_1$=6.2 Hz, J$_2$=2.2, 1H, CH), 3.67 (dd, J=10.0 Hz, J$_2$=2.2, 1H, CHH), 3.52 (dd, J$_1$=10.0 Hz, J$_2$=6.2 Hz, 1H, CHH), 3.41 (t, J=6.2 Hz, 2H, CH$_2$), 1.63-1.45 (m, 2H, CH$_2$), 1.24 (br s, 18H, 9×CH$_2$), 1.02-1.79 [m, 12H, C(CH$_3$)$_3$, CH$_3$], 0.11 (s, 6H, 2×CH$_3$); $^{13}$C NMR (50 MHz, CDCl$_3$): δ 175.04, 74.02, 73.45, 71.59, 31.86, 29.57, 29.54, 29.48, 29.38, 29.29, 26.01, 25.72, 22.62, 18.10, 14.06, −4.69, −5.42; MS (ESI) m/z (%): 388.2 (100) [M+H]$^+$.

Synthesis of thioamides 41a,b. Lawesson's reagent (0.6 mmol, 243 mg) was added to a solution of amides 40a,b (1 mmol) in dry toluene (10 mL) under argon atmosphere. The reaction mixture was stirred at room temperature overnight. The solvent was evaporated under reduced pressure and the residue was purified by flash chromatography eluting with the appropriate mixture of EtOAc/petroleum ether (bp 40-60° C.).

2-(tert-Butyldimethylsilyloxy)-3-(4-octylphenoxy)propanethioamide (41a). Yield 40%; Pale yellow oil; $^1$H NMR (200 MHz, CDCl$_3$): δ 8.22 (br s, 1H, NHH), 7.83 (br s, 1H, NHH), 7.09 (d, J=8.8 Hz, 2H, 2×CH arom.), 6.84 (d, J=8.8 Hz, 2H, 2×CH arom.), 4.89 (dd, $J_1$=7.4 Hz, $J_2$=2.2 Hz, 1H, CHH), 4.55 (dd, $J_1$=9.8 Hz, $J_2$=2.2 Hz, 1H, CHH), 4.03 (dd, $J_1$=10.0 Hz, $J_2$=7.4 Hz, 1H, CH), 2.54 (t, J=7.4 Hz, 2H, CH$_2$), 1.63-1.41 (m, 2H, CH$_2$), 1.39-1.05 (m, 10H, 5×CH$_2$), 1.02-0.69 [m, 12H, (CH$_3$)$_3$, CH$_3$], 0.16 (s, 6H, 3×CH$_3$); $^{13}$C NMR (50 MHz, CDCl$_3$): δ 205.41, 156.33, 135.46, 129.24, 114.28, 79.25, 72.62, 35.01, 31.85, 31.70, 29.45, 29.23, 25.76, 25.27, 22.64, 18.20, 14.10, −4.58, −5.24; MS (ESI) m/z (%): 424.1 (100) [M+H]$^+$.

2-(tert-Butyldimethylsilyloxy)-3-(dodecyloxy)propanethioamide (41b). Yield 39%; Pale yellow oil; $^1$H NMR (200 MHz, CDCl$_3$): δ 8.12 (br s, 1H, NHH), 7.97 (br s, 1H, NHH), 4.65 (dd, $J_1$=6.2 Hz, $J_2$=2.6, 1H, CH), 3.88 (dd, $J_1$=10.2 Hz, $J_2$=2.6, 1H, CHH), 3.58 (dd, $J_1$=10.0 Hz, $J_2$=6.2 Hz, 1H, CHH), 3.51-3.38 (m, 2H, CH$_2$), 1.63-1.45 (m, 2H, CH$_2$), 1.25 (br s, 18H, 9×CH$_2$), 1.05-1.82 [m, 12H, C(CH$_3$)$_3$, CH$_3$], 0.14 (s, 6H, 2×CH$_3$); $^{13}$C NMR (50 MHz, CDCl$_3$): δ 206.27, 80.12, 75.36, 71.73, 31.86, 29.55, 29.41, 29.30, 26.04, 25.75, 25.26, 22.63, 18.19, 14.08, −4.70, −5.26; MS (ESI) m/z (%): 404.3 (100) [M+H]$^+$.

Synthesis of thiazoles 42a-c. To a stirred solution of thioamides 41a,b (1.0 mmol) in EtOH (5 mL) was added ethyl bromopyruvate (1.2 mmol, 0.15 mL) or ethyl 4-chloroacetoacetate (1.0 mmol, 0.14 mL) and c. H$_2$SO$_4$ (0.04 mL), and the reaction mixture was refluxed overnight. Organic solvent was evaporated under reduced pressure and the residue was purified by flash column chromatography [EtOAc-petroleum ether (bp 40-60° C.)].

Ethyl 2-(2-(1-hydroxy-2-(4-octylphenoxy)ethyl)thiazol-4-yl)acetate (42a). Yield 17%; Yellowish oil; $^1$H NMR (200 MHz, CDCl$_3$): δ 7.20 (s, 1H, CHS), 7.09 (d, J=8.4 Hz, 2×CH), 6.85 (d, J=8.4 Hz, 2×CH), 5.35 (dd, J=7.0 Hz, $J_2$=4.0, 1H, CH), 4.38 (dd, J=9.6 Hz, $J_2$=4.0, 1H, CHH), 4.31-4.09 (m, 3H, COOCH$_2$, CHH), 3.82 (s, 2H, CH$_2$COO), 2.54 (t, J=7.4 Hz, 2H, CH$_2$Ph), 1.69-1.45 (m, 2H, CH$_2$), 1.43-1.18 (m, 13H, 5×CH$_2$, CH$_3$), 0.88 (t, J=7.0 Hz, 3H); $^{13}$C NMR (50 MHz, CDCl$_3$): δ 170.46, 170.31, 156.06, 148.49, 135.97, 129.30, 116.74, 114.48, 71.50, 70.60, 61.08, 36.89, 35.01, 31.84, 31.68, 29.43, 29.23, 22.63, 14.08; MS (ESI) m/z (%): 420.1 (100) [M+H]$^+$.

Ethyl 2-(2-(2-(dodecyloxy)-1-hydroxyethyl)thiazol-4-yl)acetate (42b). Yield 26%; Yellow solid; $^1$H NMR (200 MHz, CDCl$_3$): δ 7.16 (s, 1H, CHS), 5.12 (dd, J=6.8 Hz, $J_2$=3.6 Hz, 1H, CH), 4.18 (q, J=7.4 Hz, COOCH$_2$), 3.83 (dd, J=10.0 Hz, $J_2$=3.8 Hz, 1H, CHH), 3.80 (s, 2H, CH$_2$), 3.70-3.42 (m, 4H, CHH, CH$_2$, OH), 1.65-1.46 (m, 2H, CH$_2$), 1.40-1.12 (m, 21H, 9×CH$_2$, CH$_3$), 0.87 (t, J=6.8 Hz, 3H, CH$_3$); $^{13}$C NMR (50 MHz, CDCl$_3$): δ 171.31, 170.30, 148.42, 116.31, 74.10, 71.67, 70.87, 61.00, 36.96, 31.87, 29.56, 29.47, 29.38, 29.31, 25.98, 22.64, 14.08; MS (ESI) m/z (%): 400.1 (100) [M+H]$^+$.

Ethyl 2-(2-(dodecyloxy)-1-hydroxyethyl)thiazole-4-carboxylate (42c). Yield 68%; Low mp off-white solid; $^1$H NMR (200 MHz, CDCl$_3$): δ 8.14 (s, 1H, CHS), 5.20 (dd, $J_1$=6.6 Hz, $J_2$=3.8 Hz, 1H, CH), 4.41 (q, J=7.4 Hz, COOCH$_2$), 3.92 (dd, $J_1$=9.8 Hz, $J_2$=3.6 Hz, 1H, CHH), 3.66 (dd, $J_1$=9.8 Hz, $J_2$=7.0 Hz, 1H, CHH), 3.60-3.42 (m, 3H, CH$_2$, OH), 1.68-1.19 (m, 23H, 10×CH$_2$, CH$_3$), 0.87 (t, J=6.6 Hz, 3H, CH$_3$); $^{13}$C NMR (50 MHz, CDCl$_3$): δ 172.97, 161.37, 146.95, 127.62, 73.68, 71.67, 70.89, 61.39, 31.86, 29.57, 29.54, 29.42, 29.35, 29.29, 25.95, 22.63, 14.32, 14.06; MS (ESI) m/z (%): 386.3 (100) [M+H]$^+$.

Methyl 2-(1-(tert-butyldimethylsilyloxy)-2-(4-octylphenoxy)ethyl)-4,5-dihydrothiazole-4-carboxylate (mixture of diastereomers) (44). To a stirred solution of 39a (1.0 mmol, 390 mg) and CH$_3$COO$^-$NH$_4^+$ (3.6 mmol, 277 mg) in MeOH (4 mL), HCl.H-Cys-OMe (3.0 mmol, 515 mg) was added, and the mixture was stirred overnight at room temperature. The organic solvent was evaporated under reduced pressure and the residue was purified by flash column chromatography [EtOAc-petroleum ether (bp 40-60° C.), 1:9]. Yield 67%; White oil; $^1$H NMR (200 MHz, CDCl$_3$): δ 7.07 (2H, d, J=8.4 Hz, 2×CH Ar), 6.82 (2H, d, J=8.4 Hz, 2×CH Ar), 5.25-5.07 (1H, m, CH), 5.06-4.90 (1H, m, CH), 4.38-4.15 (1H, m, CHH), 4.14-3.94 (1H, m, CHH), 3.82 (3H, s, CH$_3$), 3.63-3.33 (2H, m, CH$_2$), 2.64-2.43 (2H, t, J=7.8 Hz, CH$_2$), 1.70-1.45 (2H, m, CH$_2$), 1.43-1.16 (10H, br s, 5×CH$_2$), 1.05-0.80 (12H, m, 4×CH$_3$), 0.22-0.10 (6H, m, 2×CH$_3$); $^{13}$C NMR (50 MHz, CDCl$_3$): δ 178.61, 171.06, 156.44, 135.26, 129.11, 114.27, 78.35, 72.50, 72.45, 71.52, 52.68, 52.65, 34.99, 33.69, 31.82, 31.68, 29.42, 29.21, 25.65, 22.61, 18.24, 14.06, −4.69, −5.21; MS (ESI) m/z (%): 508.4 (100) [M+H]$^+$.

Methyl 2-(1-(tert-butyldimethylsilyloxy)-2-(4-octylphenoxy)ethyl)thiazole-4-carboxylate (45). A solution of 44 (1 mmol, 508 mg), BrCCl$_3$ (6.0 mmol, 0.59 mL) and DBU (6.0 mmol, 0.90 mL) in CH$_2$Cl$_2$ (20 mL) was stirred overnight at room temperature. The organic solvent was evaporated under reduced pressure and the residue was purified by flash column chromatography [EtOAc-petroleum ether (bp 40-60° C.), 1:9]. Yield 82%; White oil; $^1$H NMR (200 MHz, CDCl$_3$): δ 8.18 (1H, s, SCH), 7.15-7.00 (2H, m, 2×CH Ar), 6.89-6.75 (2H, m, 2×CH Ar), 5.53-5.40 (1H, m, CH), 4.51-4.37 (1H, m, CHH), 4.12-3.90 (4H, m, CHH, CH$_3$), 2.54 (2H, t, J=7.8 Hz, CH$_2$), 1.70-1.45 (2H, m, CH$_2$), 1.44-1.14 (10H, br s, 5×CH$_2$), 1.07-0.79 (12H, m, 4×CH$_3$), 0.26-0.09 (6H, m, 2×CH$_3$); $^{13}$C NMR (50 MHz, CDCl$_3$): δ 174.53, 161.91, 156.46, 146.83, 135.45, 129.30, 129.19, 127.97, 114.32, 72.74, 72.58, 52.43, 35.03, 31.86, 31.69, 29.46, 29.25, 25.71, 22.65, 18.25, 14.09, −4.48, −5.17; MS (ESI) m/z (%): 506.5 (100) [M+H]$^+$.

Methyl 2-(1-hydroxy-2-(4-octylphenoxy)ethyl)thiazole-4-carboxylate (46) Compound 45 (1.0 mmol, 505 mg) was treated with a solution of 4N HCl in MeOH. The organic solvent was evaporated under reduced pressure and the residue was recrystallized from ether. Yield 95%; White solid; mp 84-86° C.; $^1$H NMR (200 MHz, CDCl$_3$): δ 8.18 (1H, s, SCH), 7.06 (2H, d, J=8.0 Hz, 2×CH Ar), 6.82 (2H, d, J=8.0 Hz, 2×CH Ar), 5.60-5.28 (1H, br s, CH), 4.61-3.75 (6H, m, CH$_2$, CH$_3$, OH), 2.52 (2H, t, J=7.8 Hz, CH$_2$), 1.69-1.43 (2H, m, CH$_2$), 1.42-1.11 (10H, br s, 5×CH$_2$), 0.88 (3H, t, J=6.8 Hz, CH$_3$); $^{13}$C NMR (50 MHz, CDCl$_3$): δ 172.42, 161.70, 155.83, 146.45, 135.99, 129.23, 128.23, 128.17, 114.40, 71.21, 70.62, 52.46, 34.93, 31.77, 31.61, 29.37, 29.16, 22.56, 14.03; MS (ESI) m/z (%): 392.2 (100) [M+H]$^+$.

Synthesis of thiazoles 37a-c, 43a-c and 47. To a solution of the compounds 36a-c, 42a-c and 46 (1 mmol) in dry CH$_2$Cl$_2$ (10 mL) Dess-Martin periodinane was added (1.5 mmol, 637 mg) and the mixture was stirred for 1 h at room temperature. The organic solvent was evaporated under reduce pressure and Et$_2$O (30 mL) was added. The organic phase was washed with saturated aqueous NaHCO$_3$ (20 mL) containing Na$_2$S$_2$O$_3$ (1.5 g, 9.5 mmol), H$_2$O (20 mL), dried over Na$_2$SO$_4$, and the organic solvent was evaporated under reduced pressure. The residue was purified by column chromatography using petroleum ether (bp 40-60° C.)/EtOAc as eluent.

2-(Biphenyl-4-yloxy)-1-(thiazol-2-yl)ethanone (Compound B, 37a). Yield 82%; White solid; mp 130-133° C.; $^1$H NMR (200 MHz, CDCl$_3$): δ 8.09-8.03 (1H, m, CH Ar), 7.80-7.74 (1H, m, CH Ar), 7.63-7.23 (8H, m, 8×CH Ar), 7.12-7.00 (2H, m, 2×CH Ar), 5.57 (2H, s, CH$_2$); $^{13}$C NMR (50 MHz, CDCl$_3$): δ 187.38, 157.47, 145.01, 140.60, 134.83, 128.69, 128.25, 126.77, 115.13, 70.17; MS (ESI) m/z (%): 296.0 (100) [M+H]$^+$.

2-(4-Octylphenoxy)-1-(thiazol-2-yl)ethanone (Compound T3, 37b). Yield 79%; White solid; mp 65-67° C.; $^1$H NMR (200 MHz, CDCl$_3$): δ 8.06 (1H, d, J=3.0 Hz, CH Ar), 7.76 (1H, d, J=3.0 Hz, CH Ar), 7.11 (2H, d, J=8.4 Hz, 2×CH Ar), 6.92 (2H, d, J=8.4 Hz, 2×CH Ar), 5.52 (2H, s, CH$_2$), 2.55 (2H, t, J=7.8 Hz, CH$_2$Ph), 1.71-1.46 (2H, m, CH$_2$), 1.42-1.10 (10H, m, 5×CH$_2$), 0.89 (3H, t, J=7.0 Hz, CH$_3$); $^{13}$C NMR (50 MHz, CDCl$_3$): δ; MS (ESI) m/z (%): 332.1 (100) [M+H]$^+$.

1-(Benzo[d]thiazol-2-yl)-2-(4-octylphenoxy)ethanone (37c, Compound V). Yield 75%; White solid; mp 80-82° C.; $^1$H NMR (200 MHz, CDCl$_3$): δ 8.26-8.17 (1H, m, CH Ar), 8.08-7.96 (1H, m, CH Ar), 7.69-7.51 (2H, m, 2×CH Ar), 7.13 (2H, d, J=8.7 Hz, 2×CH Ar), 6.96 (2H, d, J=8.7 Hz, 2×CH Ar), 5.64 (2H, s, CH$_2$), 2.56 (2H, t, J=7.8 Hz, CH$_2$Ph), 1.72-1.46 (2H, m, CH$_2$), 1.43-1.14 (10H, m, 5×CH$_2$), 0.89 (3H, t, J=7.0 Hz, CH$_3$); $^{13}$C NMR (50 MHz, CDCl$_3$): δ 189.17, 163.48, 155.92, 153.38, 136.93, 136.26, 129.35, 128.03, 127.26, 125.46, 122.48, 114.73, 70.47, 35.05, 31.86, 31.64, 29.46, 29.25, 22.65, 14.09; MS (ESI) m/z (%): 382.2 (100) [M+H]$^+$.

Ethyl 2-(2-(2-(4-octylphenoxy)acetyl)thiazol-4-yl)acetate (Compound Y, 43a) Yield 78%; White solid; $^1$H NMR (200 MHz, CDCl$_3$): δ 7.66 (s, 1H, SCH), 7.10 (d, J=8.2 Hz, 2H, 2×CH arom.), 6.90 (d, J=7.8 Hz, 2H, 2×CH arom.), 5.48 (s, 2H, OCH$_2$COO), 4.23 (q, J=7.2 Hz, COOCH$_2$), 3.93 (s, 2H, CH$_2$COO), 2.54 (t, J=7.6 Hz, CH$_2$Ph), 1.66-1.44 (m, 2H, CH$_2$), 1.40-1.14 (m, 13H, 5×CH$_2$, CH$_3$), 0.88 (3H, t, J=7.0 Hz, CH$_3$); $^{13}$C NMR (50 MHz, CDCl$_3$): δ 187.53, 169.81, 163.24, 155.90, 151.48, 136.16, 129.30, 124.27, 114.67, 70.26, 61.34, 36.84, 35.02, 31.85, 31.65, 29.44, 29.24, 22.63, 14.15, 14.09; MS (ESI) m/z (%): 418.1 (100) [M+H]$^+$.

Ethyl 2-(2-(2-(dodecyloxy)acetyl)thiazol-4-yl)acetate (Compound X, 43b). Yield 49%; Low mp white solid; $^1$H NMR (200 MHz, CDCl$_3$): δ 7.59 (s, 1H, CHS), 4.94 (s, 2H, OCH$_2$CO), 4.21 (q, J=7.0 Hz, 2H, COOCH$_2$), 3.89 (s, 2H, CH$_2$COO), 3.60 (t, J=6.6 Hz, 2H, OCH$_2$), 1.75-1.59 (m, 2H, CH$_2$), 1.45-1.18 (m, 21H, 9×CH$_2$, CH$_3$), 0.88 (t, J=7.0 Hz, CH$_3$); $^{13}$C NMR (50 MHz, CDCl$_3$): δ 189.60, 169.82, 163.81, 151.26, 123.71, 73.10, 72.20, 61.26, 36.86, 31.88, 29.55, 29.42, 29.31, 25.94, 22.65, 14.13, 14.09; MS (ESI) m/z (%): 398.3 (100) [M+H]$^+$.

Ethyl 2-(2-(dodecyloxy)acetyl)thiazole-4-carboxylate (Compound W, 43c). Yield 84%; Pale yellow solid; $^1$H NMR (200 MHz, CDCl$_3$): δ 8.44 (s, 1H, CHS), 5.04 (s, 2H, OCH$_2$CO), 4.44 (q, J=7.2 Hz, 2H, COOCH$_2$), 3.60 (t, J=6.6 Hz, 2H, OCH$_2$), 1.76-1.58 (m, 2H, CH$_2$), 1.46-1.17 (m, 21H, 9×CH$_2$, CH$_3$), 0.86 (t, J=6.6 Hz, CH$_3$); $^{13}$C NMR (50 MHz, CDCl$_3$): δ 189.68, 164.89, 160.58, 148.82, 132.94, 73.11, 72.22, 61.87, 31.86, 29.57, 29.54, 29.38, 29.29, 25.89, 22.63, 14.23, 14.06; MS (ESI) m/z (%): 384.3 (100) [M+H]$^+$.

Methyl 2-(2-(4-octylphenoxy)acetyl)thiazole-4-carboxylate (Compound A, 47) Yield 93%; Pale yellow solid; mp 69-71° C.; $^1$H NMR (200 MHz, CDCl$_3$): δ 8.52 (1H, s, SCH), 7.10 (2H, d, J=8.4 Hz, 2×CH Ar), 6.91 (2H, d, J=8.4 Hz, 2×CH Ar), 5.58 (2H, s, CH$_2$), 4.01 (3H, s, CH$_3$), 2.54 (2H, t, J=7.8 Hz, CH$_2$), 1.71-1.43 (2H, m, CH$_2$), 1.40-1.06 (10H, br s, 5×CH$_2$), 0.88 (3H, t, J=6.8 Hz, CH$_3$); $^{13}$C NMR (50 MHz, CDCl$_3$): δ; MS (ESI) m/z (%): 390.2 (100) [M+H]$^+$, 407.1 (70) [M+NH$_4$]$^+$.

EXAMPLE 6

Results of In Vitro and Ex Vivo Activities of Selected Oxothiazoles

Table 6 is shown below.

| Entry | CMP | Structure | In vitro assays | | | | | Ex vivo assays | | |
|---|---|---|---|---|---|---|---|---|---|---|
| | | | GIVA cPLA$_2$ | | GVIA iPLA$_2$ | GV sPLA$_2$ | cPLA2 vesicle assay | | AA release | | OA release |
| | | | % Inhib | X$_r$(50) | % Inhib | % Inhib | % Inhib | IC50 (μM)$^a$ | % Inhib$^b$ | IC50 (μM) | % Inhib$^b$ |
| 1 | D | | 40 | | 13 | 0 | 26 | NA | 12 | NA | 20 |
| 2 | C | | 58 | | 5 | 4 | 7 | NA | No | | 25 |

-continued

Table 6 is shown below.

| | | | In vitro assays | | | | | Ex vivo assays | | |
|---|---|---|---|---|---|---|---|---|---|---|
| | | | GIVA cPLA$_2$ | | GVIA iPLA$_2$ | GV sPLA$_2$ | cPLA2 vesicle assay | | AA release | | OA release |
| Entry | CMP | Structure | % Inhib | X$_r$(50) | % Inhib | % Inhib | % Inhib | IC50 (μM)[a] | % Inhib[b] | IC50 (μM) | % Inhib[b] |
| 3 | B | (biphenyl-O-CH$_2$-C(O)-thiazole) | 80 | | 23 | 41 | 26 | NA | 73 | 2.8 | 25 |
| 4 | T | (4-octylphenyl-O-CH$_2$-C(O)-thiazole) | >90 | 0.02 ± 0.007 | 67 | 46 | 43 | 1.2 | >90 | 3.6 | No |
| 5 | V | (4-octylphenyl-O-CH$_2$-C(O)-benzothiazole) | >90 | 0.06 ± 0.002 | 77 | 55 | No | | 71 | 5.3 | 35 |
| 6 | W | (C$_{11}$-O-CH$_2$-C(O)-thiazole-CO$_2$Et) | 48 | | 92 | 48 | 21 | NA | 9 | NA | No |
| 7 | X | (C$_{11}$-O-CH$_2$-C(O)-thiazole-CH$_2$CO$_2$Et) | 49 | | 91 | 55 | No | | No | | No |
| 8 | Y | (4-octylphenyl-O-CH$_2$-C(O)-thiazole-CH$_2$CO$_2$Et) | 64 | | 76 | 50 | 25 | NA | 71 | 5.0 | 20 |
| 9 | A | (4-octylphenyl-O-CH$_2$-C(O)-thiazole-CO$_2$Me) | >90 | 0.011 ± 0.005 | 86 | 41 | 74 | 0.3 | >90 | 0.6 | 40 |

[a] In vitro vesicle assay- inhibitors tested in 0-3 μM range; % inhibition at 1 μM oxothiazole given.
[b] Cellular assays using SW982 fibroblastlike synoviocytes- inhibitors tested in 0-20 μM range with 4h IL-1β stimulation; % inhibition at 10 μM oxothiazole given.
"No" denotes no effect whereas "NA" denotes that IC50 was not achieved within the given concentration range.
CMP denotes "compound".

In vitro inhibition of GIVA cPLA$_2$, GVIA iPLA$_2$ and GV sPLA$_2$. All synthesized oxothiazoles were tested for their in vitro activity on GIVA cPLA$_2$ using both mixed micellar and vesicles assays. In addition, their selectivity over GVIA iPLA$_2$ and GV sPLA$_2$ was studied using mixed micellar assays.

The in vitro inhibition of human GIVA cPLA$_2$, GVIA iPLA$_2$ and GV sPLA$_2$ was carried out using previously described mixed micelle-based assays.[31-33] The inhibition results are presented in Table 6, either as percent inhibition or as X$_I$(50) values. At first, the percent of inhibition for each PLA$_2$ enzyme at 0.091 mole fraction of each inhibitor was determined. Then, the X$_I$(50) values were measured for compounds that displayed greater than 90% inhibition of GIVA cPLA$_2$. The X$_I$(50) is the mole fraction of the inhibitor in the total substrate interface required to inhibit the enzyme activity by 50%.

Oxothiazole Compound D as well as its derivatives Compound C and Compound B containing a fluorine atom or a phenyl group at the para position, did not present any interesting inhibition of GIVA cPLA$_2$ (entries 1-3, Table 6). However, when an eight carbon atoms chain was introduced, a significant inhibitory activity was observed for Compound T (entry 4, Table 6). The replacement of the thiazole ring by the benzothiazole had as a result the reduction of the inhibitory potency (entry 5 vs entry 4, Table 6). Derivatives Compound V and Compound X containing an alkoxy group and a substituted thiazole group proved inactive (entries 6 and 7, Table 6). However, the introduction of a para-octyl-phenoxy group, together with an ester group on the thiazole ring, led to a potent inhibitor of GIVA cPLA$_2$ (Compound A) showing a X$_I$(50) value of 0.011 (entry 9, Table 6). Interestingly, moving the ester group one carbon atom away from the heterocyclic ring resulted in a dramatic loss of the activity for Compound Y (entry 8, Table 6).

The effect of the oxothiazoles synthesized on GIVA cPLA$_2$ was measured in vesicles as previously described[51,52] with modifications.[53] The results are presented in Table 6 and are in full agreement with those using the micellar assay. Compound A was found to be the most potent inhibitor of GIVA cPLA2 within this series of oxothiazoles with an IC$_{50}$ value of 0.3 µM (entry 9, Table 6). Compound T also presented an interesting inhibition in this vesicles assay with an IC$_{50}$ value of 1.2 µM (entry 4, Table 6). From both assays, it is clear that the introduction of the ethyl ester group directly on the heterocyclic ring substantially increases the potency of inhibition. This group presumably develops additional interactions within the enzyme's active site. Comparing the results obtained in mixed micelles and in vesicles is obvious that Compound A stands out in this series of oxothiazoles Example 7

Ex Vivo Inhibition of Arachidonic Acid and Oleic Acid Release in Synoviocytes

The effect of the oxothiazoles synthesized on the release of AA and OA in synoviocytes was evaluated as previously described.[54] The percent inhibition of AA and OA was determined at a 10 µM inhibitor concentration, while for the determination of the IC$_{50}$ value the inhibitors were tested in a 0-20 µM range after IL-1β stimulation for 4 h. A number of oxothiazoles (Compounds B, T, W and X) exhibited interesting inhibition of the AA release (Table 6). However, in accordance with the in vitro results, Compound A exhibited the most potent effect inhibiting the AA release with an IC$_{50}$ value of 0.6 µM, without having such potency in OA release (entry 9, Table 6). None of the oxothiazoles presented interesting inhibition of OA release.

In vivo studies. Compound A clearly presented a potent inhibitory effect of the GIVA cPLA$_2$ activity in vitro and a potent suppression of the AA release in cells. Thus, the study of its anti-inflammatory properties that may exhibit in vivo was designed. The collagen-induced arthritis (CIA) mouse model, which is the most commonly autoimmune model of rheumatoid arthritis,[55] was employed for the evaluation of the in vivo activity of Compound A. It has been previously shown that GIVA cPLA$_2$-deficient mice are resistant to CIA,[56] while the effect of the GIVA cPLA2 inhibitor pyrroxyphene has been studied.[32]

Example 8

Prophylactic Anti-inflammatory Effect of Compound A in CIA

The prophylactic effect of Compound A on CIA model in male DBA/1 mice[57] following intraperitoneal (ip) administration, treatment starting 1 hour prior to the last immunization was studied. A study comparing naïve mice (healthy, non-CIA, non-treated), vehicle-treated mice (CIA with DMSO, ip) and CIA mice treated daily with Compound A (7.5 mg/kg, ip) or MTX (0.3 mg/kg, ip) was performed. CIA developed rapidly in mice immunized with CII. In the prophylactic study, a 100% incidence of CIA was observed by day 29 in CII-immunized mice, with maximum AI of 8.55 observed at 41 days post immunization. The AI and incidence of all groups increased in a time-dependent mode from day 25 to day 41.

Figure 2:
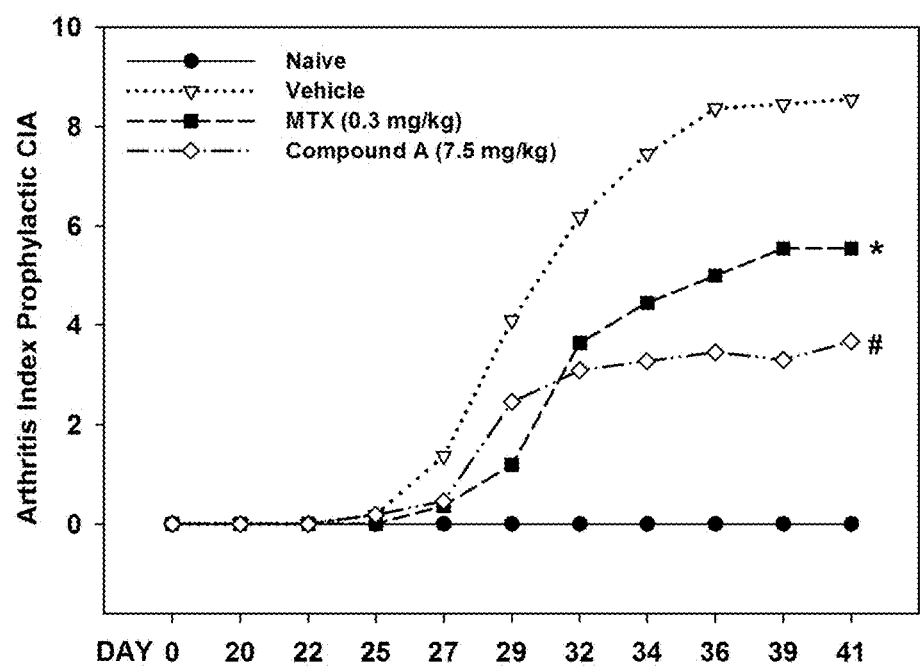
FIG. 2 is a graph showing that cPLA2alpha inhibitor Compound A inhibits arthritis progression than methotrexate in a mouse model. The cPLA2α inhibitor Compound A inhibits arthritis progression more efficiently than Methotrexate in the prophylactic CIA study design. *p<0.05, # p<0.005 vs. vehicle at study termination.
Figure 3:
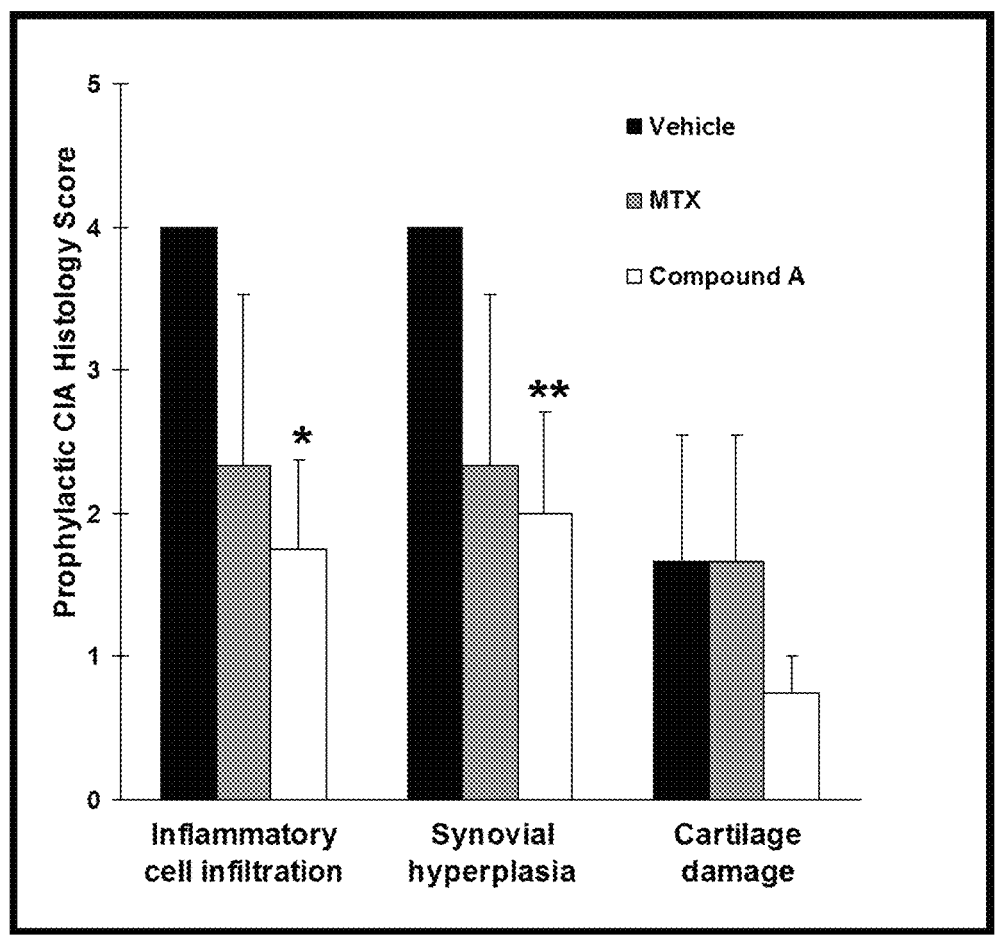
FIG. 3 is a graph showing that Compound A reduces parameters of joint inflammation and joint damage more efficiently than methotrexate in a mouse CIA model. Compound A reduces parameters of joint inflammation and joint damage more efficiently than MTX in a prophylactic CIA study design. Histopathology analysis was performed on hind paws from mice sacrificed at Day 32. Joint tissue was fixed in formalin, paraffin embedded, sectioned and H&E stained for pathological evaluation of the indicators 1) articular cavity and perintraperitonealheral tissue inflammatory cell infiltration; 2) capillary and synovial hyperplasia; and 3) articular cartilage surface damage according to the scoring system: 0=normal, 1=Minimal, 2=Mild, 3=Moderate. 4: Marked; 5: Severe, as judged by an observer blinded for the treatment. *p<0.03, **p<0.05 vs. Vehicle, error bars denote standard error of mean (n=3-10).

The AI of Compound A 7.5 mg/kg group on Days 32 to 41 (p<0.005) was significantly reduced in comparison to the CIA control group, similar to the effect of MTX (FIG. 2). Within the histology group, there was no statistical significance of AI between Compound A group and CIA control group (p>0.05, results not shown). There was no significant difference of the AI value between the histology group and main groups (p>0.05). Furthermore, at the end of the prophylactic study, 4 mice from each treated group and 3 mice from control groups were sacrificed and 1 hind paw of each mouse was collected for histopathology. Compared with the vehicle group, Compound A 7.5 mg/kg reduced articular cavity and peripheral tissue inflammatory cell infiltration p (p<0.03) and on reducing capillary and synovial hyperplasia (p<0.05), but had no significant effect on reducing cartilage damage (FIG. 3). In contrast, MTX did not reduce any of these parameters of joint inflammation and joint damage (p>0.05).

Example 9

Therapeutic Anti-inflammatory Effect of Compound A in CIA

Figure 4:
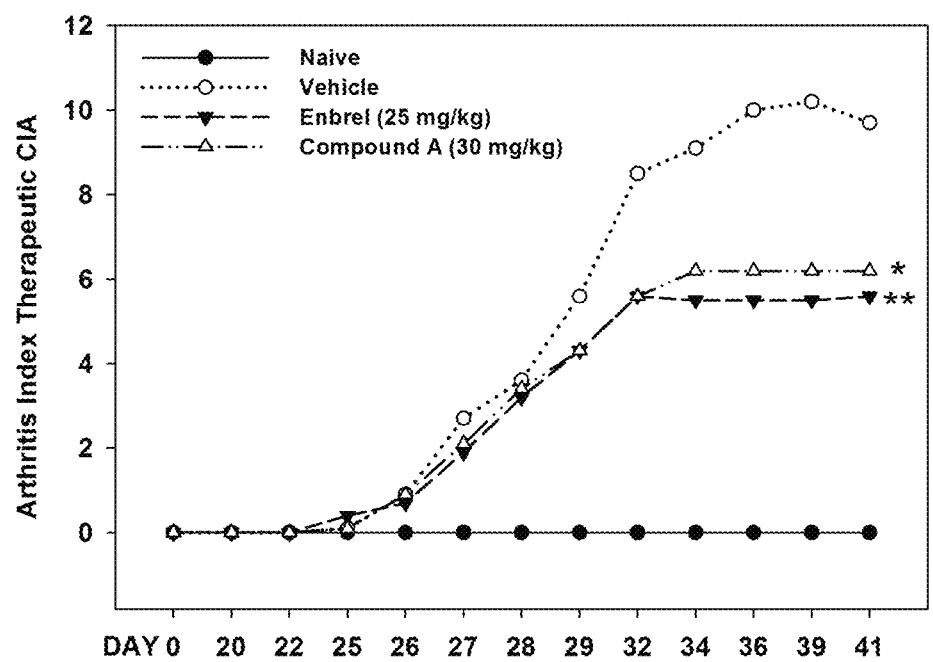
FIG. 4 is a graph showing that cPLA2alpha inhibitor Compound A reduces arthritic index comparable to Enbrel in a mouse CIA model. The cPLA2α inhibitor Compound A reduces the arthritic index in a manner comparable to Enbrel in a therapeutic CIA study *p<0.05, **p0.01. vehicle, at study termination.

The therapeutic effect of Compound A on CIA model in male DBA/1 mice following ip administration, treatment starting 7 days after the last immunization was explored. CIA developed rapidly in mice immunized with CII, with maximum AI of 10.2 observed at 39 days post immunization. The AI and incidence of vehicle- and Compound A treated groups increased in a time-dependent mode from Days 29 to 41. The AI observed was significantly decreased in comparison to that of the CIA control group both in the Compound A 30 mg/kg group and in the Enbrel group on Days 36 to 41 (P<0.05) (FIG. 4). Compound A and Enbrel performed equally well; there were no significant difference between these treatments groups.

Example 10

Compound A Efficiently Reduces Plasma $PGE_2$ Levels $PGE_2$ is recognized as an important contributor to the joint inflammation in rheumatoid arthritis,[60] and we investigated if plasma $PGE_2$ levels were changed in response to treatment. As shown in FIG. 5, plasma $PGE_2$ levels in Compound A-treated animals were significantly reduced by about 40% in both prophylactic and therapeutic modes of the CIA models (p<0.03). In the prophylactic study (n=11), $PGE_2$ levels in the DMSO treated vehicle group (223.4±107) were significantly elevated by 3-fold (p<0.001) compared to the non-arthritic healthy mice (70.4±37 ng/ml) (FIG. 5A). The elevated $PGE_2$ level was significantly reduced with Compound A (7.5 ng/ml, 139.8±92 ng/ml, p<0.03) comparable to MTX (0.3 mg/ml, 107.3±62 ng/ml, p<0.004) level. There were no significant differences between the treatment groups (p>0.05).

In the therapeutic study (n=10), similar results were obtained; $PGE_2$ levels in the DMSO treated vehicle group (231.1±110) were significantly elevated by 3-fold (p<0.001) compared to the non-arthritic healthy mice (70.6±36 ng/ml) (FIG. 5B). The elevated PGE2 levels were significantly reduced with Compound A (30 mg/ml, 139±55 ng/ml, n=1, p<0.03) treatment, but not with Enbrel (225 mg/kg, 187.5±74 ng/ml, non-significant p>0.05). There were no significant differences between the treatment groups (p>0.05).

In summary, Compound A produced $PGE_2$ plasma levels reduction comparable to that of the reference drug MTX in the prophylactic model, Furthermore, in the therapeutic model, it seems that Compound A caused more potent $PGE_2$ reduction in plasma than that of the reference drug Enbrel.

Materials and Methods

The following Materials and Methods were used as needed to perform Examples 7-9.

Biology. Recombinant human interleukin-1β (IL-1β) was from Roche (UK). Phosphate-buffered saline solution (PBS) was from Oxoid (UK). Labeled $^3$H-AA ([5,6,8,9,11,12,14, 15-$^3$H]-arachidonic acid (specific activity 180-240 Ci/mmol)), $^{14}$C-OA ([1-$^{14}$C]-oleic acid (specific activity 40-60 Ci/mmol)), L-α-1-palmitoyl-2-arachidonyl-[arachidonyl-1-$^{14}$C]-phosphatidylcholine (specific activity 40-60 Ci/mmol), and liquid scintillation cocktail Ultima Gold were from NEN Perkin Elmer (USA). Dulbecco's Modified Eagle Medium (DMEM), foetal bovine serum (FBS), fatty acid-free bovine serum albumin (fBSA), dimethyl-sulpfoxide (DMSO), gentamicin and L-glutamine were from Sigma-Aldrich (USA). EIA kit for PGE2 analysis was from Cayman Chemicals (USA).

In vitro mixed micellar assay. The activity of GIVA $cPLA_2$, GVIA $iPLA_2$ and GV $sPLA_2$ were determined using modified Dole Assay.[41-43] The buffer and substrate conditions were optimized for each enzyme assay as follows: (i) GIVA $cPLA_2$ substrate mixed-micelles were composed of 400 μM Triton X-100, 97 μM PAPC, 1.8 μM $^{14}$C-labeled PAPC, and 3 μM PIP2 in 100 mM HEPES buffer, pH 7.5, with 90 μM $CaCl_2$, 2 mM DTT, and 0.1 mg/ml BSA; (ii) GVI $iPLA_2$ substrate mixed-micelles were composed of 400 μM Triton X-100, 98.3 μM PAPC, and 1.7 μM $^{14}$C-labeled PAPC in buffer containing 100 mM HEPES, pH 7.5, 2 mM ATP, and 4 mM DTT; (iii) GV $sPLA_2$ substrate mixed-micelles were composed of 400 μM Triton X-100, 98.3 μM PAPC, and 1.7 μM $^{14}$C-labeled PAPC in buffer containing 50 mMTris, pH 8.0, and 5 mM 550 $CaCl_2$.

In vitro vesicles assay. GIVA $cPLA_2$ was measured as described[51,52] with modifications.[53] In short, recombinant human GIVA $cPLA_2$ enzyme was pre-incubated with DMSO (1%) with or without inhibitor in assay buffer (80 sec at 37° C., 10 min at 25° C.). Lipid vesicles of L-α-1-palmitoyl-2-arachidonyl-[arachidonyl-1-$^{14}$C]-phosphatidylcholine (4.3 nmol) were dried under a steam of $N_2$(g). The dried lipid was re-suspended in 2 ml assay buffer and sonicated twice (7 min, output 3.5 and 50% duty cycles, on ice) in a Branson Sonifier 250 (Branson Ultrasonic Corporation, Danbury, Conn.). Sonicated lipid (0.2 μM) was added to the reaction and incubated for 1 h at 37° C. followed by addition of a chloroform/methanol stop buffer to terminate the enzymatic reaction. The reaction mixture was separated by centrifugation (5 min, 1640×g). The lower phase was transferred to a glass tube and dried under a steam of $N_2$(g), re-suspended in chloroform/methanol (9:1, by volume) and applied to a silica gel. Free [1-$^{14}$C]arachidonic acid and, L-α-1-palmitoyl-2-arachidonyl-[arachidonyl-1-$^{14}$C]— phosphatidylcholine were separated by thin layer chromatography and analyzed as previously described.[54]

Cell culture. The human synovial sarcoma cell line SW982 was from ATCC (UK) and was used as a model system to monitor AA/OA release and activation of GIVA $cPLA_2$. SW982 cells were passaged bi-weekly by routine trypsin detachment and kept in a sub-confluent state. The cells were maintained in Dulbecco's Modified Eagle Medium (DMEM) supplemented with 10% FBS, 0.1 mg/mL gentamicin and 0.3 mg/mL L-glutamine at 37° C. with 10% CO2. For AA release, 5*10$^5$ cells were seeded pr well in a 48-well per plate format. Experiments were performed at 3 days post-confluency following overnight serum deprivation in serum-free DMEM to ensure differentiation and synchronization of the cells.

Ex vivo cellular arachidonic acid (AA) and oleic acid (OA) release assay. AA and OA release was analyzed as previously described.[54] At 2 days post-confluency, SW982 cells were serum-starved and labelled overnight with $^3$H-AA (0.4 μCi/ml) and $^{14}$C-OA (0.067 μCi/ml) in serum-free DMEM. Prior to the addition of oxothiazoles, the cells were washed twice with PBS containing fBSA (2 mg/ml) and PBS in order to remove unincorporated radioactivity. Cells were pretreated (1 h) with oxothiazoles prior to IL-1β stimulation (10 ng/mL, 4 h). Following IL-1β stimulation, the supernatants were cleared of detached cells by centrifugation (13000 rpm, 5 min). The release of $^3$H-AA and $^{14}$C-OA from the cells was assessed by liquid scintillation counting (LS 6500 Multi-Purpose Scintillation Counter, Beckman Coulter, Inc (USA). Adherent cells were dissolved in 1N NaOH in order to determine incorporated $^3$H-AA and $^{14}$C-OA in the cells by liquid scintillation counting. In all experiments, DMSO was included for vehicle control (>0.05%). Following treatments, cells were routinely observed by microscopy to ensure unaltered cell morphology, integrity and viability. The results are given as inhibition of released $^3$H-AA and $^{14}$C-OA in the supernatants relative to total $^3$H-AA and $^{14}$C-OA incorporated into the cells, from at least three independent experiments performed in triplicates.

$PGE_2$ analysis. $PGE_2$ EIA analysis of blood plasma from the prophylactic and therapeutic CIA studies was performed according to kit protocol. Plasma samples were diluted 1:1000-1:6000 in EIA buffer and allowed to hybridize over-night (18 hrs, 4° C.). The plate was read using a Multiscan plate reader (Ascent Labsystems) (OD550 nm). The corresponding Ascent software for Multiscan, Version 2.4.1 was used to obtain the data. $PGE_2$ levels for all treatments are shown relative to the DMSO-treated vehicle arthritic mice (n=10-11 mice in each category ±SD).

In vivo studies of Compound A. All in vivo studies were conducted in accordance with Standard Operating Procedures (SOP) and based on current International Conference on Harmonization (ICH) Harmonized Tripartite Guidelines[63] and generally accepted procedures for the testing of pharmaceutical compounds.

Separate prophylactic and therapeutic efficacy studies of COMPOUND A were performed. Methotrexate (MTX) (Jiangsu Hengrui Medicine Co, #11041411), Enbrel (Boehringer Ingelheim Pharma KG, #F39487), and vehicle (DMSO 100%, Sigma Aldrich #D2650) were administered to all groups via intraperitoneal injection once daily at a dose volume of 2 mL/kg. Observations for morbidity, mortality, injury, and the availability of food and water were conducted twice daily for all animals. Clinical observations were conducted daily during the study. Body weights were measured and recorded prior to randomization and then once daily during the study. Food consumption was measured and recorded daily. Biopsies for mid-term histology analysis were obtained on Day 13 in the prophylactic study. Necropsy examinations were performed at study termination; plasma samples were collected, organ weights were recorded Induction of collagen induced arthritis (CIA). For the prophylactic and the therapeutic studies, CIA was induced in male DBA/1 mice (except naïve mice) by immunization with 0.1 mL emulsion containing an equal volume of bovine type II collagen solution (2 mg/mL) and Freuds Complete Adjuvant at the tail base. The first injection was given on Day 0 and the second injection as booster was given on Day 21 (41-43). COMPOUND A, vehicle (DMSO) and MTX (0.3 mg/kg) were administered daily, Enbrel (25 mg/kg) was administrated twice a week. For the prophylactic study, treatment started one hour before the second collagen injection and continued for 21 days except for the histology groups that were sacrificed at Day 13 (33 days after immunization). For the therapeutic study, treatment started at Day 28 and continued for 14 days.

CIA Assessment and Treatment. CIA was assessed in mice by two blinded observers to measure paw swelling with a capacity measurement method on Day 0, Day 20, Day 22, Day 25, Day 27, Day 29, Day 32, Day 34, Day 36, Day 39 and Day 41 after the first injection. The occurrence of arthritis was observed by scoring all paws for severity of erythema and swelling, using a clinical score ranging from 0 (no swelling) to 4 (severe swelling and erythema). The physical condition of the animals was observed daily. Scores and overall evaluation of the histology group arms were performed in the same way as the main groups. However, the values measured were not included in the mean value calculations of the main groups. The YLS-7B Foot Volume Measuring Instrument (Huaibei China Bio Equipment) was used to measure the foot volume of mice. The occurrence of arthritis was observed by scoring all paws for severity of erythema and swelling, using a clinical score ranging from 0 (no swelling) to 4 (severe swelling and erythema), i.e. yielding maximum arthritic index (AI) score 16 (46).

Measurement of the histopathology and clinical observations. At the end of the studies, one hind foot of each mouse was collected for histopathology. The foot including the ankle was fixed in 10% neutral formalin. The ankle joints were decalcified, dehydrated, embedded in paraffin, sectioned and stained with routine hematoxylin-eosin. The sections were studied using light microscopy (10×10 and 20×10 magnifications). Arthritis damage (histological damage score) was evaluated and scored by an investigator blinded for the treatment regimen. The following parameters in the histopathology was evaluated 1) Articular cavity and peripheral tissue inflammatory cell infiltration; 2) Capillary and synovial hyperplasia; 3) Articular cartilage surface damage; 4) Endochondral and periosteal intramembranous ossification, each using a 0-4 grading system: "0" none; "1" minimal; "2" mild; "3" moderate; "4" marked; "5" severe damage.

Terminal Studies. All animals completed the scheduled test periods and were disposed with carbon dioxide and were subjected to necropsy, supervised by a pathologist. The sacrifices were performed at approximately 5 hours after the last ip injection. A macroscopic examination of the animal was performed on all sacrificed animals and any abnormality was recorded.

Statistical Analysis. Data of groups was examined by one-way analysis of variance, and individual groups were then compared with Student's unpaired t-test. Data was given as Mean±SD, if no particular indication was made. $p<0.05$ was considered significant.

Example 11

The therapeutic effect of AVX235 was tested in the rat streptozocin-induced model of human chronic renal disease and compared against losartan (positive control).
Materials and Methods Sprague Dawley rats (Harlan laboratories, USA) of an average weight of 130-150 grams were divided in groups of 8 animals per group and were treated according to table 7:

TABLE 7

| | | Study Details | | |
|---|---|---|---|---|
| Group | Treatment | Test agent | Number of rats | Urine Collection |
| | | Sham Control (vehicles) | | |
| 1 | Citrate | Vehicle | 8 | 15 days |
| | | STZ control (NO TEST AGENT) | | |
| 2 | STZ 65 mg/kg | Vehicle | 8 | 15 days |
| | | AVX235 | | |
| 5 | STZ 65 mg/kg | 10 mg/kg | 8 | 15 days |
| | | Reference control (Losartan) | | |
| 6 | STZ 65 mg/kg | 30 mg/kg | 8 | 15 days |

AVX235 was injected intraperitoneally, once daily for the first 4 days and then every two days. Losartan was administered daily, by oral gavage. At 2 weeks post experiment initiation, urine was collected over a period of 24 h and total protein in mg was measured.

FIG. 6 shows the results of the performed experiment in STZ-treated rats. As predicted, STZ induced increased protein levels in rat urine at 2 weeks post experiment initiation; this is consistent with the progressive renal disease observed in response to STZ administration in this model. On the contrary, losartan protected rats from the STZ effect as urine protein levels in this group were comparable to urine protein levels in the control rat group that hasn't received STZ (Sham group). No adverse events were observed in rats in response to the various treatments as judged by behavioral and clinical observation and body weight controls indicating that the treatments were not-toxic.

AVX235, at this concentration and dosing regime, showed positive and significant therapeutic effects in the STZ-model. It protected renal function at the highest dose used; the observed effect was about 50% of obtained with clinical agent losartan.

It is believed that consideration of the following references numbered 1-60 will aid in the appreciation of Examples 4-11 shown above in which one or more of the following papers is referred to by number.

1. Podo F, et al.: Triple-negative breast cancer: present challenges and new perspectives. Mol Oncol 2010, 4: 209-229.
2. Patel M I, et al.: Cytosolic phospholipase A2-alpha: a potential therapeutic target for prostate cancer. Clin Cancer Res 2008, 14: 8070-8079.
3. Nakanishi M, Rosenberg D W: Roles of cPLA2alpha and arachidonic acid in cancer. Biochim Biophys Acta 2006, 1761: 1335-1343.
4. Caiazza F, et al.: Cytosolic phospholipase A2-alpha expression in breast cancer is associated with EGFR expression and correlates with an adverse prognosis in luminal tumours. Br J Cancer 2011, 104: 338-344.
5. Hughes-Fulford M, et al.: Arachidonic acid activates phosphatidylinositol 3-kinase signaling and induces gene expression in prostate cancer. Cancer Res 2006, 66: 1427-1433.
6. Linkous A G, et al.: Cytosolic phospholipase A2 and lysophospholipids in tumor angiogenesis. J Natl Cancer Inst 2010, 102: 1398-1412.
7. Wen Z H, et al.: Critical role of arachidonic acid-activated mTOR signaling in breast carcinogenesis and angiogenesis. Oncogene 2013, 32: 160-170.
8. Grinde M T, et al.: Interplay of choline metabolites and genes in patient-derived breast cancer xenografts. Breast Cancer Research 2013, Submitted.
9. Moestue S A, et al.: Distinct choline metabolic profiles are associated with differences in gene expression for basal-like and luminal-like breast cancer xenograft models. BMC Cancer 2010, 10: 433.
10. Bergamaschi A, et al.: Molecular profiling and characterization of luminal-like and basal-like in vivo breast cancer xenograft models. Mol Oncol 2009, 3: 469-482.
11. Huuse E M, et al.: In vivo MRI and histopathological assessment of tumor microenvironment in luminal-like and basal-like breast cancer xenografts. J Magn Reson Imaging 2012, 35: 1098-1107.
12. Moestue S A, et al.: Low-molecular contrast agent DCE-MRI and DW-MRI in early assessment of bevacizumab therapy in breast cancer xenografts. J Magn Reson Imaging 2013.
13. Moestue S A, et al.: Reduced pAkt levels and early metabolic changes predict response to PI3K inhibition in basal-like breast cancer xenografts. Breast Cancer Research 2013.
14. Borgan, E. et al. Subtype-specific response to bevacizumab is reflected in the metabolome and transcriptome of breast cancer xenografts Mol. Oncol. 7 (2013) 130-142.
15. Clark, J. D.; Lin, L. L.; Kriz, R. W.; Ramesha, C. S.; Sultzman, L. A.; Lin, A. Y.; Milona, N.; Knopf, J. L. A Novel Arachidonic Acid-Selective Cytosolic $PLA_2$ Contains a $Ca^{2+}$-Dependent Translocation Domain with Homology to PKC and GAP. Cell 1991, 65, 1043-1051.16. Kramer, R. M.; Roberts, E. F.; Manetta, J.; Putnam, J. E. The $Ca^{2+}$-Sensitive Cytosolic Phospholipase $A_2$ is a 100-Kda Protein in Human Monoblast U937 Cells. J. Biol. Chem. 1991, 266, 5268-5272.
17. Street, I. P.; Lin, H. K.; Laliberte, F.; Ghomashchi, F.; Wang, Z.; Perrier, H.; Tremblay, N. M.; Huang, Z.; Weech, P. K.; Gelb, M. H. Slow- and Tight-Binding Inhibitors of the 85-Kda Human Phospholipase $A_2$. Biochemistry 1993, 32, 5935-5940.
18. Bonventre, J. V.; Huang, Z.; Taheri, M. R.; O'Leary, E.; Li, E.; Moskowitz, M. A.; Sapirstein, A. Reduced Fertility and Postischaemicbrain Injury in Mice Deficient in Cytosolic Phospholipase $A_2$. Nature 1997, 390, 622-625.
19. Uozumi, N.; Kume, K.; Nagase, T.; Nakatani, N.; Ishii, S.; Tashiro, F.; Komagata, Y.; Maki, K.; Ikuta, K.; Ouchi, Y.; Miyazaki, J.; Shimizu, T. Role of Cytosolic Phospholipase $A_2$ in Allergic Response and Parturition. Nature 1997, 390, 618-622.
20. McKew, J. C.; Foley, M. A.; Thakker, P.; Behnke, M. L.; Lovering, F. E.; Sum, F.-W.; Tam, S.; Wu, K.; Shen, M. W. H.; Zhang, W.; Gonzalez, M.; Liu, S.; Mahadevan, A.; Sard, H.; Khor, S. P.; Clark J. D. Inhibition of Cytosolic Phospholipase $A_2\alpha$: Hit to Lead Optimization. J. Med. Chem. 2006, 49, 135-158.
21. Lee, K. L.; Foley, M. A.; Chen, L.; Behnke, M. L.; Lovering, F. E.; Kirincich, S. J.; Wang, W.; Shim, J.; Tam, S.; Shen, M. W. H.; Khor, S. P.; Xu, X.; Goodwin, D. G.; Ramarao, M. K.; Nickerson-Nutter, C.; Donahue, F.; Ku, M. S.; Clark, J. D.; McKew J. C. Discovery of Ecopladib, an Indole Inhibitor of Cytosolic Phospholipase $A_2\alpha$. J. Med. Chem. 2007, 50, 1380-1400.
22. Lee, K. L.; Behnke, M. L.; Foley, M. A.; Chen, L.; Wang, W.; Vargas, R.; Nunez, J.; Tam, S.; Mollova, N.; Xu, X.; Shen, M. W. H.; Ramarao, M. K.; Goodwin, D. G.; Nickerson-Nutter, C. L.; Abraham, W. M.; Williams, C.; Clark, J. D.; McKew, J. C. Benzenesulfonamide Indole Inhibitors of Cytosolic Phospholipase A2α: Optimization of In Vitro Potency and Rat Pharmacokinetics for Oral Efficacy. Bioorg. Med. Chem. 2008, 16, 1345-1358.
23. McKew, J. C.; Lee, K. L.; Shen, M. W. H.; Thakker, P.; Foley, M. A.; Behnke, M. L.; Hu, B.; Sum, F.-W.; Tam, S.; Hu, Y.; Chen, L.; Kirincich, S. J.; Michalak, R.; Thomason, J.; Ipek, M.; Wu, K.; Wooder, L.; Ramarao, M. K.; Murphy, E. A.; Goodwin, D. G.; Albert, L.; Xu, X.; Donahue, F.; Ku, M. S.; Keith, J.; Nickerson-Nutter, C. L.; Abraham, W. M.; Williams, C.; Hegen, M.; Clark, J. D. Indole Cytosolic Phospholipase $A_2\alpha$ Inhibitors: Discovery and In Vitro and In Vivo Characterization of 4-{3-[5-Chloro-2-(2-{[(3,4-dichlorobenzyl)sulfonyl]amino}) ethyl)-1H-indol-3-yl]propyl}Benzoic Acid, Efipladib. J. Med. Chem. 2008, 51, 3388-3413.
24. http://clinicaltrials.gov/Identifier: NCT00396955.
25. Dennis, E. A.; Cao, J.; Hsu, Y. H.; Magrioti, V.; Kokotos, G. Phospholipase A2 Enzymes: Physical Structure, Biological Function, Disease Implication, Chemical Inhibition, and Therapeutic Intervention Chem. Rev. 2011, 111, 6130-6185.
26. Murakami, M.; Taketomi, Y.; Miki, Y.; Sato, H.; Hirabayashi, T.; Yamamoto, K. Recent Progress in Phospholipase $A_2$ Research: From Cells to Animals to Humans. Prog. Lipid Res. 2011, 50, 152-192.
27. Ghosh, M.; Tucker, D. E.; Burchett, S. A.; Leslie, C. C. Properties of the Group IV Phospholipase $A_2$ Family. Prog. Lipid Res. 2006, 45, 487-510.
28. Magrioti, V.; Kokotos, G. Phospholipase $A_2$ Inhibitors as Potential Therapeutic Agents for the Treatment of Inflammatory Diseases. Expert Opin. Ther. Pat. 2010, 20, 1-18.

29. Magrioti, V.; Kokotos, G. Phospholipase $A_2$ Inhibitors for the Treatment of Inflammatory Diseases: A Patent Review (2010-Present). *Expert Opin. Ther. Pat.* 2013, 23, 333-344.
30. Seno, K.; Okuno, T.; Nishi, K.; Murakami, Y.; Watanabe, F.; Matsuura, T.; Wada, M.; Fujii, Y.; Yamada, M.; Ogawa, T.; Okada, T.; Hashizume, H.; Kii, M.; Hara, S.-I.; Hagishita, S.; Nakamoto, S.; Yamada, K.; Chikazawa, Y.; Ueno, M.; Teshirogi, I.; Ono, T.; Ohtani, M. Pyrrolidine inhibitors of human cytosolic phospholipase $A_2$. *J. Med. Chem.* 2000, 43, 1041-1044
31. Eno, K.; Okuno, T.; Nishi, K.; Murakami, Y.; Yamada, K.; Nakamoto, S.; Ono, T. Pyrrolidine inhibitors of human cytosolic phospholipase A2. Part 2: synthesis of potent and crystallized 4-triphenylmethylthio derivative 'pyrrophenone'. *Bioorg. Med. Chem. Lett.* 2001, 11, 587-590.
32. Tai, N.; Kuwabara, K.; Kobayashi, M.; Yamada, K.; Ono, T.; Seno, K.; Gahara, Y.; Ishizaki, J.; Y. Hori. Cytosolic phospholipase $A_2$ alpha inhibitor, pyrroxyphene, displays anti-arthritic and anti-bone destructive action in a murine arthritis model. *Inflamm. Res.* 2010, 59, 53-62.
33. Ludwig, J.; Bovens, S.; Brauch, C.; Schulze Elfringhoff, A.; Lehr, M. Design and synthesis of 1-indol-1-yl-propan-2-ones as inhibitors of human cytosolic phospholipase $A_2\alpha$. *J. Med. Chem.* 2006, 49, 2611-2620.
34. Hess, M.; Schulze Elfringhoff, A.; Lehr, M. 1-(5-Carboxy- and 5-carbamoylindol-1-yl)propan-2-ones as inhibitors of human cytosolic phospholipase $A_2\alpha$: bioisosteric replacement of the carboxylic acid and carboxamide moiety. *Bioorg. Med. Chem.* 2007, 15, 2883-2891.
35. Fritsche, A.; Schulze Elfringhoff, A.; Fabian, J.; Lehr, M. 1-(2-Carboxyindol-5-yloxy)propan-2-ones as inhibitors of human cytosolic phospholipase $A_2\alpha$: synthesis, biological activity, metabolic stability, and solubility. *Bioorg. Med. Chem.* 2008, 16, 3489-3500.
36. Bovens, S.; Schulze Elfringhoff, A.; Kaptur, M.; Reinhardt, D.; Schäfers, M.; Lehr, M. 1-(5-Carboxyindol-1-yl)propan-2-one inhibitors of human cytosolic phospholipase $A_2\alpha$: Effect of substituents in position 3 of the indole scaffold on inhibitory potency, metabolic stability, solubility, and bioavailability. *J. Med. Chem.* 2010, 53, 8298-8308.
37. Drews, A.; Bovens, S.; Roebrock, K.; Sunderkötter, C.; Reinhardt, D.; Schäfers, M.; van der Velde, A.; Schulze Elfringhoff, A.; Fabian, J.; Lehr, M. 1-(5-carboxyindol-1-yl)propan-2-one inhibitors of human cytosolic phospholipase $A_2\alpha$ with reduced lipophilicity: Synthesis, biological activity, metabolic stability, solubility, bioavailability, and topical in vivo activity. *J. Med. Chem.* 2010, 53, 5165-5178.
38. Kaptur, M.; Schulze Elfringhoff, A.; Lehr, M. Structure-activity relationship studies on 1-(5-carboxyindol-1-yl)-propan-2-one inhibitors of human cytosolic phospholipase $A_2\alpha$: Variation of the activated ketone moiety. *Bioorg. Med. Chem. Lett.* 2011, 21, 1773-1776.
39. Roebrock, K.; Wolf, M.; Bovens, S.; Lehr, M.; Sunderkötter, C. Inhibition of benzalkonium chloride-induced skin inflammation in mice by an indol-1-ylpropan-2-one inhibitor of cytosolic phospholipase $A_2\alpha$. *Br. J. Dermatol.* 2012, 166, 306-316.
40. Kokotos, G.; Kotsovolou, S.; Six, D. A.; Constantinou-Kokotou, V.; Beltzner, C. C.; Dennis, E. A. Novel 2-Oxoamide Inhibitors of Human Group IVA Phospholipase A2. *J. Med. Chem.* 2002, 45, 2891-2893.
41. Kokotos, G.; Six, D. A.; Loukas, V.; Smith, T.; Constantinou-Kokotou, V.; Hadjipavlou-Litina, D.; Kotsovolou, S.; Chiou, A.; Beltzner, C. C.; Dennis, E. A. Inhibition of Group IVA Cytosolic Phospholipase A2 by Novel 2-Oxoamides In Vitro, In Cells and In Vivo. *J. Med. Chem.* 2004, 47, 3615-3628.
42. Stephens, D.; Barbayianni, E.; Constantinou-Kokotou, V.; Peristeraki, A.; Six, D. A.; Cooper, J.; Harkewicz, R.; Deems, R. A.; Dennis, E. A.; Kokotos, G. Differential Inhibition of Group IVA and Group VIA Phospholipases A(2) by 2-Oxoamides. *J. Med. Chem.* 2006, 49, 2821-2828.
43. Six, D. A.; Barbayianni, E.; Loukas, V.; Constantinou-Kokotou, V.; Hadjipavlou-Litina, D.; Stephens, D.; Wong, A. C.; Magrioti, V.; Moutevelis-Minakakis, P.; Baker, S.; Dennis, E. A.; Kokotos, G. Structure-Activity Relationship of 2-Oxoamide Inhibition of Group IVA Cytosolic Phospholipase A2 and Group V Secreted Phopholipase A2. *J. Med. Chem.* 2007, 50, 4222-4235.
44. Antonopoulou, G.; Barbayianni, E.; Magrioti, V.; Cotton, N.; Stephens, D.; Constantinou-Kokotou, V.; Dennis, E. A.; Kokotos, G. Structure-Activity Relationships of Natural and Non-Natural Amino Acid-Based Amide and 2-Oxoamide Inhibitors of Human Phospholipase $A_2$ Enzymes. *Bioorg. Med. Chem.* 2008, 16, 10257-10269.
45. Baskakis, C.; Magrioti, V.; Cotton, N.; Stephens, D.; Constantinou-Kokotou, V.; Dennis, E. A.; Kokotos, G. Synthesis of Polyfluoroketones for Selective Inhibition of Human Phospholipase A2 Enzymes. *J. Med. Chem.* 2008, 51, 8027-8037.
46. Kokotos, G.; Hsu, Y. H.; Burke, J. E.; Baskakis, C.; Kokotos, C. G.; Magrioti, V.; Dennis, E. A. Potent and Selective Fluoroketone Inhibitors of Group VIA Calcium-Independent Phospholipase A2. *J. Med. Chem.* 2010, 53, 3602-3610.
47. Magrioti, V.; Nikolaou, A.; Smyrniotou, A.; Shah, I.; Constantinou-Kokotou, V.; Dennis, E. A.; Kokotos, G. New Potent and Selective Polyfluoroalkyl Ketone Inhibitors of GVIA Calcium-Independent Phospholipase $A_2$. *Bioorg. Med. Chem.* 2013, 21, 5823-5829.
48. Burke, J. E.; Babakhani, A.; Gorfe, A. A.; Kokotos, G.; Li, S.; Woods, V. L., Jr.; McCammon, J. A.; Dennis, E. A. Location of Inhibitors Bound to Group IVA Phospholipase A2 Determined by Molecular Dynamics and Deuterium Exchange Mass Spectrometry *J. Am. Chem. Soc.* 2009, 131, 8083-8091.
49. Hsu, Y.-H.; Bucher, D.; Cao, J.; Li, S.; Yang, S.-W.; Kokotos, G.; Woods, V. L., Jr.; McCammon, J. A.; Dennis, E. A. Fluoroketone Inhibition of $Ca^{2+}$-Independent Phospholipase A2 through Binding Pocket Association Defined by Hydrogen/Deuterium Exchange and Molecular Dynamics *J. Am. Chem. Soc.* 2013, 135, 1330-1337.
50. Dessen, A.; Tang, J.; Schmidt, H.; Stahl, M.; Clark, J. D.; Seehra, J.; Somers, W. S. Crystal Structure of Human Cytosolic Phospholipase $A_2$ Reveals a Novel Topology and Catalytic Mechanism. *Cell* 1999, 97, 349-360.
51. Wijkander, J.; Sundler, R. An 100-Kda Arachidonate-Mobilizing Phospholipase $A_2$ in Mouse Spleen and the Macrophage Cell Line J774. *Eur. J. Biochem.* 1991, 202, 873-880.
52. Huwiler, A.; Feuerherm, A. J.; Sakem, B.; Pastukhov, O.; Filipenko, I.; Nguyen, T.; Johansen, B. The Ω3-Polyunsaturated Fatty Acid Derivatives AVX001 and AVX002 Directly Inhibit Cytosolic Phospholipase $A_2$ and Suppress $PGE_2$ Formation in Mesangial Cells. *Br. J. Pharmacol.* 2012, 167, 1691-1701.
53. Lucas, K. K.; Dennis, E. A. Distinguishing Phospholipase $A_2$ Types in Biological Samples by Employing Group-Specific Assays in the Presence of Inhibitors. *Prostaglandins Other Lipid Mediat.* 2005, 77, 235-248.
54. Anthonsen, M. W.; Solhaug, A.; Johansen, B. Functional Coupling between Secretory and Cytosolic Phospholipase $A_2$ Modulates Tumor Necrosis Factor-Alpha- and Interleukin-1beta-Induced NF-Kappa B Activation. *J. Biol. Chem.* 2001, 276, 30527-30536.
55. Brand, D. D.; Latham, K. A.; Rosloniec, E. F. Collagen-induced Arthritis. *Nature Protocols* 2007, 2, 1269-1275.
56. Hegen, M.; Sun, L.; Uozumi, N.; Kume, K.; Goad, M. E.; Nickerson-Nutter, C. L.; Shimizu, T.; Clark. J. D. Cytosolic Phospholipase $A_2\alpha$-deficient Mice Are Resistant to Collagen-induced Arthritis. *J. Exp. Med.* 2003, 197, 1297-1302.
57. Hegen, M.; Keith Jr, J. C.; Collins, M.; Nickerson-Nutter, C. L. Utility of Animal Models for Identification of Potential Therapeutics for Rheumatoid Arthritis. *Ann. Rheum. Dis.* 2008, 67, 1505-1515.
58. Sheibanie, A. F.; Khayrullina, T.; Safadi, F. F.; Ganea, D. Prostaglandin E2 Exacerbates Collagen-Induced Arthritis in Mice through the Inflammatory Interleukin-23/Interleukin-17 Axis. *Arthritis Rheum.* 2007, 56, 2608-2619.
59. Sathisha, K. R.; Khanum, S. A.; Chandra, J. N. N. S.; Ayisha, F.; Balaji, S.; Marathe, G. K.; Gopal, S.; Rangappa K. S. Synthesis and Xanthine Oxidase Inhibitory Activity of 7-Methyl-2-(phenoxymethyl)-5H-[1,3,4]thiadiazolo[3,2-a]pyrimidin-5-one Derivatives. *Bioorg. Med. Chem.* 2011, 19, 211-220.
60. Beutner, G. L.; Kuethe, J. T.; Kim, M. M.; Yasuda, N. Expedient Synthesis of 3-Alkoxymethyl- and 3-Aminomethyl-Pyrazolo[3,4-b]pyridines. *J. Org. Chem.* 2009, 74, 789-794.
61. Guilford, W. J.; Bauman, J. G.; Skuballa, W.; Bauer, S.; Wei, G. P.; Davey, D.; Schaefer, C.; Mallari, C.; Terkelsen, J.; Tseng, J.-L.; Shen, J.; Subramanyam, B.; Schottelius, A. J.; Parkinson, J. F. Novel 3-Oxa Lipoxin A4 Analogues with Enhanced Chemical and Metabolic Stability Have Anti-inflammatory Activity in Vivo. *J. Med. Chem.* 2004, 47, 2157-2165.
62. Ozcan, S.; Kazi, A.; Marsilio, F.; Fang, B.; Guida, W. C.; Koomen, J.; Lawrence, H. R.; Sebti, S. M. Oxadiazole-isopropylamides as Potent and Noncovalent Proteasome Inhibitors. *J. Med. Chem.* 2013, 56, 3783-3805.
63. EMEA: Non-Clinical Safety Studies for the Conduct of Human Clinical Trials for Pharmaceuticals. ICH M3 (R2), 2009, 1-25, European Medicines Agency.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The invention claimed is:
1. A compound represented by the following structural formula:

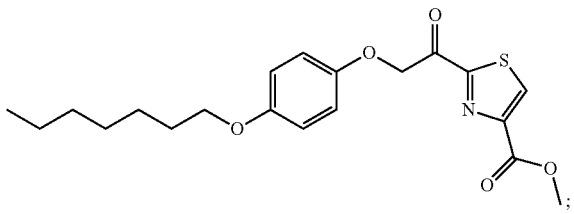 [SMILES: CCCCCCCOc1ccc(OCC(=O)c2nc(C(=O)OC)cs2)cc1]

or a pharmaceutically acceptable salt thereof.

2. A pharmaceutical composition comprising the compound of claim 1 or a pharmaceutically acceptable salt thereof, and a pharmaceutically acceptable carrier or diluent.

3. A method for treating a subject suffering from rheumatoid arthritis comprising administering to the subject an effective amount of the compound of claim 1 or a pharmaceutically acceptable salt thereof.

4. The method of claim 3, wherein the compound or pharmaceutically acceptable salt thereof is administered to a subject as a sole active agent.

5. The method of claim 3, wherein the compound or pharmaceutically acceptable salt thereof is administered along with one or more of a steroid, non-steroidal anti-inflammatory drug (NSAID), analgesic, or disease modifying antirheumatic drug (DMARD).

6. The method of claim 5, wherein the compound or pharmaceutically acceptable salt thereof is administered along with an analgesic selected from aspirin or ibuprofen.

7. The method of claim 5, wherein the compound or pharmaceutically acceptable salt thereof is administered along with a disease modifying antirheumatic drug (DMARD) selected from methotrexate, leflunomide, hydroxychloroquine, or sulfasalazine.

* * * * *

UNITED STATES PATENT AND TRADEMARK OFFICE
CERTIFICATE OF CORRECTION

PATENT NO. : 10,259,801 B2
APPLICATION NO. : 15/789834
DATED : April 16, 2019
INVENTOR(S) : Berit Johansen et al.

It is certified that error appears in the above-identified patent and that said Letters Patent is hereby corrected as shown below:

On the Title Page

Item (54) Delete "ANTI-INFLAMMATORY AND ANTITUMOR 2-OXOTHIAZOLES ABD 2-OXOTHIOPHENES COMPOUNDS" and insert -- ANTI-INFLAMMATORY AND ANTITUMOR 2-OXOTHIAZOLES AND 2-OXOTHIOPHENES COMPOUNDS --.

Item (72) Delete "Sanderberg" and insert -- Sandberg --.

Signed and Sealed this
Thirtieth Day of June, 2020

Andrei Iancu
*Director of the United States Patent and Trademark Office*